(12) United States Patent
Tiwari et al.

(10) Patent No.: US 12,390,467 B2
(45) Date of Patent: Aug. 19, 2025

(54) NECROPTOSIS INDUCERS OR AUTOPHAGY INHIBITORS OR A COMBINATION THEREOF

(71) Applicant: The University of Toledo, Toledo, OH (US)

(72) Inventors: Amit K. Tiwari, Toledo, OH (US); Chandrabose Karthikeyan, Toledo, OH (US); Angelique Nyinawabera, Toledo, OH (US)

(73) Assignee: The University of Toledo, Toledo, OH (US)

( * ) Notice: Subject to any disclaimer, the term of this patent is extended or adjusted under 35 U.S.C. 154(b) by 1054 days.

(21) Appl. No.: 17/047,155

(22) PCT Filed: Apr. 12, 2019

(86) PCT No.: PCT/US2019/027167
§ 371 (c)(1),
(2) Date: Oct. 13, 2020

(87) PCT Pub. No.: WO2019/200221
PCT Pub. Date: Oct. 17, 2019

(65) Prior Publication Data
US 2021/0154197 A1    May 27, 2021

Related U.S. Application Data

(60) Provisional application No. 62/657,075, filed on Apr. 13, 2018.

(51) Int. Cl.
*A61K 31/519* (2006.01)
*A61P 35/00* (2006.01)

(52) U.S. Cl.
CPC ............ *A61K 31/519* (2013.01); *A61P 35/00* (2018.01)

(58) Field of Classification Search
CPC ............................. A61K 31/519; A61P 35/00
See application file for complete search history.

(56) References Cited

PUBLICATIONS

Henderson et al.; "Inhibition of Ascites Tumor Growth by 4-Aminopyrazolo-(3,4-d)pyrimidine in Combination with Azaserine, 6- Mercaptopurine, and Thioguanine"; 1960; Cancer Research; 20:1618-1624 (Year: 1960).*

* cited by examiner

*Primary Examiner* — Timothy P Thomas
(74) *Attorney, Agent, or Firm* — MacMillan, Sobanski & Todd, LLC

(57) ABSTRACT

Thieno-pyrimidin-4-yl-hydrazinylidene compounds, and methods of using the same, are described.

2 Claims, 57 Drawing Sheets

| Compounds | IC$_{50}$ ± SD (µM) | | | | |
|---|---|---|---|---|---|
| | TNBC | | | Non-TNBC | |
| | MDA-MB231 | MDA-MB468 | BT-20 | ZR-75-1 | MCF-7 |
| TPH101 | >100 | >100 | >100 | >100 | >100 |
| TPH102 | 7.48 ± 4.70 | 4.10 ± 0.28 | 3.78 ± 1.81 | >100 | 6.29 ± 1.21 |
| TPH103 | 78.53 ± 21.50 | >100 | >100 | >100 | 15.69 ± 9.53 |
| TPH104 | 0.19 ± 0.01 | 0.25 ± 0.05 | 0.29 ± 0.05 | 8.56 ± 1.95 | 3.84 ± 1.36 |
| TPH105 | 43.33 ± 2.80 | >100 | >100 | >100 | 19.25 ± 0.90 |
| TPH106 | 46.38 ± 2.70 | 27.64 ± 5.52 | >100 | >100 | 24.34 ± 6.31 |
| TPH107 | >100 | 62.00 ± 10.00 | >100 | >100 | >100 |
| TPH108 | >100 | >100 | >100 | >100 | >100 |
| TPH109 | >100 | >100 | >100 | >100 | >100 |

FIG. 29

| Compounds | IC$_{50}$ ± SD (µM) | | | | | |
|---|---|---|---|---|---|---|
| | Colon | | | Prostate | Ovarian | Lung |
| | HCT-116 | LOVO | S1 | DU145 | Ov2008 | H460 |
| TPH101 | >100 | >100 | >100 | >100 | >100 | >100 |
| TPH102 | 5.15 ± 0.54 | 52.37 ± 6.70 | 15.78 ± 4.75 | 50.93 ± 6.03 | 3.50 ± 0.07 | 20.09 ± 3.67 |
| TPH103 | >100 | 53.77 ± 11.94 | >100 | >100 | >100 | >100 ± |
| TPH104 | 0.64 ± 0.12 | 1.40 ± 0.32 | 1.65 ± 0.25 | 0.66 ± 0.15 | 0.73 ± 0.04 | 2.54 ± 0.13 |
| TPH105 | >100 | >100 | >100 | >100 | >100 | >100 |
| TPH106 | >100 | 97.80 ± 3.11 | >100 | >100 | 93.11 ± 9.75 | >100 |
| TPH107 | >100 | >100 | >100 | 94.09 ± 8.36 | >100 | >100 |
| TPH108 | >100 | 60.37 ± 5.01 | >100 | 97.00 ± 2.12 | >100 | >100 |
| TPH109 | >100 | >100 | >100 | >100 | >100 | >100 |

FIG. 30

NECROPTOSIS INDUCERS OR AUTOPHAGY INHIBITORS OR A COMBINATION THEREOF

RELATED APPLICATIONS

This application is a national stage application filed under 35 U.S.C. § 371 of international application PCT/US19/027167, filed under the authority of the Patent Cooperation Treaty on Apr. 12, 2019, which claims priority to U.S. Provisional Application No. 62/657,075 filed under 35 U.S.C. § 111 (b) on Apr. 13, 2018, the disclosure of which is incorporated herein by reference in its entirety.

STATEMENT REGARDING FEDERALLY SPONSORED RESEARCH

This invention was made with no government support. The government has no rights in this invention.

BACKGROUND OF THE INVENTION

Breast cancer is the leading cause of cancer related deaths in women worldwide and is the most aggressive, commonly diagnosed type of cancer among women in all ethnic groups. In addition, breast cancer is a heterogeneous disease and the stage, grade, and status of three therapeutically relevant receptors, the estrogen receptor (ER), progesterone receptor (PR) and human epidermal growth factor receptor 2 (HER2) have been used for clinical prognosis, determination of the metastatic state, and tumor management. Based on the presence or absence of the immunohistochemical markers, breast tumors can be classified as ER-positive tumors, PR-positive tumors, HER2-positive tumors, triple positive, and triple negative breast cancer (TNBC).

TNBC tumors do not express three key therapeutically relevant cell-surface receptors: estrogen receptor (ER), progesterone receptor (PR), and overexpression of the human epidermal growth factor receptor 2 (Her2/ERBB2). The lack of these receptors significantly decreases the likelihood of successful treatment as most currently approved breast cancer treatments mainly target ER, PR, or HER2 positive tumors. Furthermore, TNBC tumors have unique clinical, molecular, and pathological characteristics, and have higher relapse rates and a worse prognosis compared to non-TNBC tumors. TNBC accounts for about 15-20% of all breast cancers and disproportionately affects African-American, Hispanic, and premenopausal women. TNBC is three times more common in African-American women compared to Caucasian women and is more likely to recur. One of the primary molecular characteristics of TNBC tumors is that they arise from mutations in the BRCA1 gene, which plays a critical role in double-stranded DNA repair and leads to DNA stability and tumor resistance. Moreover, because of its poor prognosis and higher relapse rates, less than 30% of women with metastatic TNBC survive up to 5 years following diagnosis.

Currently there are no targeted treatments for TNBC, and it has been reported that defects in the apoptotic machinery is one of the numerous well-established mechanisms of drug resistance in cancer patients, including patients with TNBC. The most frequently used treatment regimen for TNBC is surgery, with adjuvant chemotherapy and radiation therapy, which is ineffective once the tumor has spread to other organs. The majority of TNBC patients initially respond to therapy; however, patients with residual TNBC disease eventually relapse and have a worse prognosis. Numerous targeted therapies alone or in combination with other drugs have shown limited benefit in aggressive and heterogeneous TNBC disease, resulting in poor survival rate. A limitation of some of the clinically available drugs used in the treatment of breast cancer is that their anticancer efficacy results from damaging DNA and triggering the intrinsic apoptotic pathway. However, because TNBC cells contain mutations in tumor suppressor genes (e.g., PTEN, p53), they are relatively resistant to apoptotic stimuli. TNBC cells can also develop resistance to drugs by augmenting the repair of DNA lesions and overexpressing efflux transporters. This type of resistance is prominent in putative stem cells, which may underlie the recurrence of TNBC. Once a TNBC tumor become resistant to chemotherapy, metastasis occurs, which then reduces patient survival time to less than one year. Moreover, other therapies can also become ineffective due to defects in apoptosis pathways. Currently, there is an urgent need to develop new chemotherapeutic compounds that induce non-apoptotic cell death to surmount the resistance of TNBC cells to compounds that induce apoptosis.

Proapoptotic chemotherapy comprising non-specific & targeted chemotherapeutic agents is the mainstay for the treatment for several cancers, but clinical effectiveness of this therapy is seriously limited by development of drug resistance. Apoptosis dysfunction appears to be a critical factor in intrinsic and acquired chemotherapy drug resistance. Targeting cell death pathways other than apoptosis is a therapeutic avenue for treatment of apoptosis resistant cancers.

Necroptosis has been identified as a non-apoptotic form of programmed cell death. As necroptosis is a cell death pathway distinct from apoptosis, necroptotic inducers, due to their distinct mechanism of action from current chemotherapeutic agents, can be considered a new class of anticancer agents possibly capable of treating apoptotic resistant or MDR cancers. Unlike the conventional anticancer drugs that activate apoptosis and simultaneously elicit the anti-apoptotic progression, necroptotic inducers activate a cell death without "touching" the most "elusive" and highly organized drug-resistance system in cancers ever uncovered. Furthermore, induction of necroptosis in tumors promotes beneficial anti-tumor immune responses that are prevented when tumor cells die by apoptosis.

Despite realization of clinical potential of necroptosis induces for apoptotic resistant & MDR cancers, development of anticancer drugs for therapeutic exploitation of necroptosis for cancer therapy is not particularly forthcoming. This is because the molecular mechanisms that regulate necroptosis are still poorly understood, and the necroptotic signalling networks that can yield tractable targets are not well delineated as in the case of apoptosis. Thus, there is a need in the art for the development of anticancer drugs.

SUMMARY

Provided is a method of inducing cell death, the method comprising administering to a cell an effective amount of a compound to induce death of the cell, wherein the compound comprises one of Formulas I-VII:

Formula I

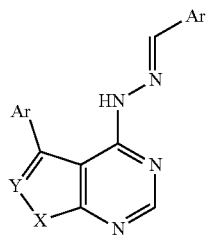

wherein X is S, O, or NH, Y is CH or N, and each Ar is independently aryl or heteroaryl with or without substituents; or Formula II wherein X is S, O, or NH, Y is CH or N, and Ar is aryl or heteroaryl with or without substituents, and R is an alkyl, alkyl amino, alkoxy, halogen, nitro, or cyano substituent;

Formula III

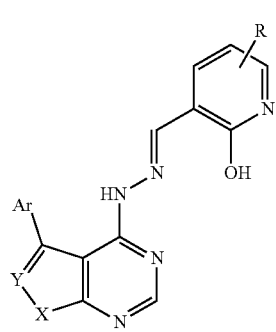

wherein X is S, O, or NH, Y is CH or N, Ar is aryl or heteroaryl with or without substituents, and R is an alkyl, alkyl amino, alkoxy, halogen, nitro, or cyano substituent;

Formula IV

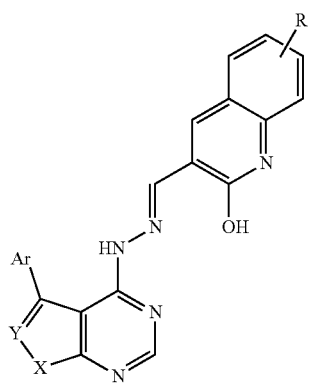

wherein X is S, O, or NH, Y is CH or N, Ar is aryl or heteroaryl with or without substituents, and R is an alkyl, alkyl amino, alkoxy, halogen, nitro, or cyano substituent;

Formula V wherein X is S, O, or NH, Y is CH or N, Ar is aryl or heteroaryl with or without substituents, and R is an alkyl, alkyl amino, alkoxy, halogen, nitro, cyano substituent;

Formula VI wherein X is S, O, or NH, Y is CH or N, Ar is aryl or heteroaryl with or without substituents, and R is an alkyl, alkyl amino, alkoxy, halogen, nitro, or cyano substituent; or

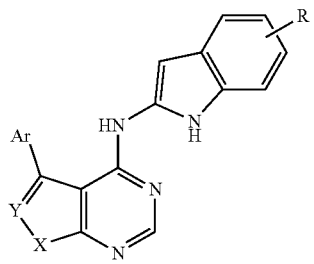

Formula VII wherein X is S, O, or NH, Y is CH or N, Ar is aryl or heteroaryl with or without substituents, and R is an alkyl, alkyl amino, alkoxy, halogen, nitro, or cyano substituent; or a salt, stereoisomer, tautomers, racemate, hydrate, polymorph, or prodrug of any of Formulas I-VII.

In certain embodiments, the compound comprises TPH104:

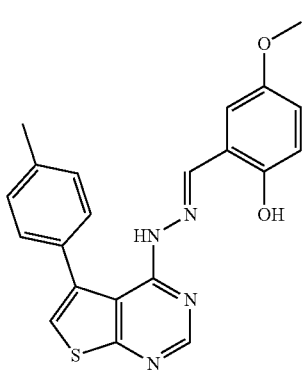

TPH104

In certain embodiments, the compound comprises TPH104a:

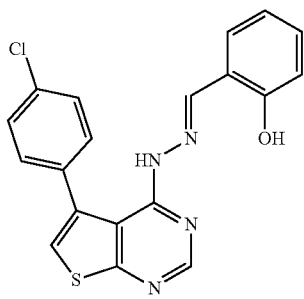

TPH104a

In certain embodiments, the compound comprises TPH104b:

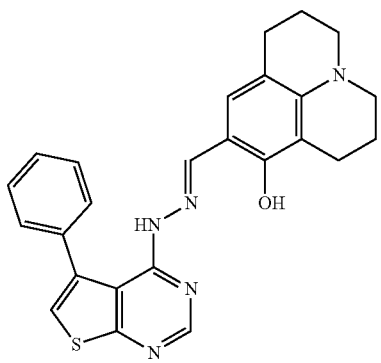

TPH104b

In certain embodiments, the compound comprises TPH104c:

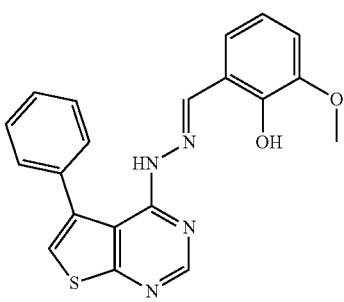

TPH104c

In certain embodiments, the compound comprises TPH104d:

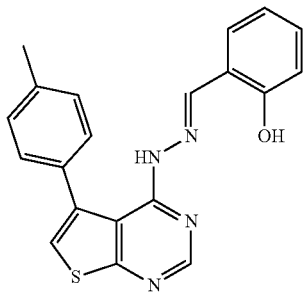

TPH104d

In certain embodiments, the compound comprises TPH104e:

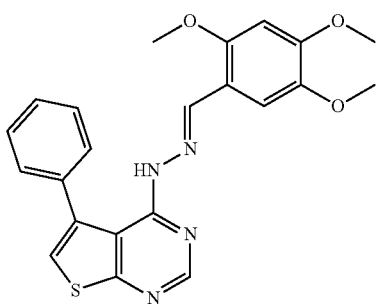

In certain embodiments, the compound comprises TPH104f:

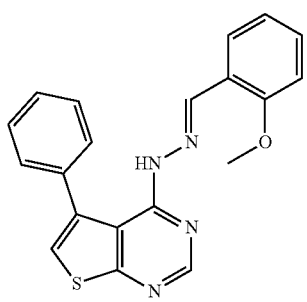

In certain embodiments, the compound comprises TPH104g:

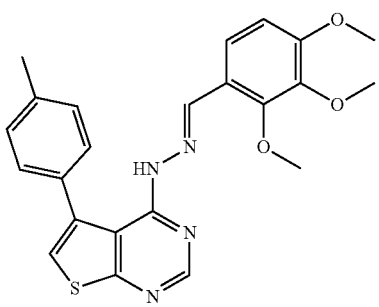

In certain embodiments, the compound comprises TPH104h:

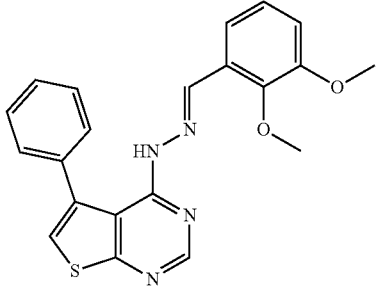

In certain embodiments, the compound comprises TPH104i:

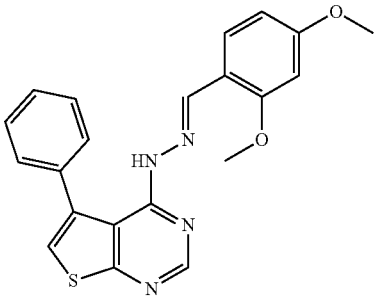

In certain embodiments, the compound comprises TPH104j:

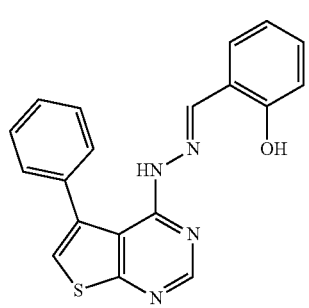

In certain embodiments, the compound comprises TPH104k:

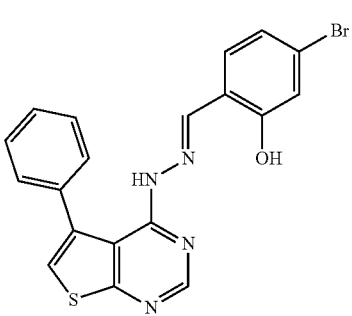

In certain embodiments, the compound comprises TPH104l:

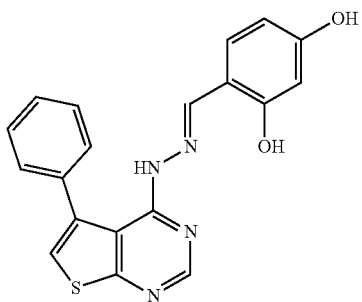
TPH104l

In certain embodiments, the compound comprises TPH104m:

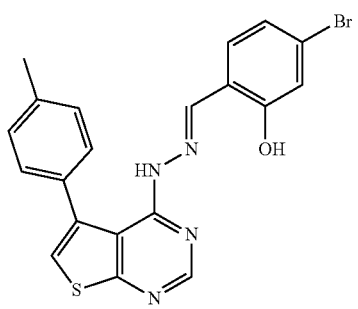
TPH104m

In certain embodiments, the compound comprises TPH104n:

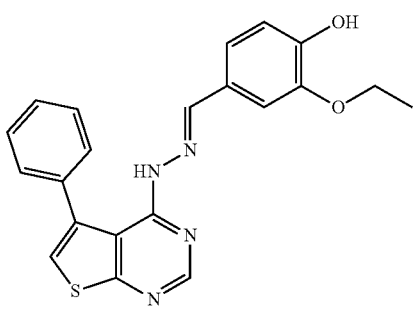
TPH104n

In certain embodiments, the compound comprises TPH104o:

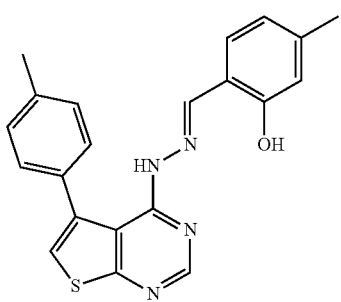
TPH104o

In certain embodiments, the compound comprises TPH104p:

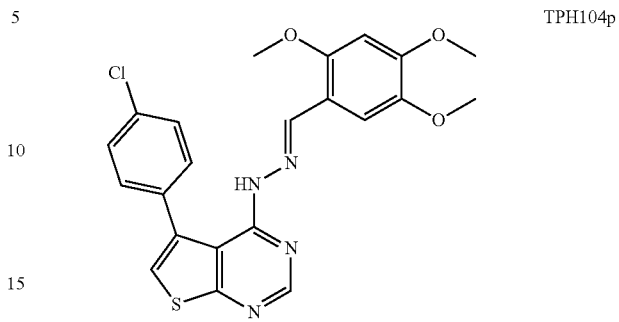
TPH104p

In certain embodiments, the compound comprises TPH104q:

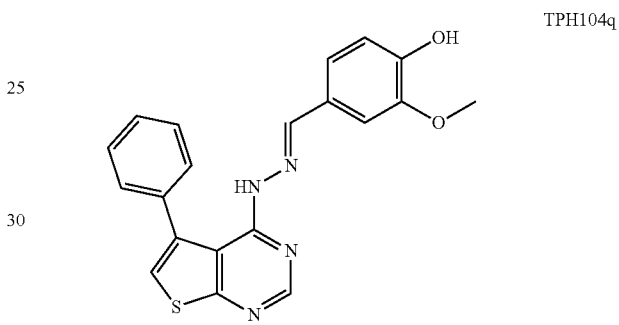
TPH104q

In certain embodiments, the cell is a cancer cell. In particular embodiments, the cancer is triple negative breast cancer, colon cancer, prostate cancer, ovarian cancer, or lung cancer.

Further provided is a method of treating a cancer, the method comprising administering to a subject having a cancer an effective amount of a compound of Formulas I-VII, or a salt, stereoisomer, racemate, hydrate, polymorph, or prodrug of Formulas I-VII, and treating the cancer in the patient. In certain embodiments, the subject has triple negative breast cancer, colon cancer, prostate cancer, ovarian cancer, or lung cancer. In certain embodiments, the compound inhibits proliferation of the cancer by inducing necroptosis and inhibiting autophagy.

Further provided is a method of inhibiting triple negative breast cancer, the method comprising treating a subject having triple negative breast cancer with, or administering to a triple negative breast cancer cell, an effective amount of a thieno[2,3-d]pyrimidine, and inhibiting the triple negative breast cancer. In certain embodiments, the thieno[2,3-d] pyrimidine induces selective necroptotic cell death in triple negative breast cancer over normal cells. In certain embodiments, the thieno[2,3-d]pyrimidine has a hydroxyl group on the C2-position of an aryl ring linked to a hydrazine moiety. In certain embodiments, the thieno[2,3-d]pyrimidine comprises a substitution at the C3, C4, or C5 position on an aryl ring. In certain embodiments, the thieno[2,3-d]pyrimidine comprises a methyl or chloro substitution on the C4-position of an aryl ring.

Further provided is a method of modulating of modulating apoptosis and autophagy in TNBC cells, the method comprising contacting TNBC cells with an effective amount of a compound and modulating apoptosis and autophagy in the TNBC cells, wherein the compound comprises a compound of Formulas I-VII. In certain embodiments, the compound comprises TPH104:

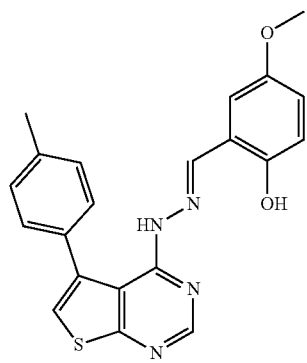
TPH104

Further provided is a method of modulating the ABCG2 transporter, the method comprising contacting cells with an effective amount of a compound and modulating the ABCG2 transporter in the cells, wherein the compound comprises a compound of Formulas I-VII. In certain embodiments, the compound comprises TPH104:

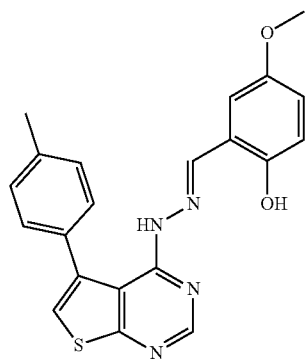
TPH104

Further provided is a method of of upregulating a necroptotic marker in a cell, the method comprising contacting a cell with an effective amount of a compound and upregulating a necroptotic marker in the cell, wherein the compound comprises a compound of Formulas I-VII. In certain embodiments, the compound comprises TPH104:

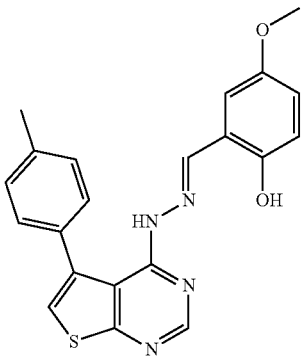
TPH104

In certain embodiments, the cell is a breast cancer cell.

Further provided is a method of upregulating expression of TRAIL or DR5 in a cell, the method comprising contact a cell with an effective amount of a compound and upregulating expression of TRAIL or DR5 in the cell, wherein the compound comprises a compound of Formulas I-VII. In certain embodiments, the compound comprises TPH104:

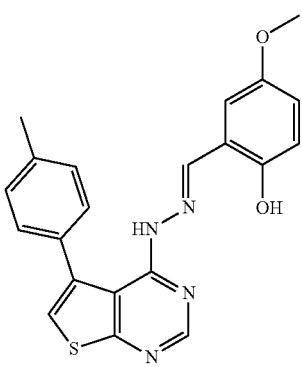
TPH104

In certain embodiments, the cell is a breast cancer cell.

Further provided is a method for inhibiting ABCB1 and ABCG2 efflux functions, the method comprising contacting a cell with an effective amount of a compound and inhibiting ABCB1 and ABCG2 efflux functions in the cell, wherein the compound comprises a compound of Formulas I-VII. In certain embodiments, the compound comprises TPH104 or TPH104m.

Further provided is the use of a compound of Formulas I-VII as a probe to understand cell biology or cell cancer.

Further provided is the use of a compound of Formulas I-VII as a chemoadjuvant in combination with other anti-cancer agents used in the treatment of triple negative breast cancer, colon cancer, prostate cancer, ovarian cancer, or lung cancer.

BRIEF DESCRIPTION OF THE DRAWINGS

FIG. 2A shows TNBC cell lines (MDA-MB231, MDA-MB468, and BT-20) compared to the non-TNBC cell lines (ZR-75-1 and MCF-7), and FIG. 2B shows shows the cell survival curve for TNBC vs. non- TNBC cell lines. p<0.01, *p<0.001 compared to the control. The IC$_{50}$ values shown in this table represent the mean±SD of three independent MTT experiments, each performed in triplicate.

FIG. 3A show the effect of TPH104 on MDA-MB231, MDA-MB468, and BT-20 cells, based on the whole wells, the colony density and individual colony size. FIGS. 3B-3D show bar graphs summarizing the results for the colony formation rate of MDA-MB-231, MDA-MB468, and BT-20 cell lines, respectively. The results represent the means±SD of three independent experiments. p<0.01, *p<0.001, ****p<0.0001 compared to the control.

FIGS. 5A and 5B illustrate the effect of TPH104 on the distribution of the cells in the different cell cycle phases in MDA-MB468 and MDA-MB231, respectively. The bar graphs (FIGS. 5C and 5D) represent a summary of the change in the % cell accumulation in each phase of the cell cycle in both cell lines. The data represent the mean±SD of four independent experiments performed in triplicate. *p<0.001, **p<0.0001 compared to the control.

FIG. 6A shows the results of four independent flow cytometry experiments for BT-20 and MDA-MB468 cells incubated with 0, 0.5, 1, or 2 μM of TPH104. FIG. 6B shows bar graphs representing the quantification of the results. The data represent the means±SD of four independent experiments.

FIG. 8B shows confocal microscopy images (60×) of BT-20 cells line indicating that incubation with TPH104 (1, 2, or 5 μM) for 12 h does not induce nuclear condensation.

FIG. 9B shows a bar graph depicting the IC$_{50}$+SD values and the significance of the combination of z-VAD-fmk and TPH104 in MDA-MB468 TNBC cells.

FIGS. 10B-10C show histograms summarizing the Western blots densitometric analysis using Image J software (R=relative expression compared to). The results represent the means±SEM of 3 independent experiments. *p<0.05, p<0.01, *p<0.001, ****p<0.0001 compared to the control group.

FIG. 11A shows the levels of H2DCFDA fluorescence after incubation in both MDA-MB468 and BT-20 TNBC cells, respectively. The images were taken by an EVOS-FLC digital fluorescent microscope at 40×. FIG. 11B shows a bar graph representing the relative (R) fluorescence of H2DCFDA in cells incubated with TPH104 compared to controls. Cells were incubated with paclitaxel (PAC, 2 μM) for 1-2 h as a positive control. The experiments were repeated three times for each cell line. ***p<0.001 compared to the control.

FIG. 12A shows representative images of the cells in the transwell assay that have migrated after incubation with TPH104 (0, 0.1, 1, and 10 μM). FIG. 12B shows histograms indicating the number of cells that have migrated and invaded the membrane inserts (counted/field of image) for MDA-MB468 and BT-20, respectively. *p<0.05, p<0.01, *p<0.0004, compared to the control group.

FIG. 13A shows representative images showing the wound area and closure at different time points (0, 12, 24, and 36 h) after incubation with TPH104 (0, 0.5, 1, 2, 5, and 10 μM). FIG. 13B shows confocal images of RAW264.7 cells expressing blue opsin-mCherry. Control cells were incubated with 11-cis retinal (50 μM) for 5 minutes in the dark. A confined optical input of 445 nm was placed in-front of cells using a user-defined region of interest (ROI) and optically activated (OA) continuously in the direction of cell migration pathway for 20 minutes (OA=blue box). Cells were incubated with 10 μM of TPH104 for 30 minutes, followed by incubation with 11-cis retinal (50 μM) for 5 minutes in the dark. Scale=5 μm.

FIGS. 14B-14C shows histograms quantitatively summarizing the results for BT-20 cells where (R) is for relative. The data represent the means±SEM of three independent experiments. *p<0.05, p<0.01, *p<0.001 compared to the control.

FIG. 15B shows a bar graph depicting the IC$_{50}$+SD values and the significance of the combination of different Nec-1 concentrations and TPH104 in MDA-MB468 TNBC cells; where Nec-1=Necrostatin-1. *p<0.05, p<0.01, *p<0.001 compared to the control.

FIG. 16B shows histograms quantitatively summarizing the results for each cell line where (R)

is for relative, casp is for caspase8 and clvd is for cleaved. The data are presented as the means±SEM of three independent experiments. *p<0.05, p<0.01, *p<0.001.

Figure 17A:
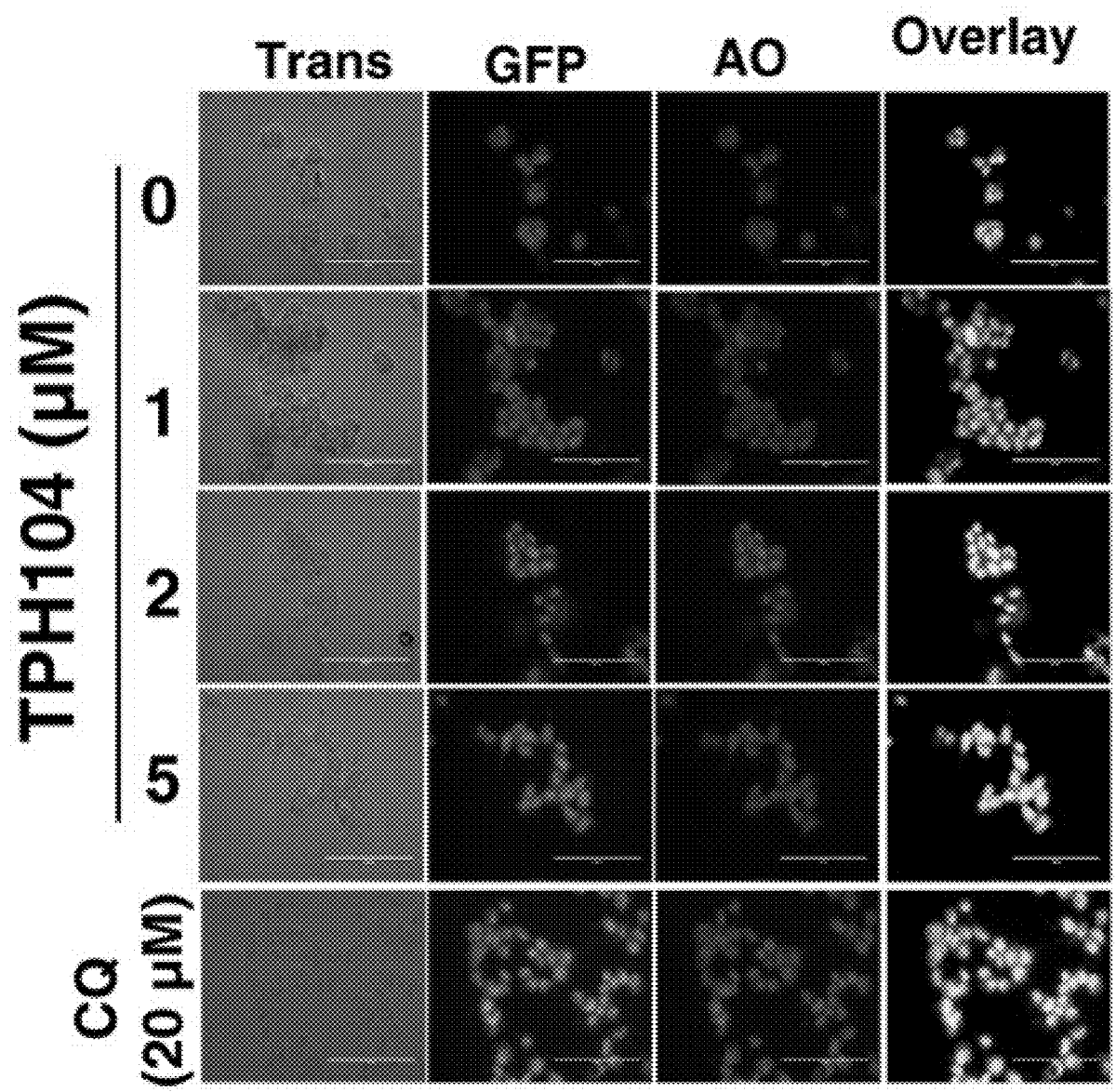
Figure 17B:
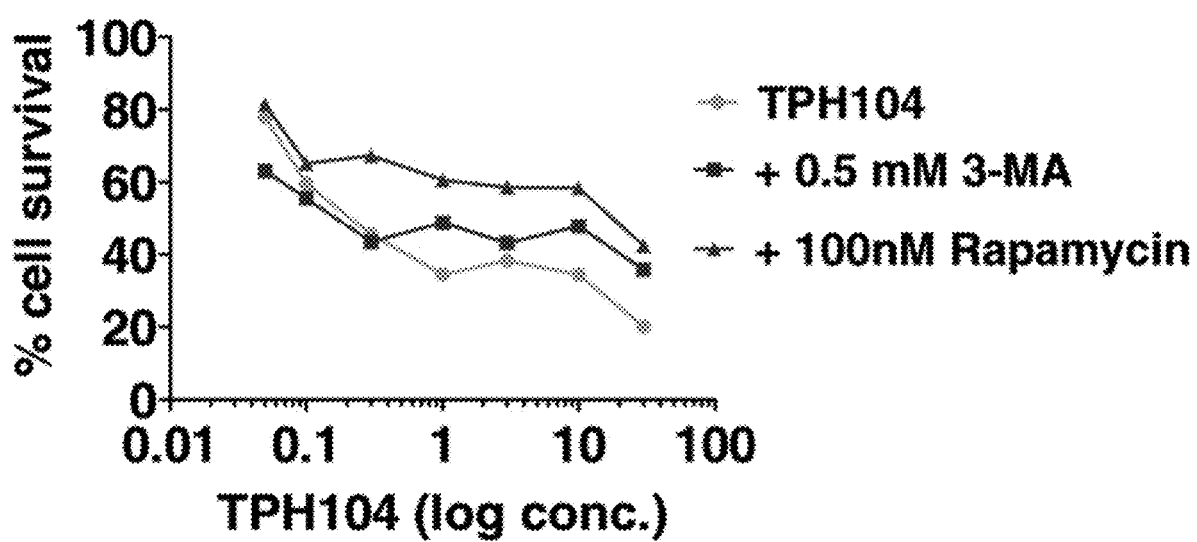

FIGS. 17A-17B: The incubation of BT-20 cells with TPH104 (0, 1, 2, or 5 µM) for 12 h did not significantly increase the fluorescence of acridine orange, whose increase in fluorescence indicated presence of autophagic cell death (FIG. 17A). The images were taken by an EVOS-FLc digital fluorescent microscope at 40×, where AO represents acridine orange. Also shown are BT20 TNBC cells incubated with 20 µM of chloroquine for 12 h. FIG. 17B shows the cell survival curve of BT-20 TNBC cells treated with TPH104 alone or in combination with 0.5 mm 3-MA, an autophagy inhibitor, or 100 nM rapamycin, an autophagy inducer; where 3-MA is 3-methyladenine.

Figure 18A:
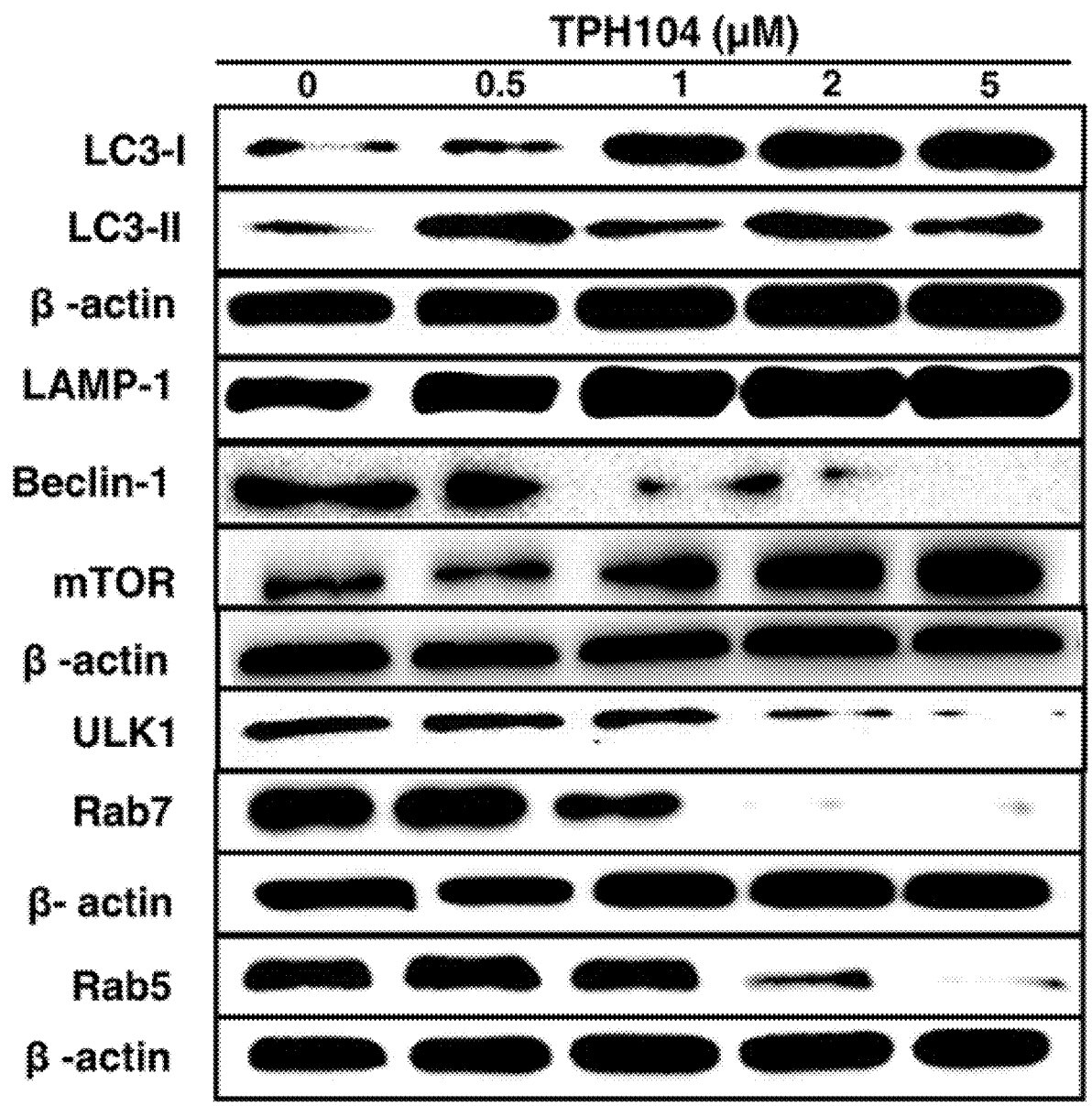
Figure 18B:
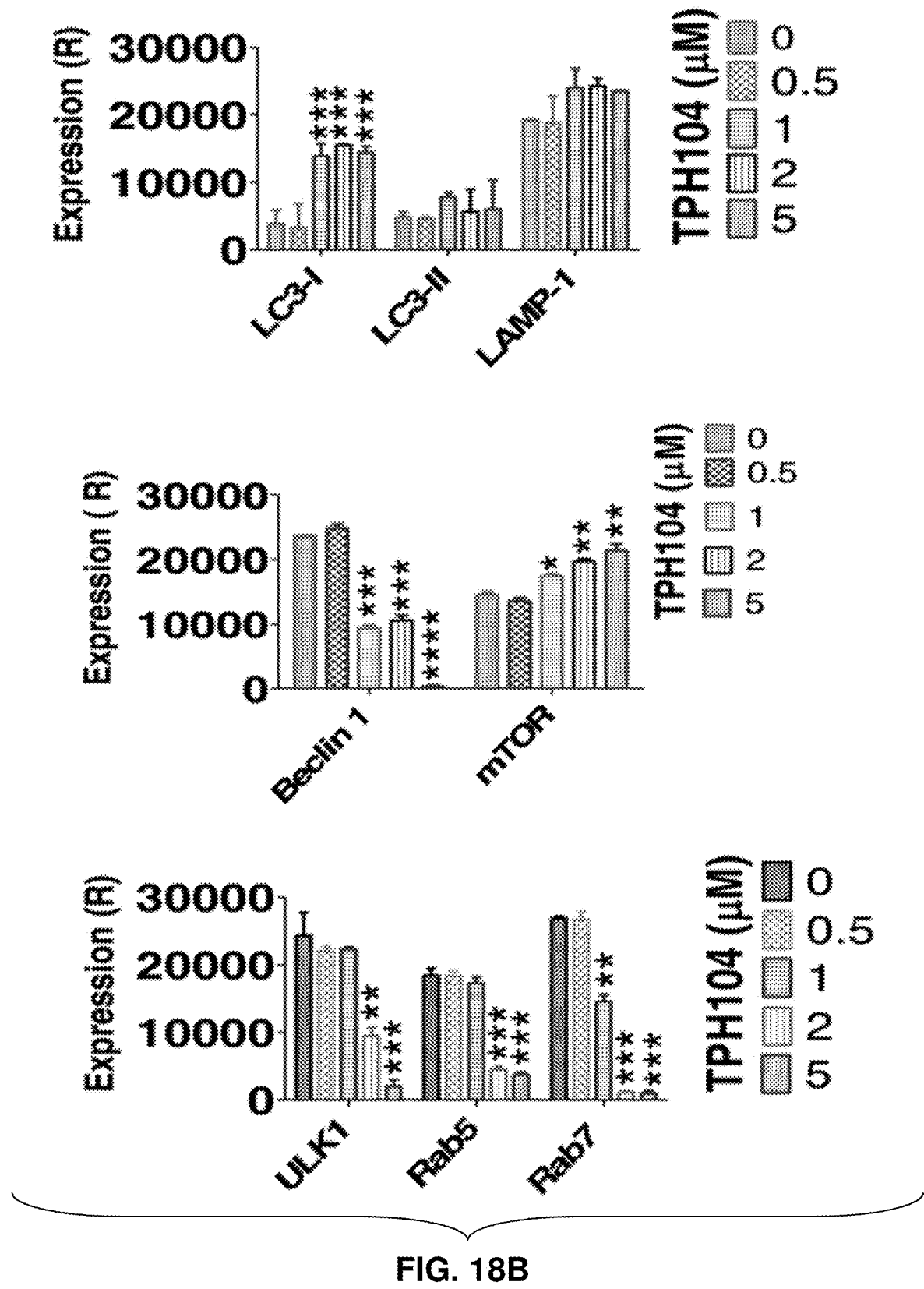

FIGS. 18A-18B: Western blot analysis of LC3B-I, LC3B-II, LAMP1, Beclin-1, mTOR, ULK1, Rab7, and Rab5 in BT-20 TNBC cells (FIG. 18A). β-actin levels were used to normalize the blots. FIG. 18B shows histograms quantitatively summarizing the results for each cell line where (R) represents relative expression compared to β-actin. The data represent the means±SEM of three independent experiments. *p<0.05, p<0.01, *p<0.001 compared to the control.

Figure 19A:
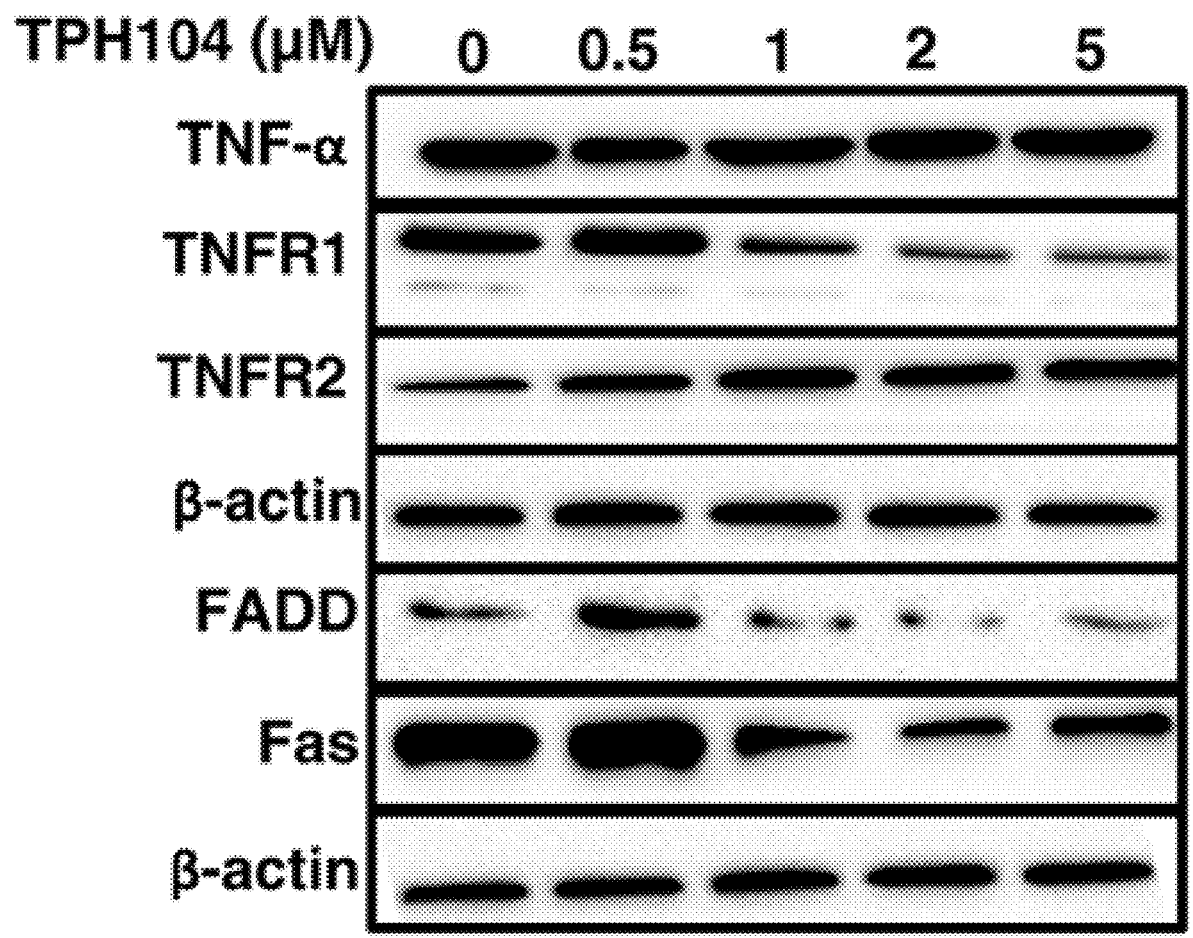
Figure 19B:
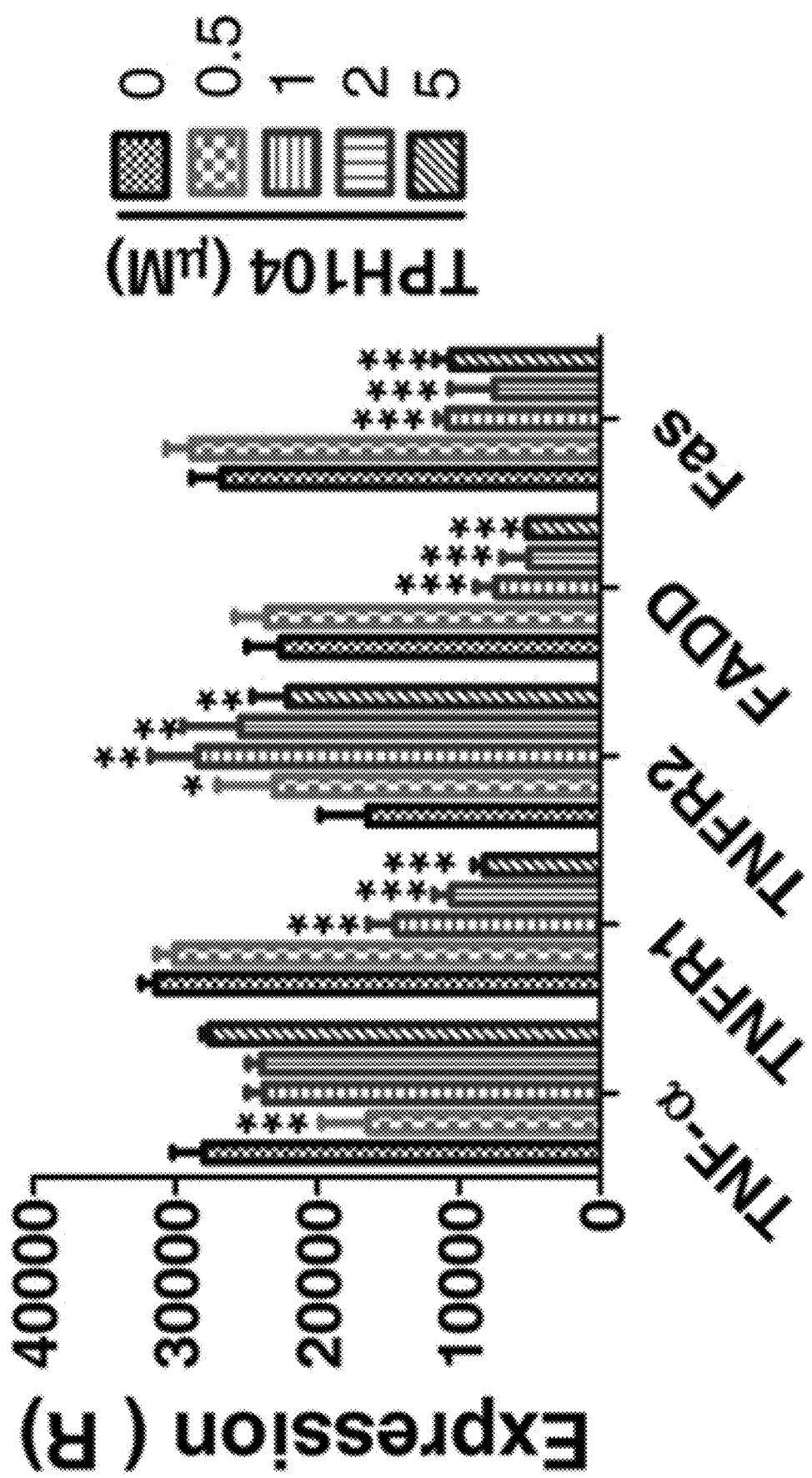

FIGS. 19A-19B: Western blot analysis for the expression of TNF-α, TNFR1, TNFR2, FADD, and Fas (FIG. 19A). BT-20 TNBC cells were incubated with (0, 0.5, 1, 2, and 5 µM) of TPH104; β-actin levels were used to normalize cytosolic proteins. FIG. 19B shows histograms quantitatively summarizing the western blot results where (R) is for relative. The data are presented as the means±SEM of three independent experiments. *p<0.05, p<0.01, *p<0.001.

Figure 20A:
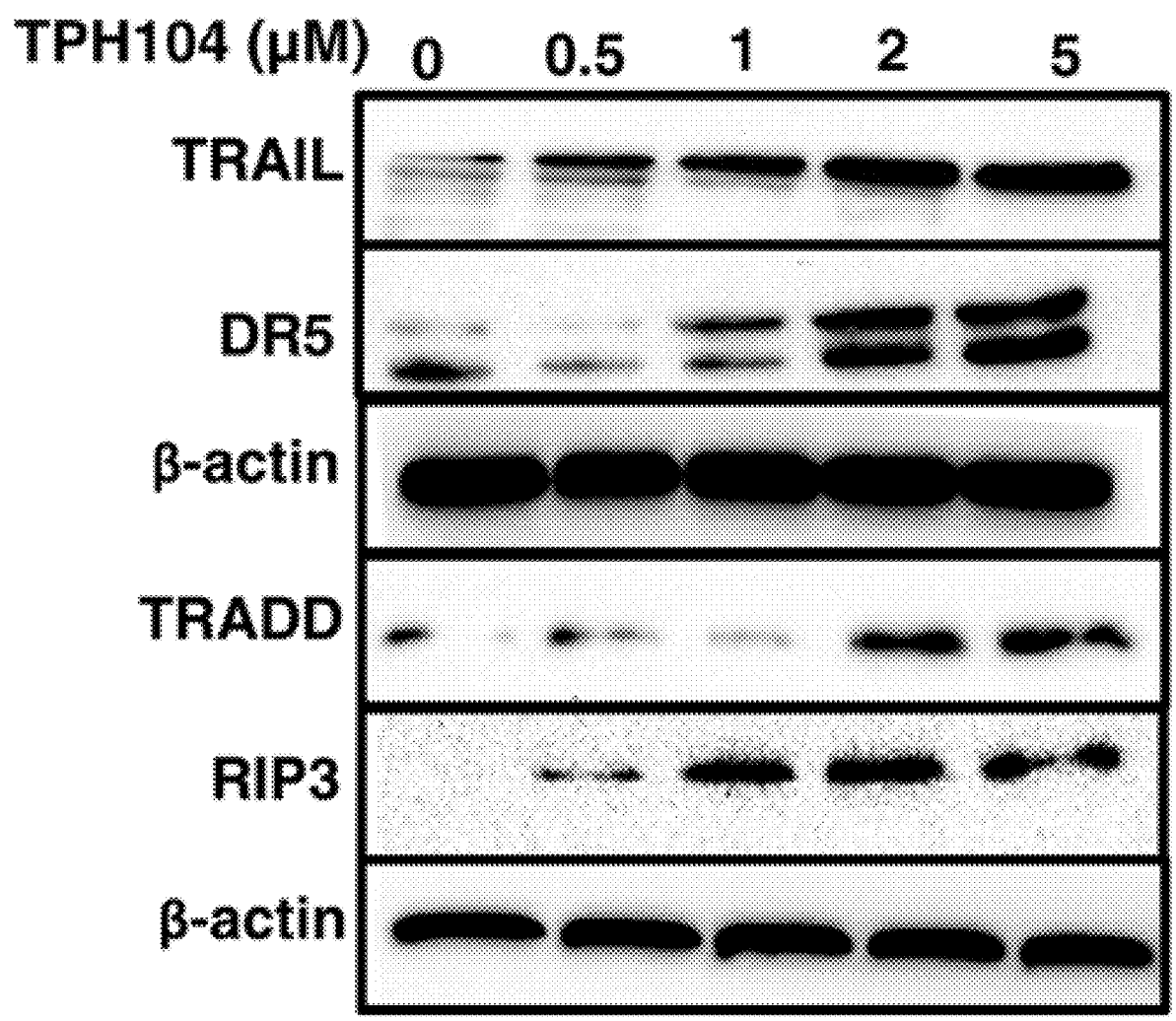
Figure 20B:
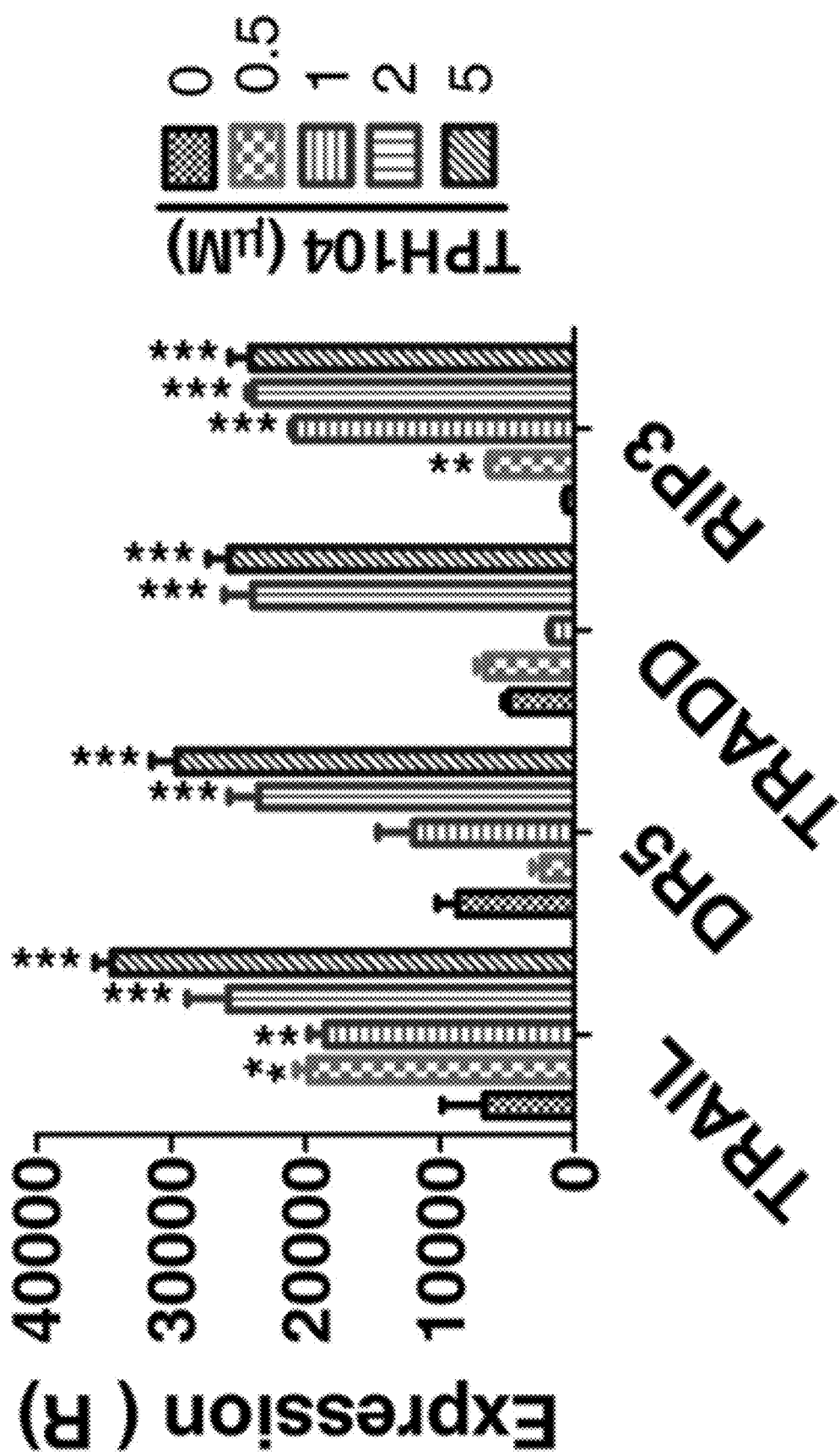
Figure 20C:
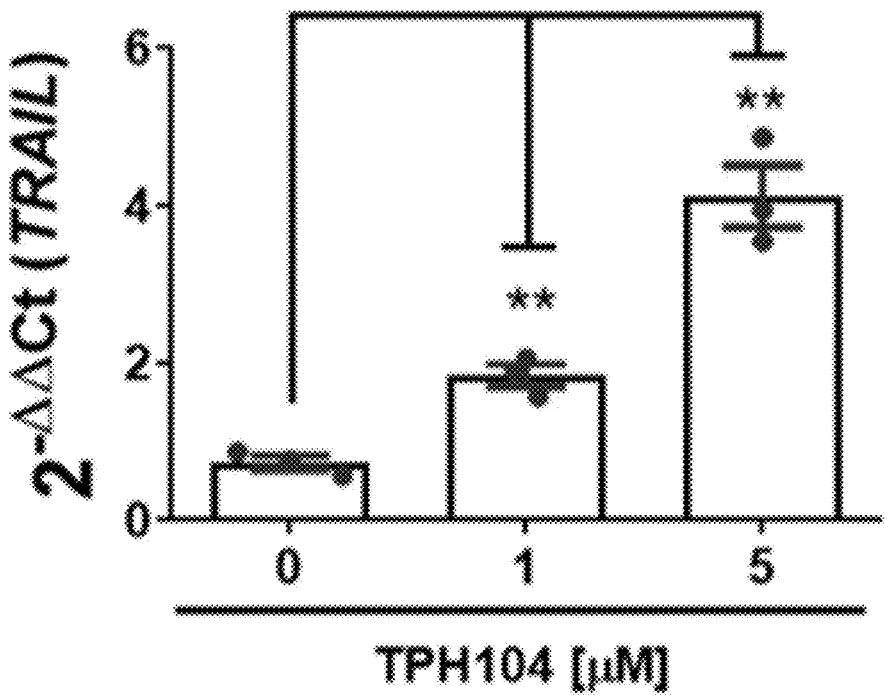
Figure 20D:
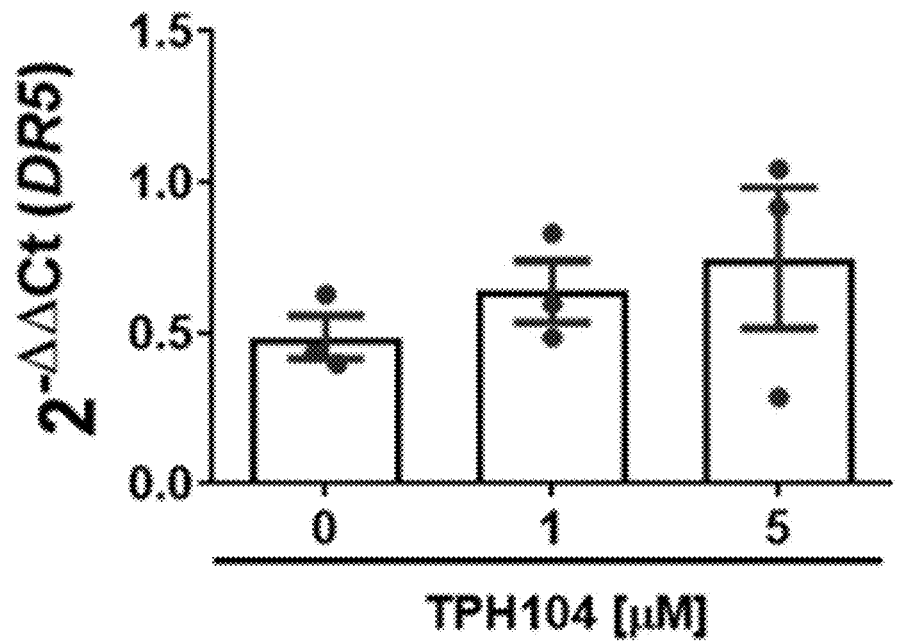

FIGS. 20A-20D: Western blot analysis for the expression of TRAIL, DR5, TRADD, and RIP3 (FIG. 20A). BT-20 TNBC cells were incubated with (0, 0.5, 1, 2, and 5 µM) of TPH104; β-actin levels were used to normalize cytosolic proteins. FIG. 20B shows histograms quantitatively summarizing the western blot results where (R) is for relative. The data are presented as the means±SEM of three independent experiments. *p<0.05, p<0.01, *p<0.001. FIGS. 20C-20D show average fold change of mRNA levels of TRAIL1, DR5 in TPH104 treated BT-20 cells relative to untreated vehicle control cells. *, P<0.05; **, P<0.01; one-way ANOVA, followed by Tukey's post-hoc. n=3 independent experiments.

Figure 21:
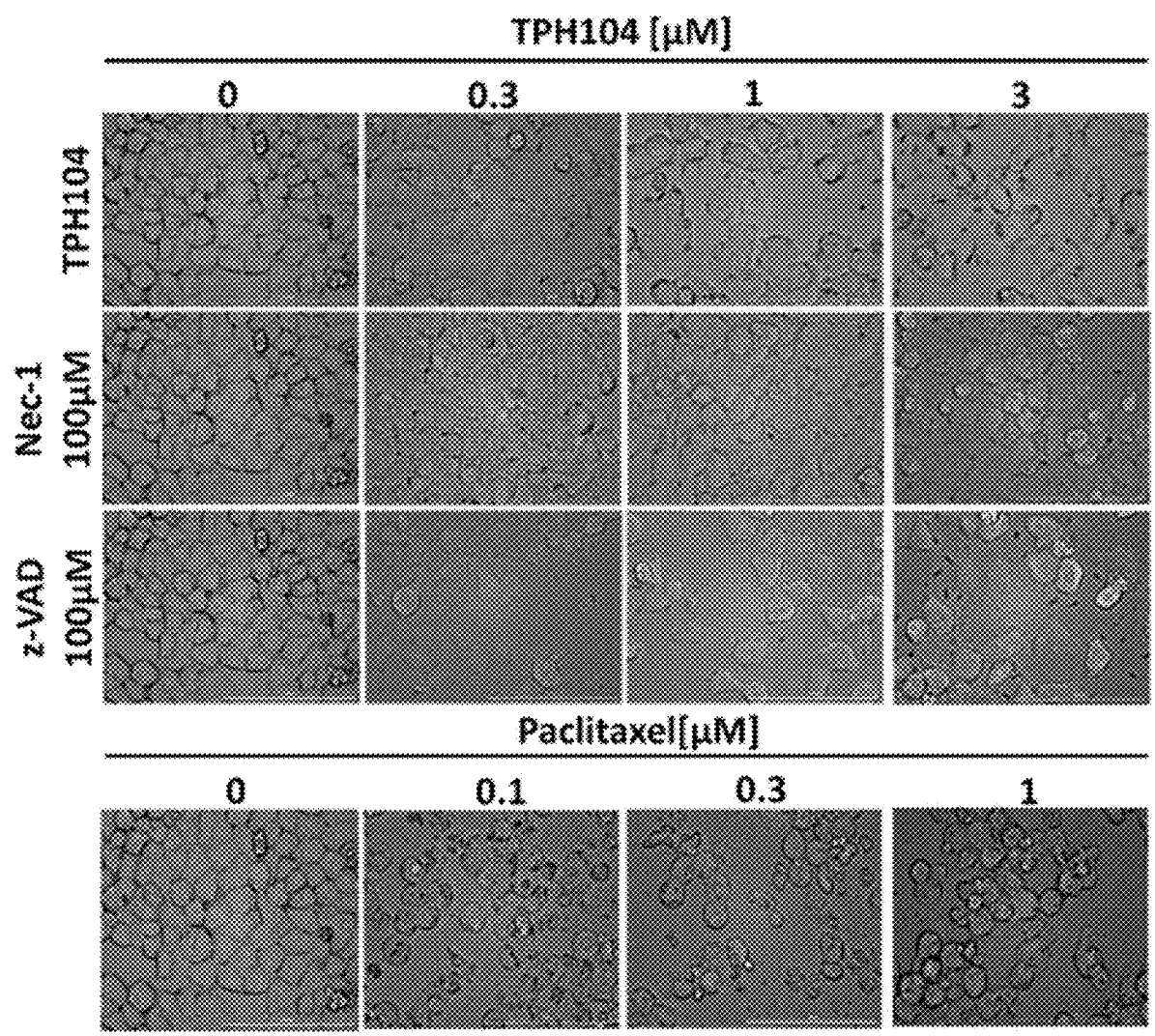

FIG. 21: TPH104 induces necroptotic cell death in TNBC cells. Representative images of morphological changes in BT-20 cells (40×) after treatment with either TPH104 alone or in combination with 100 µM of Necrostatin-1 (Nec-1) or z-VAD-fmk for 3 hours or with Paclitaxel 1 hour. Scale bars: 100 µm.

Figure 22:
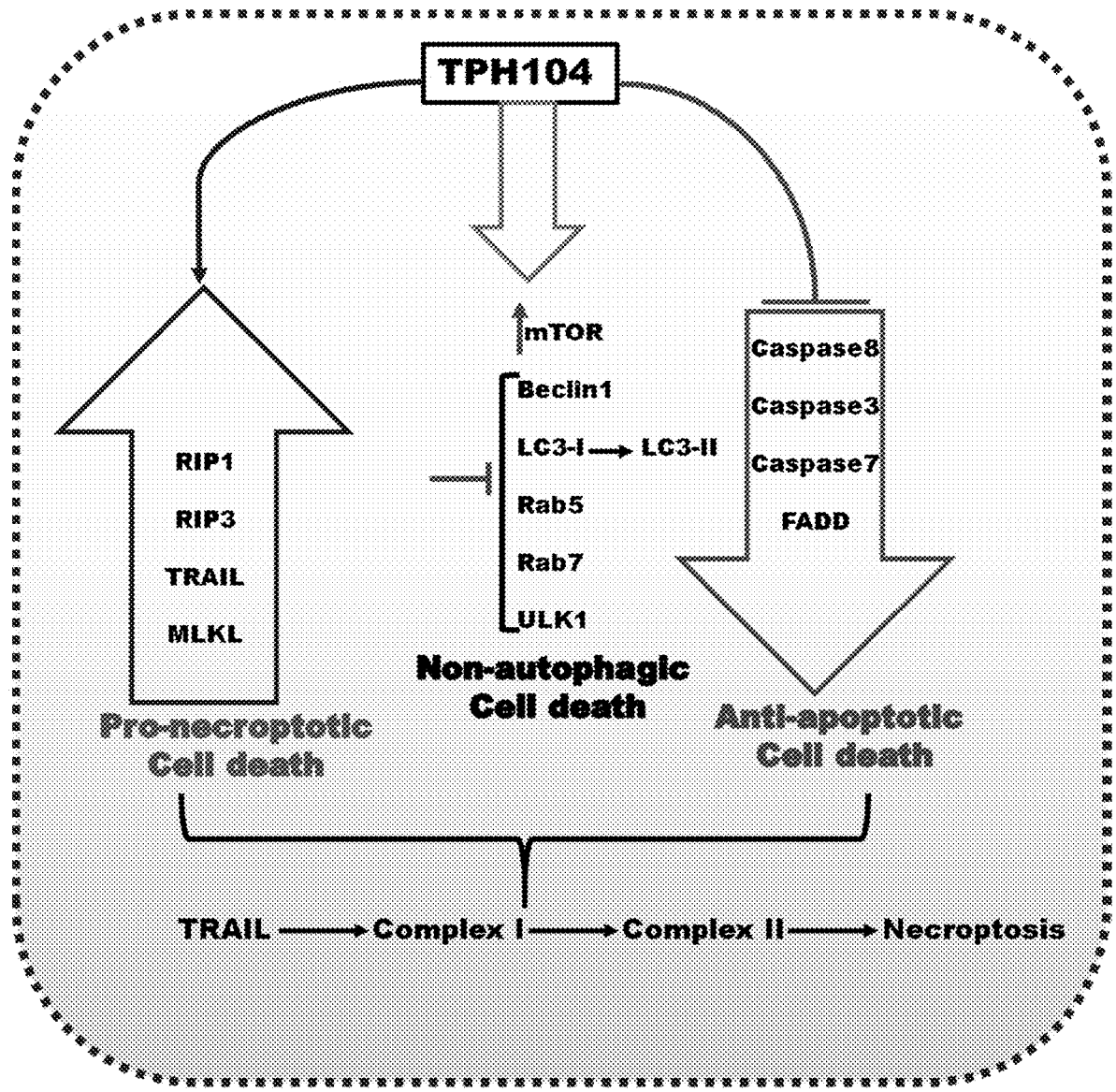

FIG. 22: Schematic diagram showing how TPH104-trigger and sustain necroptotic pathway in TNBC cells. Treatment of TPH104 triggers the expression of kinases in the necroptotic pathway with concomitant inhibition or no effect on caspases relevant in the apoptotic pathway. Increased expression of TRAIL and DR5 drive the necroptotic pathway in a feed forward manner by inhibition of caspase 8 needed to initiate apoptosis by degrading RIPK1. Modulation of autophagy markers further strengthen necroptotic pathway ensued in BT-20 cells.

Figure 23A:
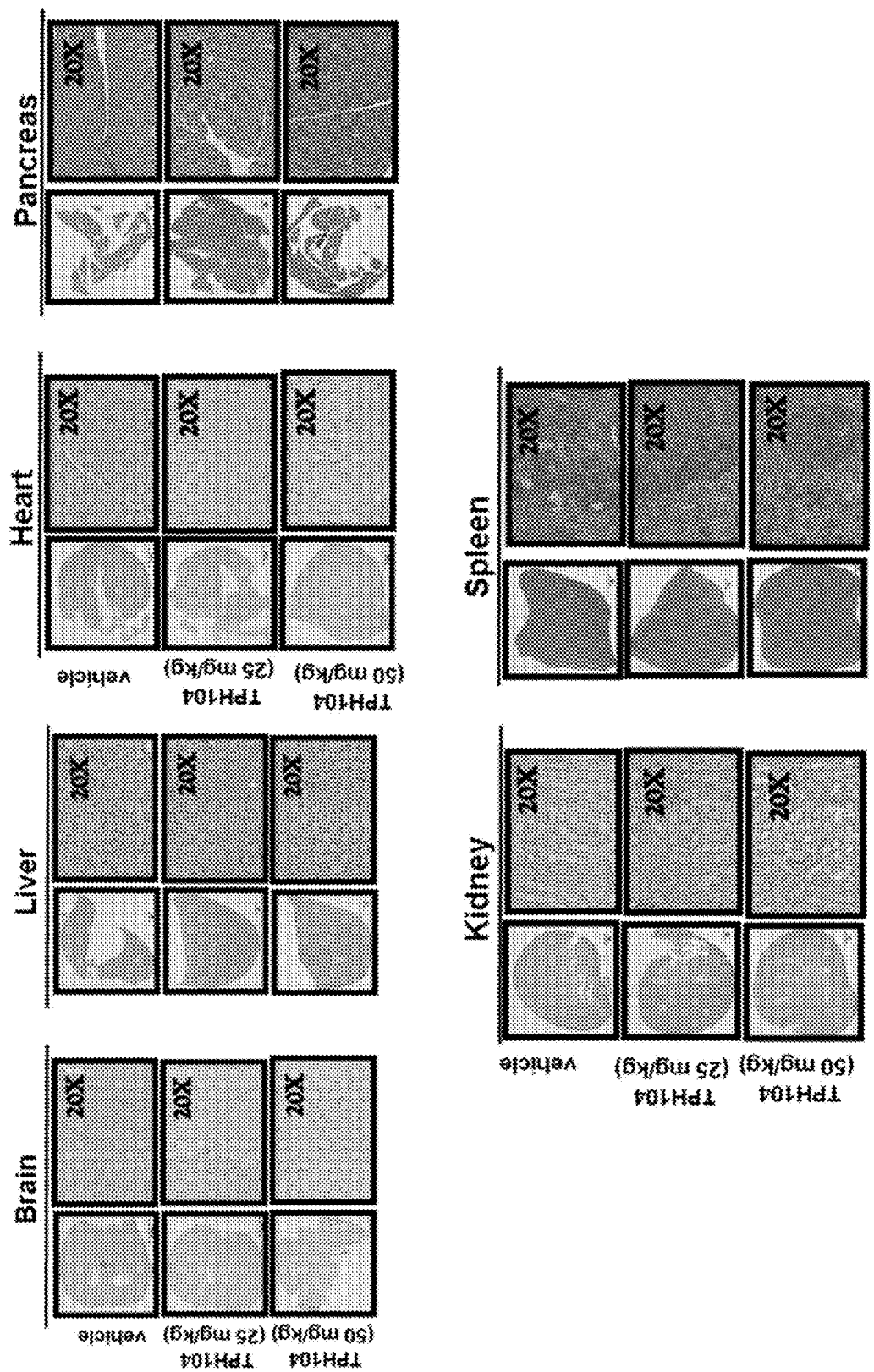
Figure 23B:
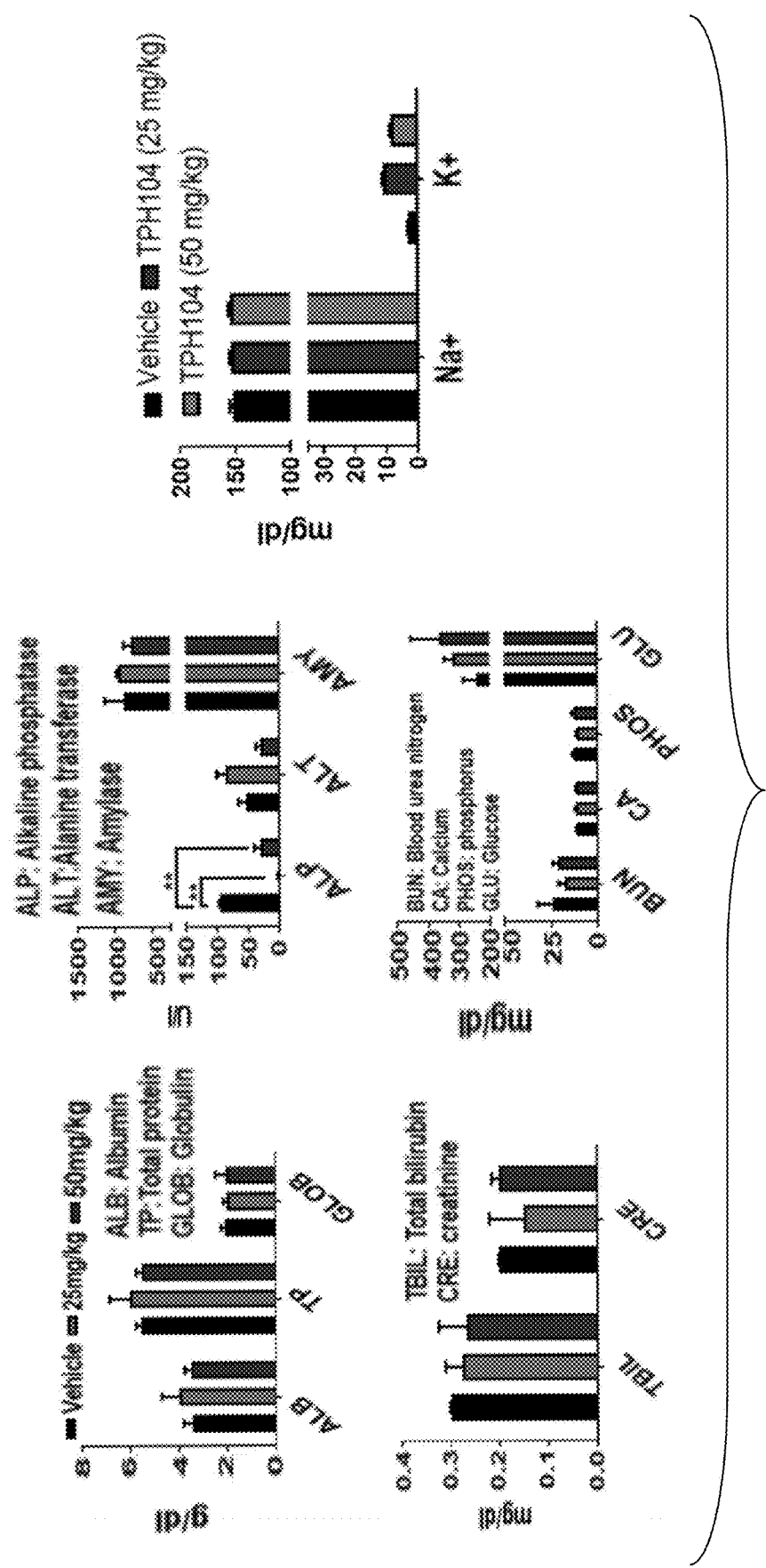
Figure 23C:
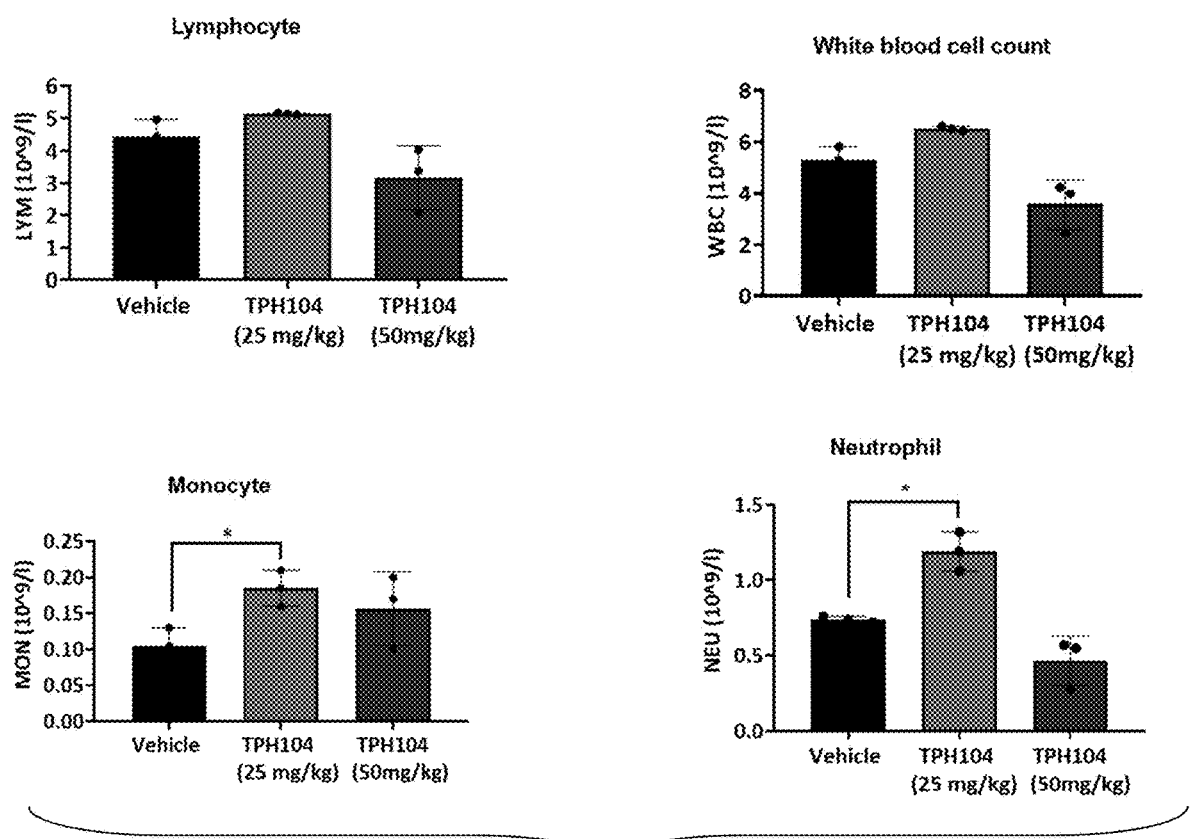
Figure 23D:
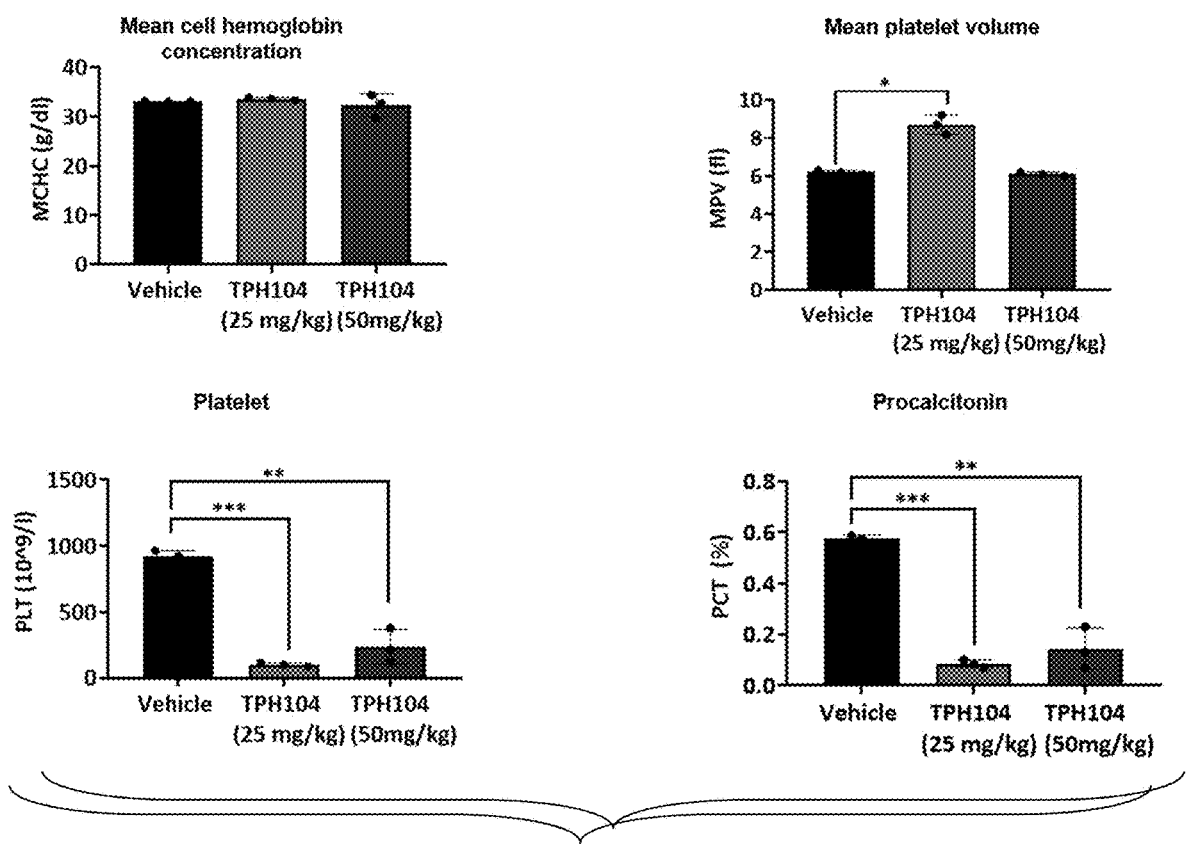
Figure 23E:
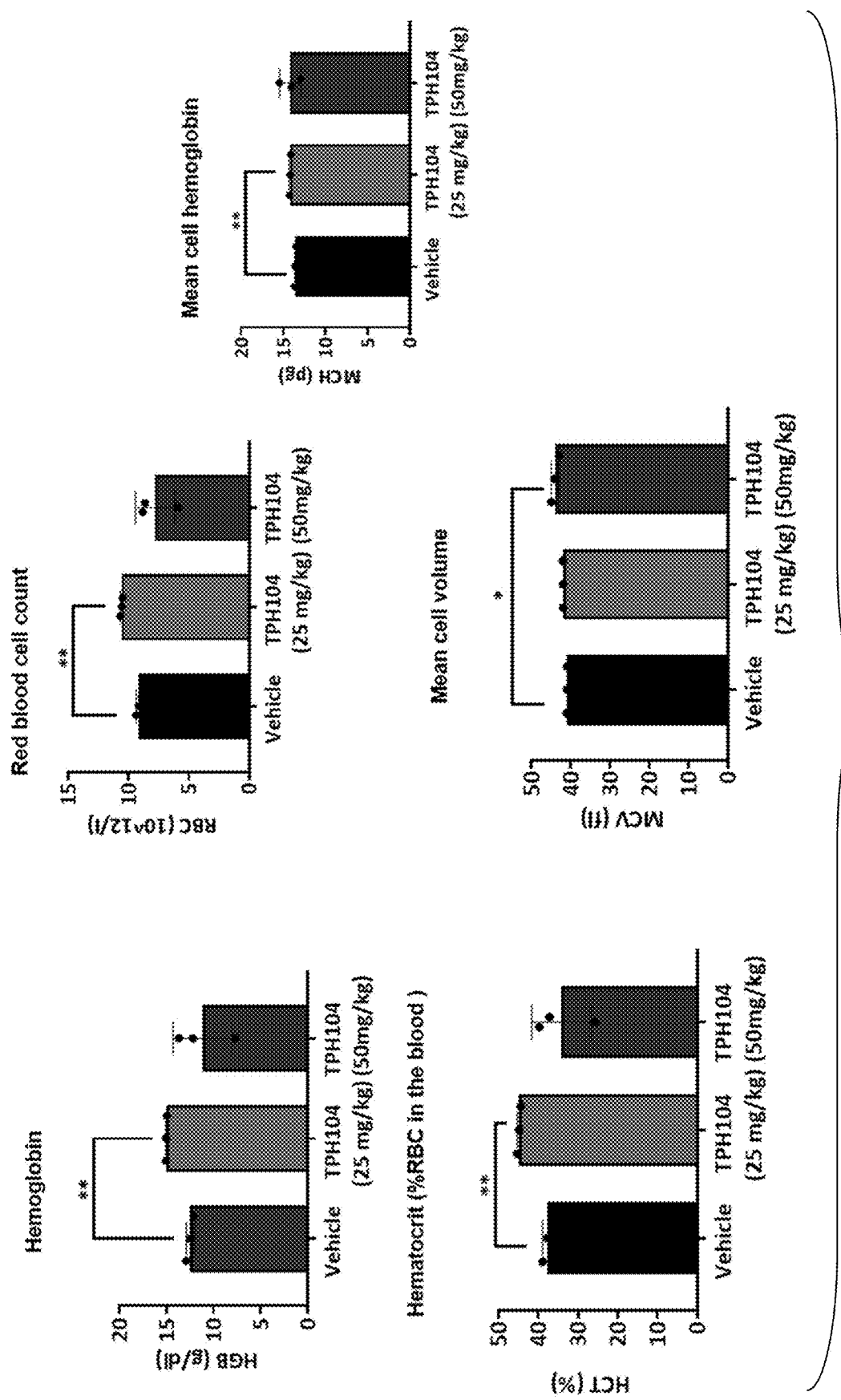

FIGS. 23A-23E: Animal toxicity data for TPH104. FIG. 23A shows the results of TPH104 compound tested for its acute toxicity in C57BL/6 male mice. TPH104 showed no obvious toxicity in mice up to 50 mg/kg. Different organs including heart, liver, brain, pancreas, kidney, and spleen were harvested for H&E. Whole organs as well as 20× images are shown. FIG. 23B shows the in vivo evaluation of the effect of TPH104 (25 mg/kg and 50 mg/kg) on the blood chemistry. The following components of the blood profile were measured: ALB, TP, GLOB, ALT, AMY, TBIL, CRE, BUN, CA, PHOS, GLU, Na+ and K+. Statistical analysis was performed whereby p<0.01, *p<0.001 compared to vehicle control. FIGS. 23C-23E shows the effect of TPH104 (25 mg/kg and 50 mg/kg) on the blood chemistry parameters lymphocytes, white blood cell count, monocytes, neutrophils, mean cell hemoglobin concentration, mean platelet volume, hemoglobin, hematocrit, platelet, procalcitonin, red blood cell count, mean cell hemoglobin, and mean cell volume. Statistical analysis was performed whereby p<0.01, *p<0.001 compared to vehicle control.

Figure 24:
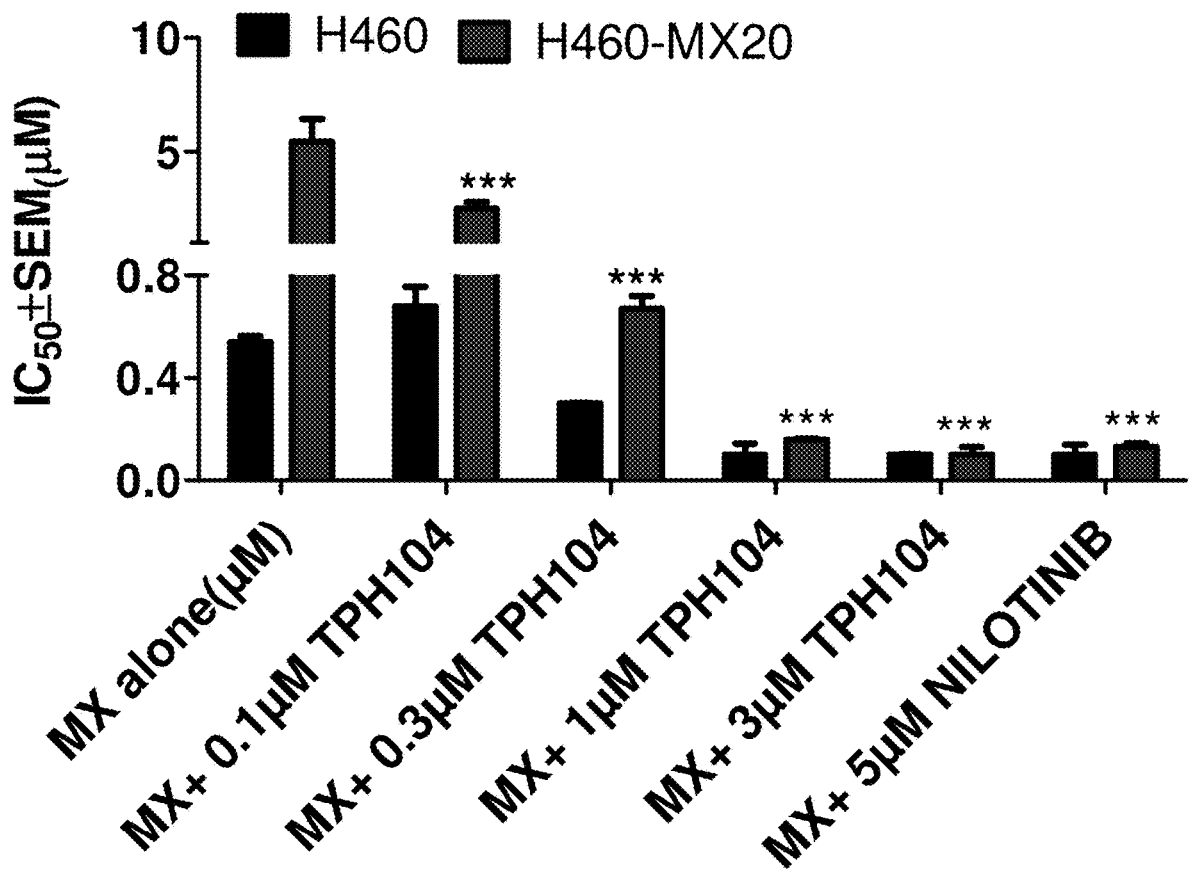

FIG. 24: TPH104 when combined with mitoxantrone increases its efficacy in non-small cell lung cancer cells (H460) and non-small cell lung cancer cells that are resistant to mitoxantrone (H460-MX20). Bar graph showing the $IC_{50}$ of MX alone and in combination with TPH104. TPH104 significantly lowered the $IC_{50}$ of MX in a concentration dependent manner The $IC_{50}$ values shown in this table and graph are represented as mean±SD of three independent MTT experiments, each performed in triplicates. p<0.01, *p<0.001 compared to control.

Figure 25:
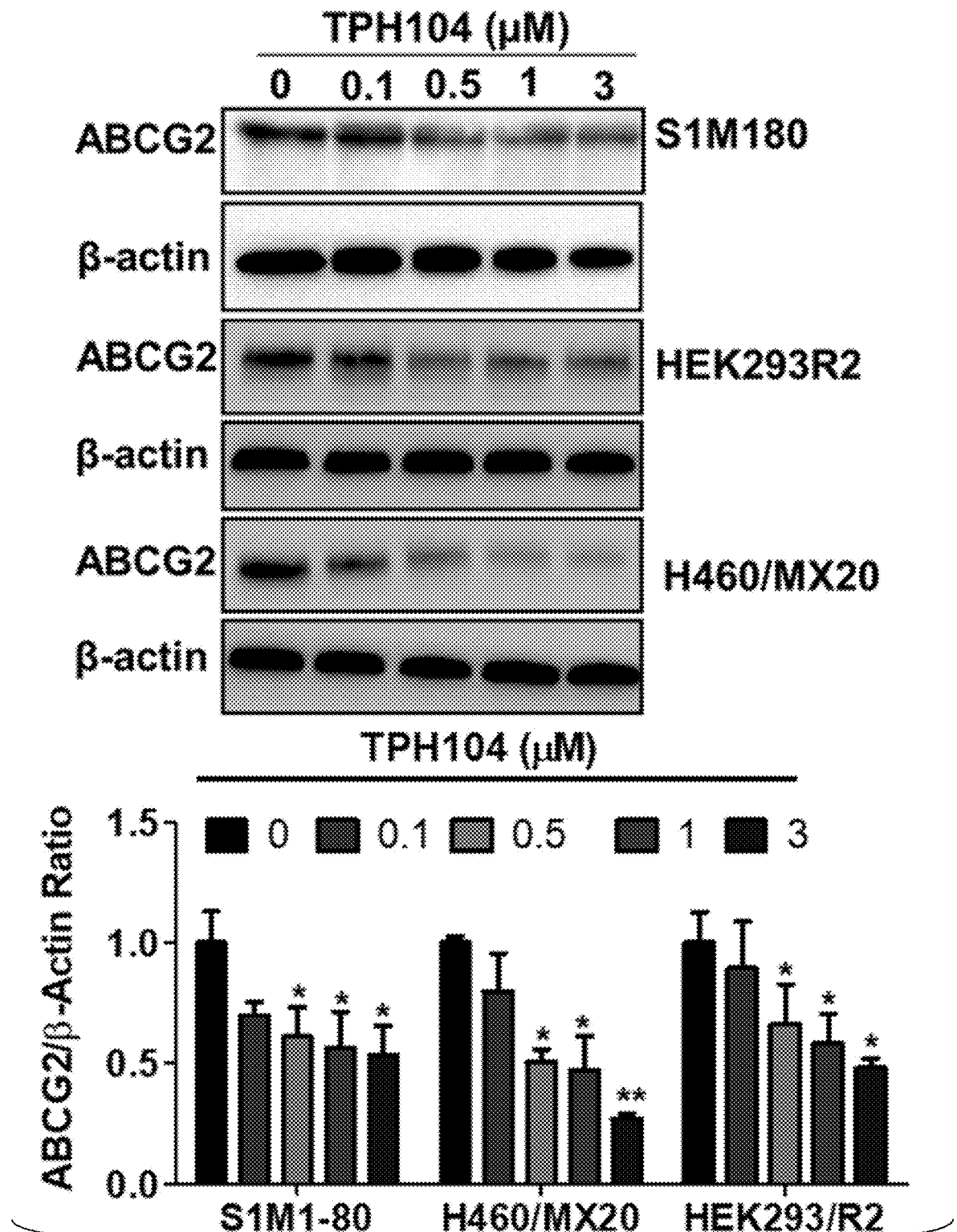

FIG. 25: TPH104 reverses multidrug resistance by down-regulating the expression of ABCG2 transporter in a concentration dependent fashion in drug resistant small cell lung cancer cells (H460/MX20), colon cancer cells (S1M180) and ABCG2-transfected cells (HEK293/R2). The bar graph represents the quantified values of the ratio of ABCG2/β-actin. The data represent mean±SEM of three independent western blots. *p<0.05, **p<0.01 compared to control.

Figure 26:
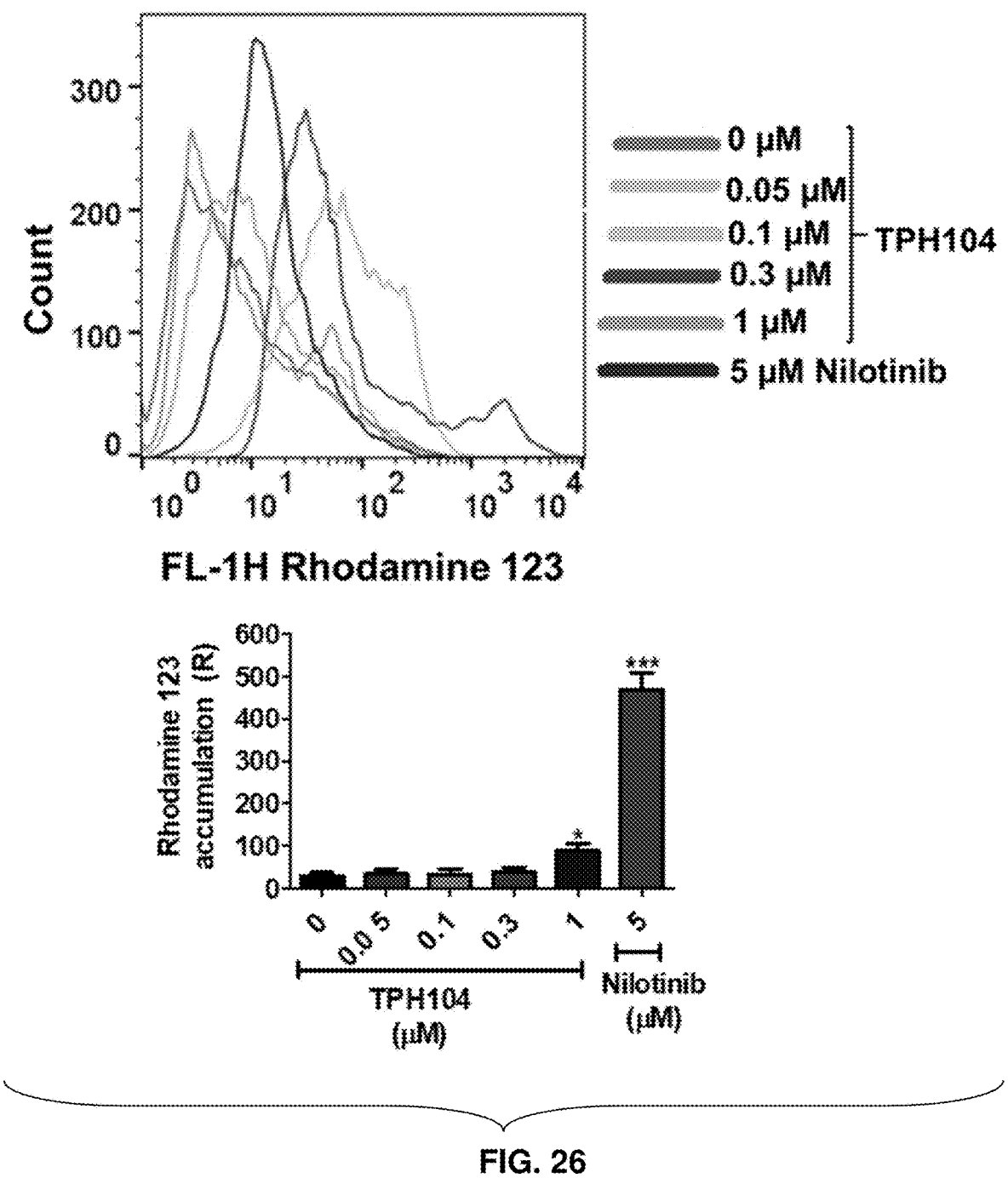

FIG. 26: TPH104 reverses multidrug resistance by blocking the function of ABCG2 transporter. The effect of TPH104 and nilotinib on the intracellular accumulation of rhodamine 123 in ABCG2 overexpressing S1M180 cells. The top image is a graph showing the concentration-dependent increase in the accumulation of rhodamine 123 in S1M180 cells incubated with TPH104. Red filled=control; sky blue filled=0.05 µM; brown filled=0.1 µM; dark blue filled=0.3 µM; lime green filled=1 µM of TPH104, respectively, and olive green=nilotinib, 5 µM. The bottom image is a bar graph representing the relative rhodamine 123 accumulation levels. The data shown as means±SEM of three independent experiments. *p<0.05; ***p<0.001 compared to the control.

Figure 27A:
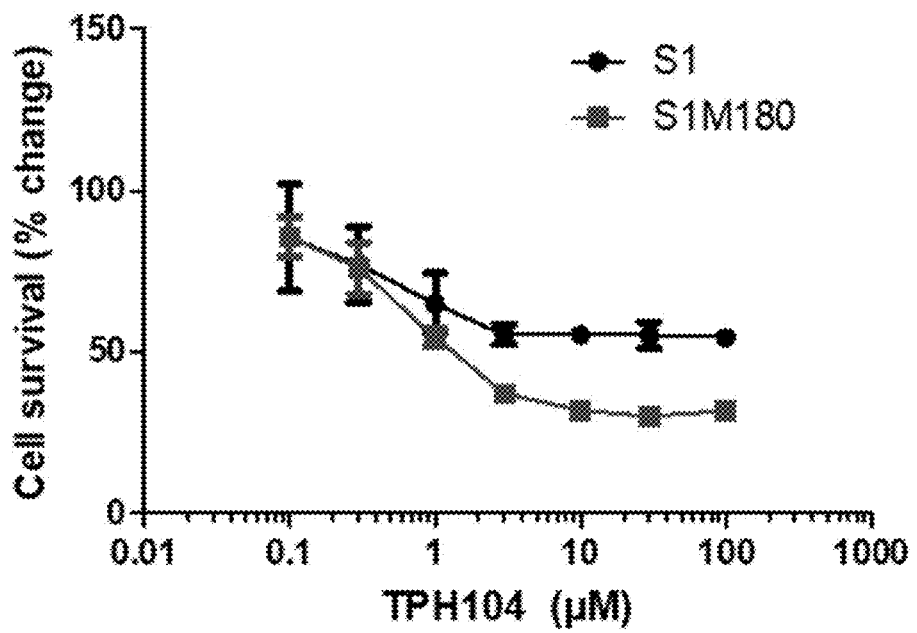
Figure 27A:
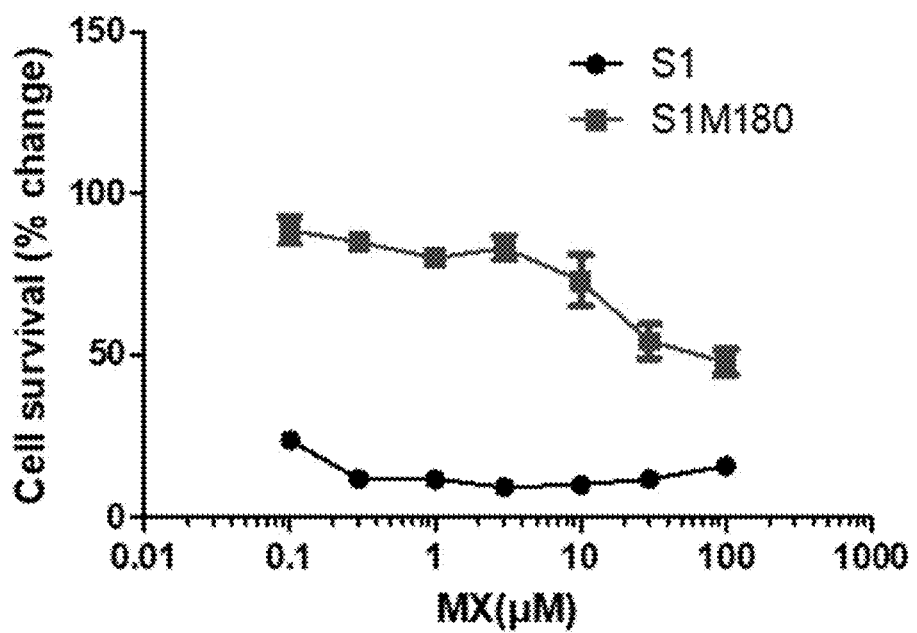
Figure 27B:
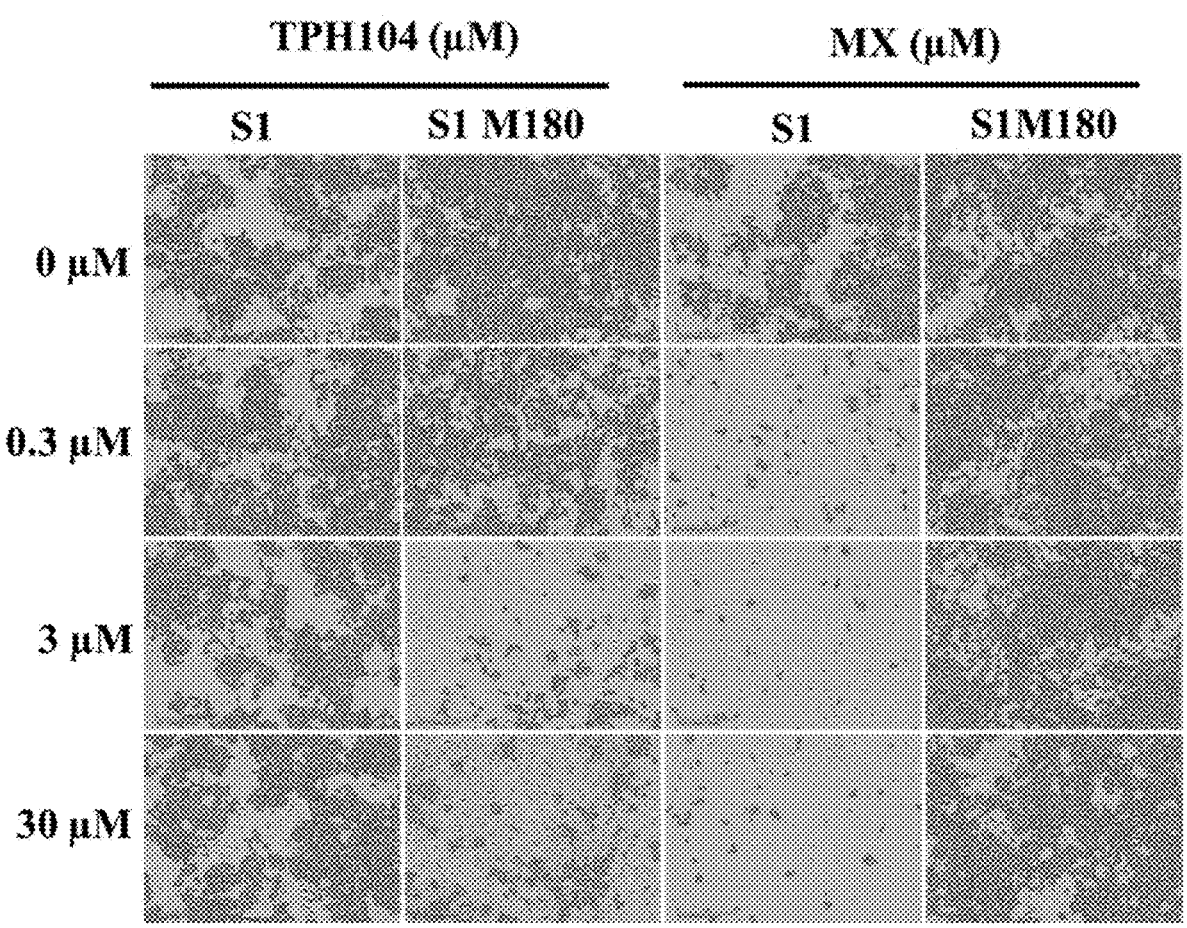
Figure 27C:
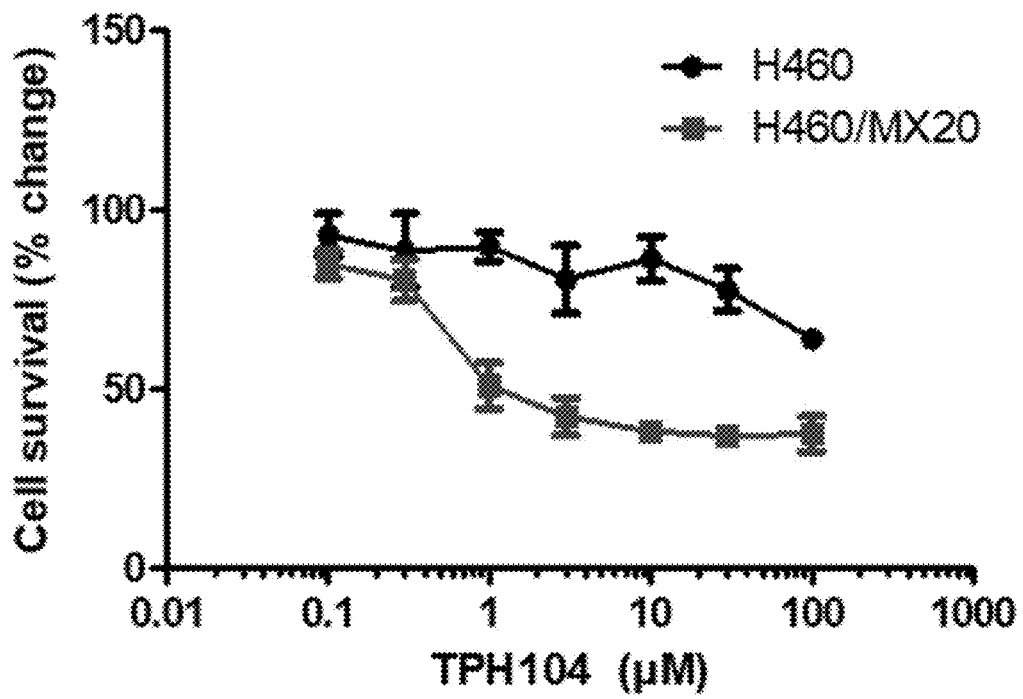
Figure 27C:
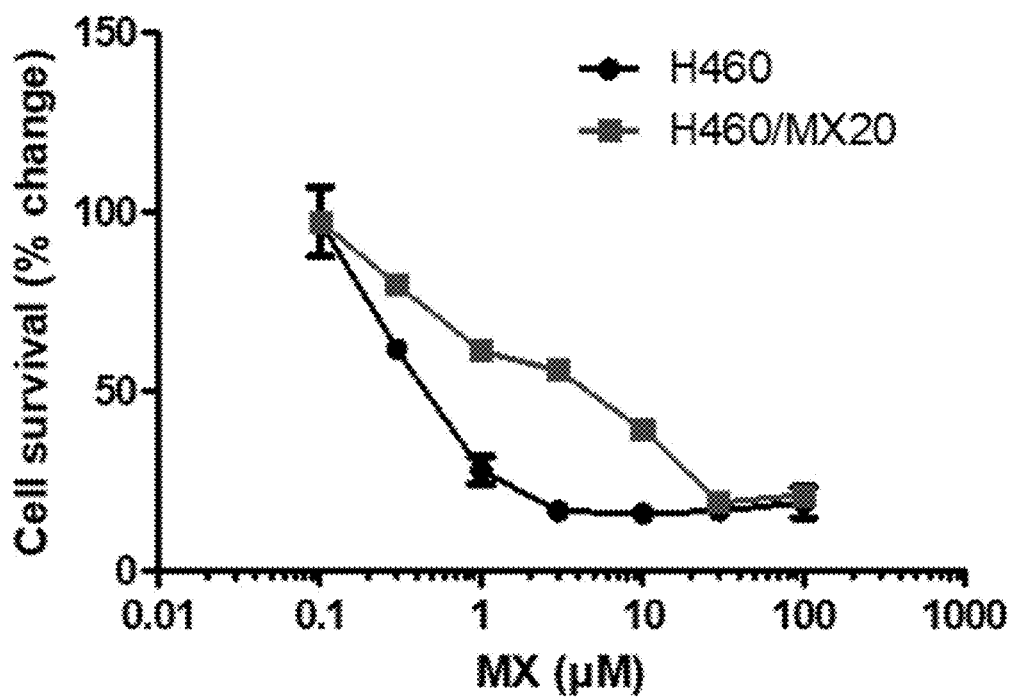
Figure 27D:
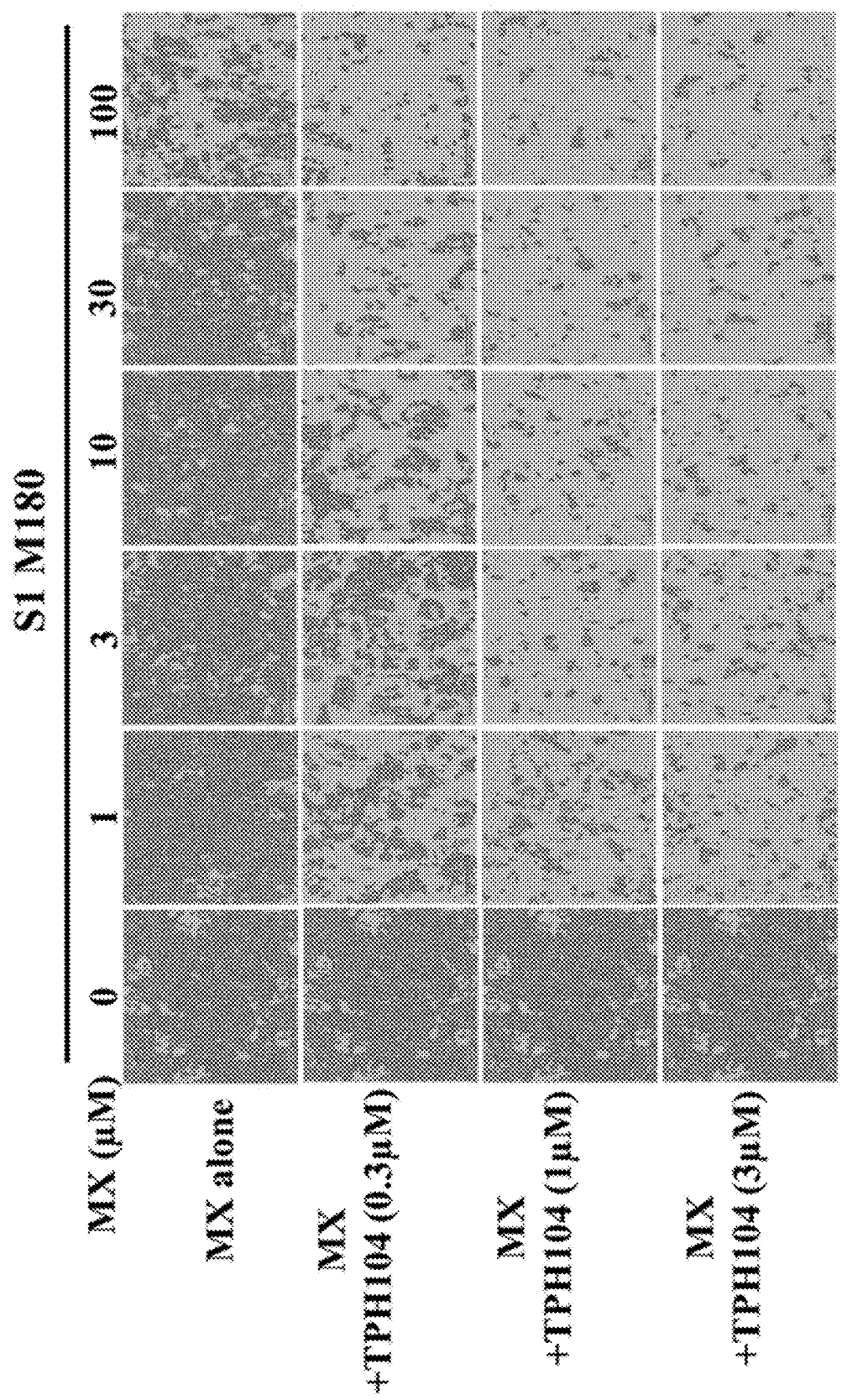

FIGS. 27A-27D: TPH104 induces collateral sensitivity. FIGS. 27A-27D show that TPH104 reverses ABCG2 transporter mediated multidrug resistance by producing collateral sensitivity, i.e., more effective in drug resistant cells overexpressing ABCG2 transporters. FIG. 27A and FIG. 27C show that TPH104 produces collateral sensitivity in S1M180 and H460-MX20 ABCG2-overexpressing cells compared to their parental S1 (colon) and H460 (lung) cancer cells, respectively. The data is shown as means±SEM of three independent experiments. FIG. 27B and FIG. 27D show phase-contrast microscopic images showing the collateral sensitivity effect of TPH104, i.e., S1M180 and H46-MX20 ABCG2-overexpressing cells were hypersensitive to TPH104 (0.3, 3, and 30 µM) compared to their parental S1 (colon) and H460 (lung) cancer cells.

FIG. 29: Table 2, showing results of THP104 compounds tested for their cytotoxicity against TNBC and non-TNBC cell lines.

FIG. 30: Table 3, showing results of cytotoxicity screening of TPH104 compounds against Colon (HCT-116, LOVO and S1), Prostate (DU145), Ovarian (Ov 2008), and Lung (H460) cancer cell lines.

DETAILED DESCRIPTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

The present disclosure provides materials to induce cell death through nonapoptotic mechanisms, namely necroptosis induction or autophagy inhibition or a combination of both. Small molecules have been discovered to act through this mechanism with therapeutic applications in disorders or anomalies that involves cell proliferation, metastasis, and drug resistance, particularly, but not exclusively, cancer. The structure activity relationship and the essential pharmacophore needed to produce this cell death are also described herein. The compounds described herein kill aggressive cancer cells through necroptosis (programmed necrosis) induction and inhibition of cell survival process known as autophagy (self-eating). The cell death is caspase-independent and inhibits epithelial to mesochymal transition pathways. Such mechanism is due to increased activation of phosphorylation of RIP, MLKL through caspase 8 regulation. This is useful in targeting apoptotic resistant cancers, combination or adjuvant chemotherapy, immunotherapy, and stem cell treatment Phenotypic based drug discovery has been successful in the generation of first-in-class drugs as compared to target-based approaches. Phenotypic screens have been successfully applied at many instances for identification of novel chemotherapeutics that acts through non-apoptotic mechanisms. Triple negative breast cancer (TNBC) cells, characterized by heterogeneity and lack of well-defined clinical targets are ideal for phenotypic screens aimed at discovering novel class of chemotherapeutics that can induce necroptosis in cancer cells. This because triple negative breast cancer therapy suffers from both paucity of actionable targets and lack of targeted therapies which mainly acts through apoptotic cell death mechanisms. Related to the foregoing, a cell-based phenotypic screen of an inhouse database of 2100 compounds on TNBC cell and normal (breast and human fibroblast) cells led to the discovery of TPH104, a 5-aryllthieno[2,3-d]pyrimidine derivative that induces necroptotic cell death on TNBC cells.

In accordance with the present disclosure, compounds having the following Formulas I-VII may be used to induce cell death:

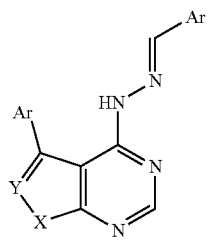

Formula I where X is S, O, or NH, Y is CH or N, and each Ar is independently aryl or heteroaryl with or without substituents;

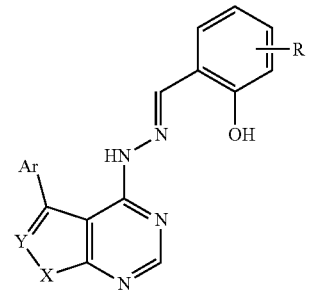

Formula II where X is S, O, or NH, Y is CH or N, Ar is aryl or heteroaryl with or without substituents, and R is an alkyl, alkyl amino, alkoxy, halogen, nitro, or cyano substituent;

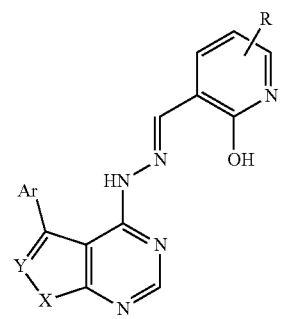

Formula III wherein X is S, O, or NH, Y is CH or N, Ar is aryl or heteroaryl with or without substituents, and R is an alkyl, alkyl amino, alkoxy, halogen, nitro, or cyano substituent;

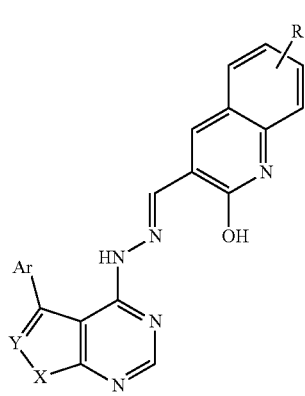

Formula IV wherein X is S, O, or NH, Y is CH or N, Ar is aryl or heteroaryl with or without substituents, and R is an alkyl, alkyl amino, alkoxy, halogen, nitro, or cyano substituent;

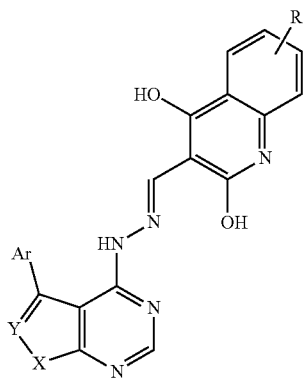

Formula V wherein X is S, O, or NH, Y is CH or N, Ar is aryl or heteroaryl with or without substituents, and R is an alkyl, alkyl amino, alkoxy, halogen, nitro, cyano substituent;

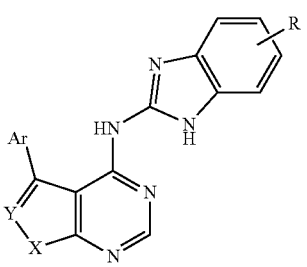

Formula VI wherein X is S, O, or NH, Y is CH or N, Ar is aryl or heteroaryl with or without substituents, and R is an alkyl, alkyl amino, alkoxy, halogen, nitro, or cyano substituent; or

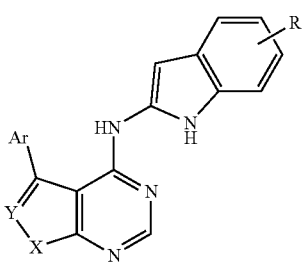

Figure 1:
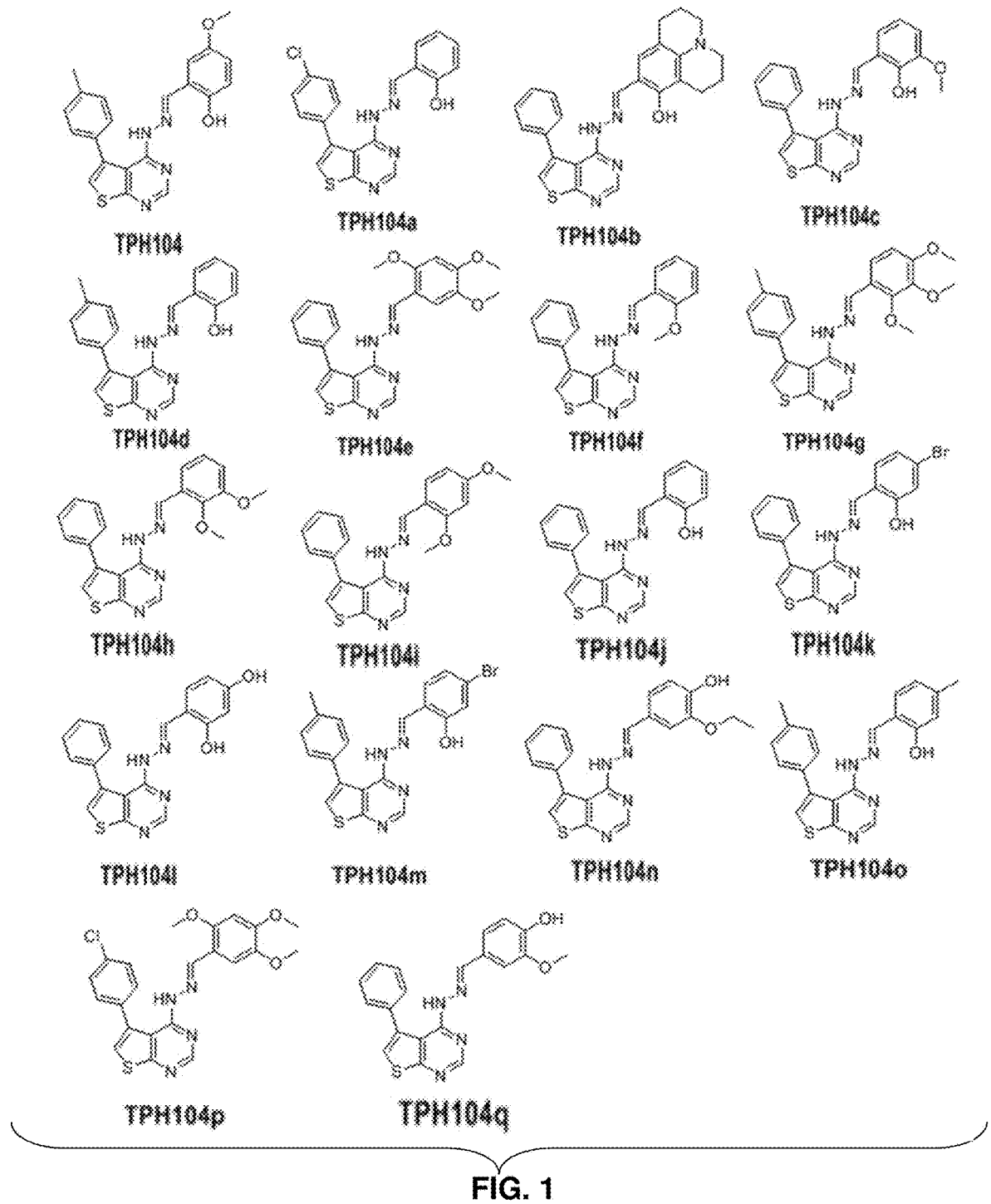
FIG. 1: Structures of thieno-pyrimidin-4-yl-hydrazinylidene (TPH) compounds.

Formula VII wherein X is S, O, or NH, Y is CH or N, Ar is aryl or heteroaryl with or without substituents, and R is an alkyl, alkyl amino, alkoxy, halogen, nitro, or cyano substituent. Non-limiting example compounds of Formulas I-VII are depicted in FIG. 1, and include the compound TPH104:

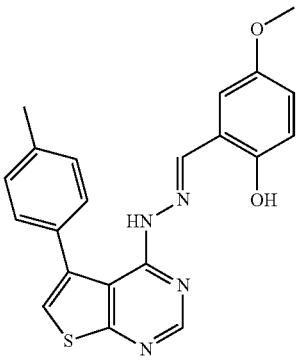

TPH104

The compounds of Formulas I-VII can be made by any suitable method. As one non-limiting example, TPH104 is commercially available.

The compounds described herein can be used and administered in different types of simple and complex formulations. They can be formulated simply by dissolving them in different solutions. Alternatively, they can be formulated as complex pharmaceutical delivery systems such as tablets, capsules, powders, with a range of reagents, excipients, stabilizers, or the like.

Pharmaceutical compositions of the present disclosure comprise an effective amount of a compound of Formulas I-VII (such as, but not limited to, TPH104) (an "active ingredient"), and/or additional agents, dissolved or dispersed in a pharmaceutically acceptable carrier. The phrases "pharmaceutical" or "pharmacologically acceptable" refer to molecular entities and compositions that produce no adverse, allergic, or other untoward reaction when administered to an animal, such as, for example, a human The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158, 5,641,515, and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.), and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

In particular embodiments, the compounds and compositions described herein are useful for treating various cancers such as, but not limited to: breast cancer, colon cancer, prostate cancer, ovarian cancer, or lung cancer. The cancers may be mitoxantrone-resistant, doxorubicin-resistant, apoptotic-resistant, and/or multidrug-resistant cancers. Furthermore, as noted above, the compounds and compositions herein can be used in combination therapies. That is, the compounds and compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

By way of a non-limiting example of a combination therapy, the compounds or compositions described herein can be administered in combination with one or more suitable anti-cancer agents including, but not limited to: chemotherapeutic agents; cytotoxins; antimetabolites; alkylating agents; protein kinase inhibitors; anthracyclines; antibiotics; miRNAs; anti-miRNAs; antimitotic agents (e.g. antitubulin agents); corticosteroids; radiopharmaceuticals; proteins such as cytokines, enzymes, or interferons; biological response modifiers such as krestin, lentinan, sizofiran, picibanil, ubenimex; anti-angiogenic compounds such as acitretin, fenretinide, thalidomide, zoledronic acid, angiostatin, aplidine, cilengtide, combretastatin A-4, endostatin, halofuginone, rebimastat, removab®, Revlimid®, squalamine, ukrain, or Vitaxin®; platinum-coordinated compounds such as cisplatin, carboplatin, nedaplatin, or oxaliplatin; camptothecin derivatives such as camptothecin, 10-hydroxycamptothecin, 9-aminocamptothecin, irinotecan, SN-38, edotecarin, or topotecan; compounds or chelates that include radionuclides; or combinations thereof. Examples of suitable interferons include, but are not limited to interferon alpha, interferon alpha-2a, interferon, alpha-2b, interferon beta, interferon gamma-1a, interferon gamma-1b (Actimmune), interferon gamma-n1, or combinations thereof.

In certain embodiments, the anti-cancer agent is one or more of hydroxyureas, taxol®, adriamycin, 5-fluorouracil, cyclophosphamide, etoposide, altretamine, ifosfamide, vinblastine sulfate, estramustine phosphate, suramin, strontium-89, filgrastim, lentinan, sizofilan, TheraCys®, ubenimex, WF-10, aldesleukin, alemtuzumab, BAM-002, dacarbazine, daclizumab, denileukin, gemtuzumab ozogamicin, ibritumomab, imiquimod, lenograstim, lentinan, Corixa, molgramostim, OncoVAX-CL, sargramostim, tasonermin, tecleukin, thymalasin, tositumomab, Virulizin®, Z-100, epratuzumab, mitumomab, oregovomab, pemtumomab (Y-muHMFG1), Provenge® (Dendreon), alitretinoin, ampligen, atrasentan bexarotene, bortezomib, bosentan, calcitriol, exisulind, finasteride, fotemustine, ibandronic acid, miltefosine, mitoxantrone, 1-asparaginase, procarbazine, dacarbazine, hydroxycarbamide, pegaspargase, pentostatin, tazarotne, Telcyta® (TLK-286, Telik Inc.), Velcade® (bortemazib, Millenium), or tretinoinor.

Another non-limiting example of a combination therapy for cancers or other diseases is the combination of compounds of Formulas I-VII, or a Formula I-VII compound-containing composition, with one or more surgical treatments. Suitable surgical treatments include, but are not limited to, a polypectomy, a colectomy, a transanal resection, a wedge resection, a lobectomy, a pneumonectomy, a sleeve reduction, a hysterectomy, a bilaterial salpingo-oophorectomy, an omentectomy, or a nephrectomy. Other possible therapies suitable for combination with a Formula I-VII compound or Formula I-VII compound-containing composition include, but are not limited to, immunotherapy, hormone therapy, radiation therapy, or a combination thereof.

Embodiments of the present disclosure further include methods of determining coverage or denial of health insurance reimbursement and/or payment for treatments of disease comprising the compounds or compositions described herein. In certain embodiments, the treatment comprises a compound of Formulas I-VII, and a provider of health insurance denies coverage or reimbursement for the treatment.

EXAMPLES

In these examples, it is shown that structurally constrained thieno-pyrimidine probes induce a form of non-apoptotic cell death characterized known as necroptosis in TNBC cells. In 2005, a group of researchers from Havard Medical School was the first to show that although morphologically similar to necrosis, necroptosis takes place under regulated signaling pathways and is mediated by different biomolecular markers. Although the molecular mechanisms that regulate necroptosis are still poorly understood, necroptosis has been reported to take place under caspase-deficient situations where cancer cells may develop resistance to chemotherapeutic agents that promote apoptosis. Therefore, in this in vitro study, the efficacy of a series of thieno-pyrimidime compounds on the growth of TNBC and colon cancer cells was deteremined. In addition, the effect of the compounds on colony formation and metastasis in TNBC cells was deteremined. Finally, experiments to determine the effect of the compound TPH104 were conducted on some of the key components of necroptosis in TNBC cells.

In view of interesting mechanistic and cytotoxic profile exhibited by TPH104, the pharmacophoric and structural elements deemed significant for the selective and potent cytotoxic effects on TNBC cells were evaluated. To this end, several commercial databases were searched, and 17 similar molecules from the VitasM database were retrieved with considerable structural diversity in terms of the substitution on the aryl ring A attached to the thienopyrimidine scaffold and aryl ring B attached to hydrazino moiety. Further, the biological evaluation of the 17 molecules sheds light on the structural features deemed important for the selective cytotoxicity shown by this class of molecules. With this understanding, the 17 molecules were subjected to a screening protocol comprising of two TNBC, two non-TNBC, and one normal cell lines. FIG. 1 displays TPH104 and the 17 other molecules.

The cytotoxicity data of the 17 TPH104 derivatives is shown in Table 1. The cytotoxicity data summarized in Table 1 indicates that the screened compounds can be classified into four groups viz compounds that are equipotent to TPH104 (TPH104b & TPH104c), compounds that exhibit comparable potency to that of TPH104 (TPH104a & TPH104m), compounds that show moderate potency compared to TPH104 (TPH104d, TPH104j, TPH104k, TPH104o, and TPH104l) and compounds that exhibit poor or no potency against the studied cell lines (TPH104e, TPH104f, TPH104g, TPH104h, TPH104i, TPH104n, TPH104p, and TPH104q). None of the 17 compounds evaluated elicit greater TNBC inhibitory potency than that of TPH104.

TABLE 1

Cytotoxicity data

| | $IC_{50} \pm SD$ (μM) | | | | |
|---|---|---|---|---|---|
| | TNBC | | Non TNBC | | Normal |
| Comp. Code | MDA-MB231 | MDA-MB468 | ZR-75-1 | MCF-7 | HMEC |
| TPH104 | 0.19 ± 0.01 | 0.25 ± 0.05 | 8.56 ± 1.95 | 3.84 ± 1.36 | 82.30 ± 17.76 |
| TPH104a | 0.28 ± 0.06 | 0.44 ± 0.26 | 2.29 ± 0.23 | 6.96 ± 1.15 | 27.88 ± 8.95 |
| TPH104b | 0.25 ± 0.02 | 0.23 ± 0.05 | 1.18 ± 0.53 | 1.52 ± 0.57 | >100 |
| TPH104c | 0.23 ± 0.01 | 0.18 ± 0.02 | 10.68 ± 1.10 | >100 | >100 |
| TPH104d | 2.29 ± 0.16 | 2.22 ± 1.82 | 6.05 ± 2.02 | >100 | 33.13 ± 2.33 |
| TPH104e | >100 | >100 | >100 | >100 | >100 |
| TPH104f | 29.38 ± 0.08 | 7.87 ± 1.53 | >100 | >100 | >100 |
| TPH104g | 27.64 ± 0.15 | 27.34 ± 4.53 | 28.91 ± 2.61 | 27.19 ± 2.92 | >100 |
| TPH104h | 96.70 ± 0.14 | >100 | >100 | 62.97 ± 2.89 | >100 |
| TPH104i | >100 | >100 | >100 | >100 | >100 |
| TPH104j | 0.78 ± 0.28 | 0.56 ± 0.34 | 3.42 ± 1.53 | 2.84 ± 0.96 | 4.52 ± 1.38 |
| TPH104k | 1.29 ± 0.52 | 0.91 ± 0.09 | 6.07 ± 5.18 | 15.60 ± 6.50 | >100 |
| TPH104l | 0.78 ± 0.38 | 1.47 ± 0.84 | 8.68 ± 1.04 | 6.59 ± 0.58 | >100 |
| TPH104m | 0.44 ± 0.21 | 0.29 ± 0.01 | >100 | 2.73 ± 1.02 | >100 |
| TPH104n | 23.10 ± 1.88 | 21.71 ± 0.30 | 21.49 ± 3.67 | >100 | >100 |
| TPH104o | 0.43 ± 0.19 | 0.56 ± 0.24 | 1.04 ± 0.54 | 1.22 ± 0.60 | >100 |
| TPH104p | 62.20 ± 8.83 | 55.89 ± 0.98 | 22.99 ± 0.59 | >100 | >100 |
| TPH104q | 18.60 ± 2.57 | 22.23 ± 0.78 | 21.37 ± 3.11 | 23.51 ± 1.12 | >100 |

Structure-activity relationship analysis of the cytotoxicity data revealed that at least one structural feature is significant for the cytotoxic potency and selectivity exhibited by thieno[2,3-d]pyrimidines: a hydroxyl group on the C2-position of the aryl ring linked to hydrazine moiety. Removal or methylation of the 2-hydroxyl group resulted in either drastic reduction or loss of cytotoxic potency. Substitution in C3/C4 and C5 on the aryl ring B contributes to the selectivity for TNBC cells over normal cells while causing no significant improvement in the cytotoxic potency shown by the thieno[2,3-d]pyrimidines. Similarly, methyl/chloro substitution on the C4 of the aryl ring A improves the TNBC selectivity with little or no impact on cytotoxic potency elicited by the title compounds. Taken together, the preliminary structure-activity analysis indicates that the ability of thienopyridmidines to induce selective necroptotic cell death in TNBC cells relies on specific structural requirements, consistent with them being selective anti-TNBC chemotherapeutics.

Materials and Methods

Chemicals and Reagents

The TPH104 compounds were purchased from Specs (Zoetermeer, The Netherlands) and Vitas-M-Laboratory Vitascreen, LLC (Champain, IL, USA). Dulbecco's Modified Eagle Medium (DMEM) was purchased from GE Healthcare Life Sciences (Marlborough, MA) and HyClone Laboratories (Logan, UT, USA). 3-(4,5-Dimethylthiazol-2-yl)-2,5-diphenyltetrazolium bromide (MTT) was purchased from Calbiochem EMD Millipore (Billerica, MA, USA). The 0.25% trypsin +2.2 mM EDTA lysis buffer was purchased from Corning Life Sciences (VWR International, LLC, Radnor, PA, United States). The Alexa Fluor® 488 molecular probe and anti-mouse IgG (R) Alexa Fluor® 488 molecular probe, as well as all the antibodies (primary and secondary) used in this example were purchased from Cell Signaling Technology (Danvers, MA, USA). Propidium iodide (PI) was purchased from Life Technologies (Eugene, OR, USA). Fluoroshield mounting medium, containing 4',6-diamidino-2-phenylindole dihydrochloride (DAPI), was purchased from Abcam (Cambridge, MA, USA). 2',7'-Dichlorofluorescin diacetate powder and crystal violet dye were purchased from Sigma-Aldrich (St. Louis, MO, USA). The 6, 12, 24 and well plates and the 6.5 mm diameter inserts, with 8 μM pore size polycarbonate membrane for 24 well plates, were purchased from Corning Incorporated (One Riverfront Plaza Corning, NY 14831, USA). Growth-factor-reduced matrigel was purchased from BD Biosciences (Ontario, Canada). Phosphate buffer saline (PBS) was purchased from Media Tech, Inc. (Manassas, VA, USA). Fetal Bovine Serum (FBS) and penicillin/streptomycin, Polyvinylidene difluoride (PVDF) membranes, the mitochondrial membrane potential apoptosis kit, with Mitotracker™ Red Annexin V Alexa Fluor® 488 and acridine orange dye, were purchased from Thermo Fisher Scientific (Richard St, Wayne, MI, USA).

Cell Culture

The following cancer and non-cancer cell lines were used in the initial cytotoxicity screening of the TPH104 compounds: triple negative breast cancer (TNBC): MDA-MB468, MDA-MB 231, and BT-20; non-TNBC: MCF-7 and ZR-75-1; ovarian: Ov2008; prostate: DU145; colon: HCT-116, S1, and LOVO; lung: H460; normal kidney: HEK-293; normal breast: HMEC; and normal colon: CRL-1459. All cells were cultured in Dulbecco's modified Eagle medium (DMEM), supplemented with 10% fetal bovine serum (FBS), and 1% penicillin/streptomycin (P/S). Cells were allowed to grow as adherent monolayers in T25 flasks in a humidified incubator with 5% $CO_2$ at 37° C. for a period of 24 h, unless otherwise specified for certain experiments.

Cell Viability Assay

The MTT assay was used to determine the cytotoxicity of all of the compounds. Briefly, in a 96-well flat-bottom cell culture plate, the cells were seeded at a density between $3-5 \times 10^3$ cells/well (180 μl in each well) and incubated for 24 h (a hemocytometer was used for cell counting). The next day, the cells were incubated with different concentrations of the nine compounds (0, 0.1, 0.3, 1, 3, 10, 30, and 100 μM) for 72 h. After 72 h, 20 μl of 5 mg/ml of 3-(4,5-dimethyl-thiazol-2-yl)-2,5-diphenyltetrazolium bromide (MTT) was added to the plate and incubated with the cells for 3 h at 37° C. In this experiment, the living cells will reduce the soluble MTT dye to non-soluble purple formazan crystals. Following incubation, the media containing MTT removed via suction and 100 μL of 100% dimethyl sulfoxide (DMSO) was added to dissolve the formazan crystals. Subsequently, the plate was shaken for 2 minutes and the absorbance was measured at a wavelength of 570 nm using a SpectraMax iD3 Multi-Mode Microplate Reader (Molecular Devices, Sunnyvale, CA). The $IC_{50}$ values of each compound were calculated and used to determine the selectivity ratio ($IC_{50}$ in normal cells/$IC_{50}$ in cancer cells) of each compound as previously described. Based on the results obtained from these experiments, the compound TPH104, which had the lowest $IC_{50}$ value, was selected for further experiments.

Cell Cycle Analysis

The cell cycle analysis was performed to evaluate the effect of TPH104 on the normal cell cycle in the TNBC cell lines (i.e. MDA-MB 468, MDA-MB231 and BT-20). Cells were plated in a 6-well plate at a suitable density as previously described [45] and incubated overnight to allow for cell attachment. The following day, cells were incubated with different TPH104 concentrations (0.5, 1, or 2 μM) or vehicle for 12 h. The cells were harvested by trypsinization and collected in individual test tubes. Subsequently, cells were washed 3× with ice cold PBS and fixed with 70% ethanol for 30 minutes. Following fixation, cells were again washed 3× with intermittent centrifugation at 2000 rpm for 5 minutes and incubated with 100 μl RNAse (from a 100 μg/ml stock) (to ensure that only DNA was stained). Two hundred μl of PI (from a 50 μg/ml stock solution) was added to each test tube and cells were stain cells for at least 15 minutes on ice. Finally, a FACS Calibur flow cytometer (BD Biosciences, San Jose, CA) was used to detect the distribution of the cells following incubation with vehicle or TPH104. FlowJo v10.2 software from FlowJo LLC (Ashland, OR) was used for data analysis.

Cell Colony Formation Assay

This assay was used to measure the size and rate of colony formation for TNBC cells, with or without TPH104, as previously reported. Briefly, in a 6-well cell culture plate, cells were seeded at a density of 250,000 cells/well and allowed to grow/attach overnight. The next day, the cells were incubated with different concentration of TPH104 (0.1, 1, or 10 μM) or vehicle and incubated for 12 h at 37° C. Following incubation, the cells were harvested, counted, and reseeded at a density of 500-800 cells/well (1 ml in each well), in a new 6-well plate, with complete medium for 10 days. The medium was changed every 2 days in order to prevent cell starvation. On the $10^{th}$ day, the colonies were fixed with absolute methanol at room temperature for 30 minutes. Subsequently, cells were stained with 0.1% crystal violet dye (Sigma, USA) for an additional 30 minutes. Finally, the fixed and stained colonies were viewed, pictured (at 4, 10, and 20×) and counted using an EVOS-FLC microscope (Thermo Fisher Scientific, Wayne, MI, USA). The following equation was used to calculate the colony formation rate:

Colony formation rate=number of colonies formed/ number of seeded cells (500)×100%

Trans-Well Migration Assay

This assay was used to assess the migration and invasiveness of TNBC cells. In this assay, 24 well-plates with 24 well inserts of 8 μm pore size, (Corning, Cambridge, MA, USA), were used. The inserts were pre-coated with growth-factor reduced matrigel (1:40) and added to each well, forming two chambers (upper and lower). Briefly, cells were seeded at a density of 10,000 cells/well in the upper chamber of the inserts. The lower chamber was filled with cell-free DMEM medium supplemented with 10% FBS and 1% P/S. The next day, cells were incubated with 0.1, 1, or 10 μM of TPH104 or vehicle for 24 h to allow the cells to migrate through the porous membrane into the lower chamber. Following incubation, cotton swabs were used to wipe away the non-migrated, stationary cells in the upper chamber. The migrated cells were fixed with 100% methanol and stained with 0.1% crystal violet dye. The migrated cells were then viewed, pictured and counted using an EVOS-FLC microscope as previously reported.

Scratch/wound Healing Assay

MDA-MB231 cells were seeded in a 6 well-plate (10-20,000 cells/well) and incubated at 37° C. until they reached 60-80% confluence and formed a complete monolayer, as previously reported. Subsequently, a wound was created by scratching the monolayer with a 10 µl sterile pipette tip. The floating cells were washed away with sterile PBS, making the wound area clear and completely empty. Immediately following monolayer scratching, TPH104 (0.5, 1, 2, 5 or 10 µM) or vehicle were added to the cell culture media (2 ml total in each well) and incubated at 37° C. for 36 h. The wound closure was monitored over time by taking pictures after 0 h, 12 h, 24 h, and 36 h of incubation using an EVOS-FLC microscope. Image J software NIH, Bethesda, MD, USA) was used to determine the areas of the wound at different time points as previously reported.

Hoechst 33258 Assay

To detect DNA fragmentation following apoptotic cell death, the Hoechst 33258 assay was performed. Briefly, TNBC cells were seeded in a 6-well plate at a density of 10,000 cells/well over 18-mm cover slips and incubated for 24 h. Following incubation, TPH104 (1, 2, or 5 µM), or vehicle were added for an additional 12 h. Subsequently, Hoechst 33258 (Sigma Aldrich, USA) was added to the cells at a concentration of 0.5 mg/mL and incubated for 30 minutes at 37° C. The cells were then washed 3× with phosphate buffered saline (PBS). Subsequently, the cover slips were mounted on a microscope glass/slide and allowed to dry for at least 2 h. Stained cells from each cover slip were captured from randomly selected fields under a fluorescent microscope (EVOS-FLC cell imaging system, Thermofisher scientific) to qualitatively determine the proportion of viable and apoptotic cells based on their relative fluorescence and nuclear fragmentation as previously described.

Calcein AM Assay for P-gp Modulation

Ability of P-gp to efflux Calcein AM is used to identify the molecules which interfere with P-gp transporter activity. About 10000 cells of DU145TXR prostate cancer cells were seeded in each well in 96 well plates and allowed to grow until confluency for 4-5 days. Then media was replaced with phenol red free RPMI media and cells were treated with indicated concentrations of TPH104s and 1 µg/mL of Calcein AM. Fluorescence measured after 60 minutes with excitation at 485/20 nm and at emission 535/20 nm using the BioTek Cytation 5 imaging multi-mode reader (Bio-Tek, Winooski, VT). DMSO (0.5% v/v) was used as the vehicle, and 15 µM of Pgp inhibitor SMU 45 was used as a positive control. (n=6 in each trial).

Hoechst 33342 Assay for BCRP Modulation

Ability of BCRP to efflux nuclear stain Hoechst 33342 was used to identify the molecules which interfere with BCRP transporter activity. About 14000 cells of MCF-7 M100 breast cancer cells were seeded in each well in 96 well plates and allowed to grow until confluency for 4-5 days. Then media was replaced with phenol red free RPMI media and cells were treated with indicated concentrations of TPH104s and 5 µg/mL of Hoechst 33342. Fluorescence measured after 60 minutes with excitation at 361/20 nm and at emission 497/20 nm using the BioTek Cytation 5 imaging multi-mode reader (Bio-Tek, Winooski, VT). DMSO (0.5% v/v) was used as the vehicle, and 0.5 µM of BCRP inhibitor, Ko143 was used as a positive control and 15 µM of P-gp modulator, verapamil was used as negative control.

Cellular Reactive Oxygen Species (ROS) Detection Assay

To assess the effect of TPH104 on the generation of ROS, a cell permeant, fluorogenic dye, 2',7'-dichlorofluorescin diacetate, $H_2DCFDA$, was used. A 5 mM stock solution was prepared using DMSO and PBS was used to prepare the 3 µM working solution of $H_2DCFDA$. The TNBC cells were seeded in a 6-well plate as described in the cell cycle assay. After overnight incubation, cells were incubated with different TPH104 (1, 2, 5 µM) or vehicle for 12 h or with 2 µM of paclitaxel (positive control) for 2 h. The $H_2DCFDA$ dye (3 µM) was added to each well and the plate was incubated for an additional 30 minutes. Subsequently, cells were washed 3 times in PBS to remove excess $H_2DCFDA$ dye. Thereafter, cells from each well were captured from randomly selected fields using a fluorescent microscope (EVOS-FLC cell imaging system, Thermofisher scientific) at 40× to determine the 2',7'-dichlorofluorescein (DCF) fluorescence intensity, which is positively correlated with the generation of ROS.

Acridine Orange Assay

The cell-permeant, nucleic acid binding dye, acridine orange (AO) was used to assess the effect of TPH104 on the activation of lysosomes. A 10 µg/ml stock solution was prepared using PBS. The TNBC cells were seeded in a 6-well plate as described in the cell cycle assay. After overnight incubation, cells were incubated with TPH104 (1, 2, 5 µM), vehicle or 20 uM of chloroquine (CQ, negative control) for 12 h. The media was removed via suction and 1 ml of AO, diluted in 1:1000 in PBS, was added to each well and the plate was incubated for an additional 30 minutes. Cells were washed three times in PBS to remove excess dye. The cells from each well were captured from randomly selected fields using a fluorescent microscope (EVOS-FLC cell imaging system, Thermofisher scientific) at 40× to determine the AO fluorescence intensity which is positively correlated to lysosomal activation.

Mitochondrial Membrane Potential Assay

This assay is a direct measure of the structural integrity of mitochondria. Cells were seeded as indicated in the cell cycle assay and incubated for 24 h at 37° C. The next day, TPH104 (0.5, 1, 2 µM) or vehicle and incubated with the cells for 12 h. The cells were harvested, washed 2× with PBS, counted, and their concentrations were adjusted to $5×10^6$ cells/well in the culture medium. Subsequently, 4 µl of the 10 µM solution of mitotracker red was added to each 1 ml aliquot of cells and incubated with the cells for 30 minutes at 37° C. The cells were washed 2× with PBS and re-suspended in the 100 µl of 1× annexin-binding buffer. The cells were stained with Alexa Fluor for 15 minutes and analyzed using flow cytometry as described in the manufacturer protocol (Thermofisher, USA).

Cell Lysis and Western Blot Analysis

The TNBC cells were seeded in a culture flask and incubated for 24 h. The cells were then incubated with different concentrations of the lead compounds and re-incubated for an additional 12 or 24 h. Next, the cells were harvested and total extracts (unless otherwise specified) were collected in a lysis buffer (1 M Tris-HCl, 3 M NaCl, 10.5 M EDTA, 10% NP-40, 10% Triton, 10% SDS) containing a protease inhibitor cocktail. The bicinchoninic acid (BCA) was used to determine protein concentration in the cell extracts (G-BIOSCIENCES, St. Louis, MO, USA). The extracted proteins were loaded onto a 10-15% SDS gels and after separation, the proteins were transferred from the gel to the PVDF membrane for assessment of protein expression. The membrane was blocked using 5% milk in Tris-buffered Tween 20 saline for 30 minutes. The membrane was then incubated overnight with primary antibodies against Bak, Bax, Bcl-2, caspase9, caspase 3, caspase 7, PARP, cytochrome c, N-cadherin, E-cadherin, c-Myc, dishevelled segment polarity protein 3 (DVL3), dishevelled segment polarity protein 2 (DVL2), Vimentin, mitogen-activated protein kinase kinase (MAPKK also known as MEK1/2), β-catenin, low-density lipoprotein receptor-related protein 6 (LRP6), receptor-interacting protein kinase (RIP), phosphorylated RIP (p-RIP), mixed lineage kinase domain like pseudokinase(MLKL), Caspase 8, light chain 3 (LC3), lysosomal-associated membrane protein 1 (LAMP1), unc-51 like autophagy activating kinase 1 (ULK1), ras associated protein 7 (Rab7), ras associated protein 5 (Rab5), Beclin 1, mechanistic target of rapamycin (mTOR), tumor necrosis factor alpha (TNF-α), tumor necrosis factor receptor 1 (TNFR1), tumor necrosis factor receptor 2 (TNFR2), Fas-associated protein with death domain (FADD), Fas ligand (Fas), TNF-related apoptosis-inducing ligand (TRAIL), death receptor 5 (DR5), Tumor necrosis factor receptor type 1-associated DEATH domain (TRADD), receptor-interacting protein kinase 3 (RIP3), β-actin or GAPDH in 1:1000 dilution in 5% milk or 5% BSA at 4° C. Horseradish peroxidase-labeled (HRP) anti-rabbit or anti-mouse secondary antibodies (1:5,000 dilution) were added and incubated the next day for an additional 1 h. A ChemiDoc™ MP System imaging system from Bio-Rad (Hercules, CA, USA) was used for blots reading. Blots were used to obtain the protein bands, followed by quantification of the bands using image J software (NIH, Bethesda, MD, USA). All of the data were expressed as the ratio of β-actin or GAPDH.

Statistical Analysis

All of the experiments were done in triplicate. The data from the cell cycle assay, MitoTracker Red and Alexa Fluor 488 annexin V assays and wound healing assay were analyzed by a two-way ANOVA, followed by Bonferroni's post-hoc analysis. The data from the colony formation assay, Western blots, DAPI staining, immunofluorescence, transwell migration and the TPH104 $IC_{50}$ values for the different cells lines were analyzed by a one-way ANOVA, followed by Tukey's post-hoc analysis. The results were represented as the means±the standard deviations (SD). The a priori significance level was $p<0.05$.

Results

TPH104 is Efficacious in TNBC and Other Cancer Cell Lines

Figure 2A:
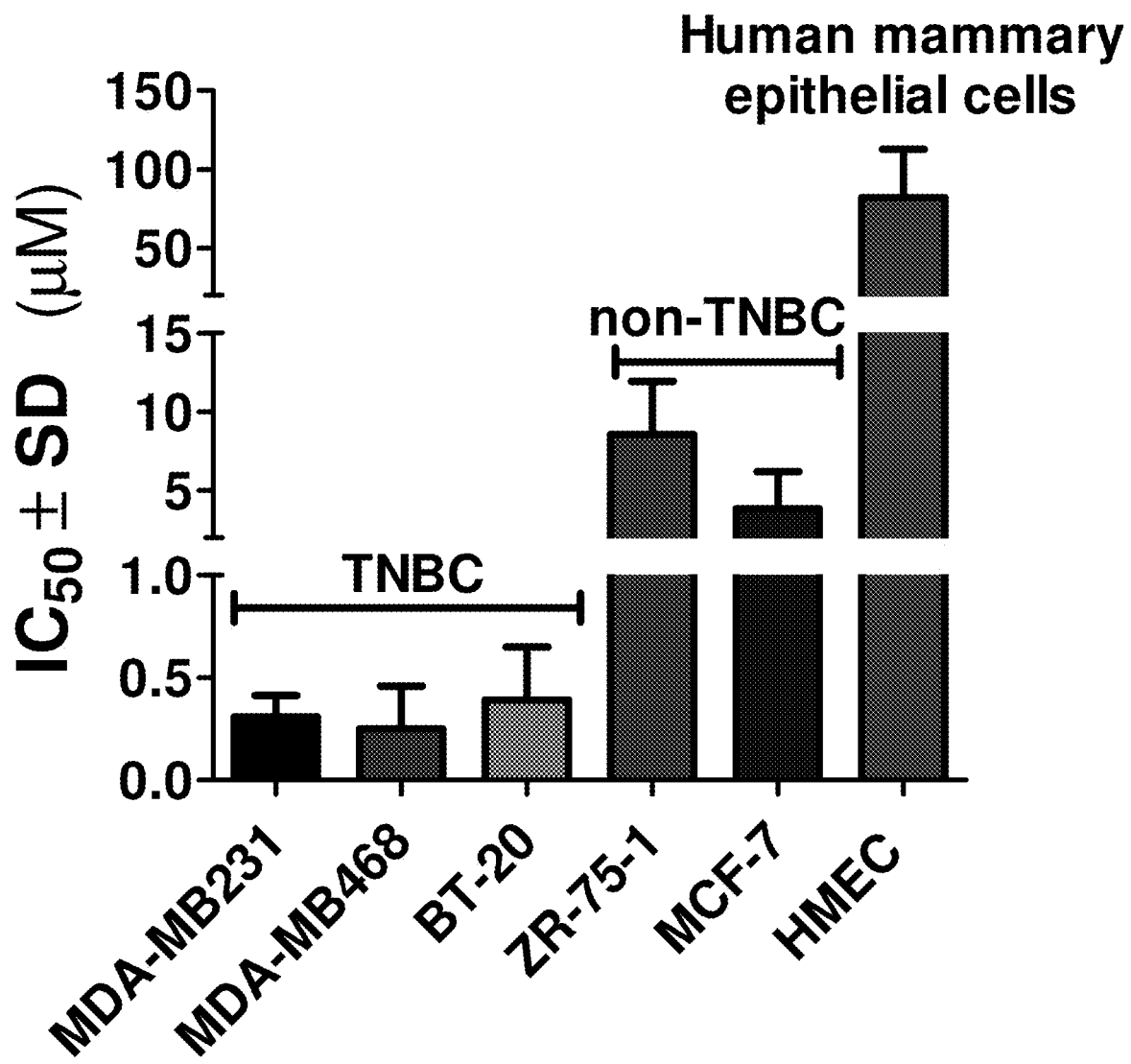
FIGS. 2A-2B: The effect of the TPH104 compound on the breast cancer cell lines.

FIG. 1 shows the chemical structures of the TPH compounds obtained from the initial screening of 200,000 compounds from the Specs database. Out of the nine compounds obtained, the compound TPH104 was the most selectively cytotoxic in TNBC cells. The $IC_{50}$ values of TPH104 to inhibit proliferation of the TNBC cell lines MDA-MB231, MDA-MB468, and BT-20 were 0.19, 0.25, and 0.29 µM, respectively (Table 1 and FIG. 2). In contrast, TPH104 was less potent in inhibiting the growth of the non-TNBC cell lines, ZR-75-1 ($IC_{50}$=8.6 µM) and MCF-7 ($IC_{50}$=3.8 µM) (Table 2 and FIG. 2). TPH104 also significantly inhibited the proliferation, although less potently, of other types of cancer, including lung (H460), ovarian (OV2008), prostate (DU145), and colon (HCT-116, LOVO, S1) (Table 3). In contrast, the $IC_{50\ of}$ TPH104 for normal human mammary epithelial cells (HMEC) was 82.3 µM, which was 330-411-fold higher than the $IC_{50}$ values for TNBC cells (FIG. 2A).

Table 2 (FIG. 29)-TPH104 compounds were tested for their cytotoxicity against TNBC and non-TNBC cell lines. Cell survival was determined using MTT assay as described in materials and methods. TPH104 had a significantly lower $IC_{50}$ against TNBC cell lines. The $IC_{50}$ values shown in this table are represented as mean±SD of three independent MTT experiments, each performed in triplicates.

Table 3 (FIG. 30)-Cytotoxicity screening of TPH104 compounds against Colon (HCT-116, LOVO and S1), Prostate (DU145), Ovarian (Ov 2008), and Lung (H460) cancer cell lines. Cell survival was determined using MTT assay as described. The $IC_{50}$ values shown in this table are represented as mean±SD of three independent MTT experiments, each performed in triplicates.

TPH104 Significantly Inhibits TNBC Colony Formation and Cell Proliferation

Figure 4:
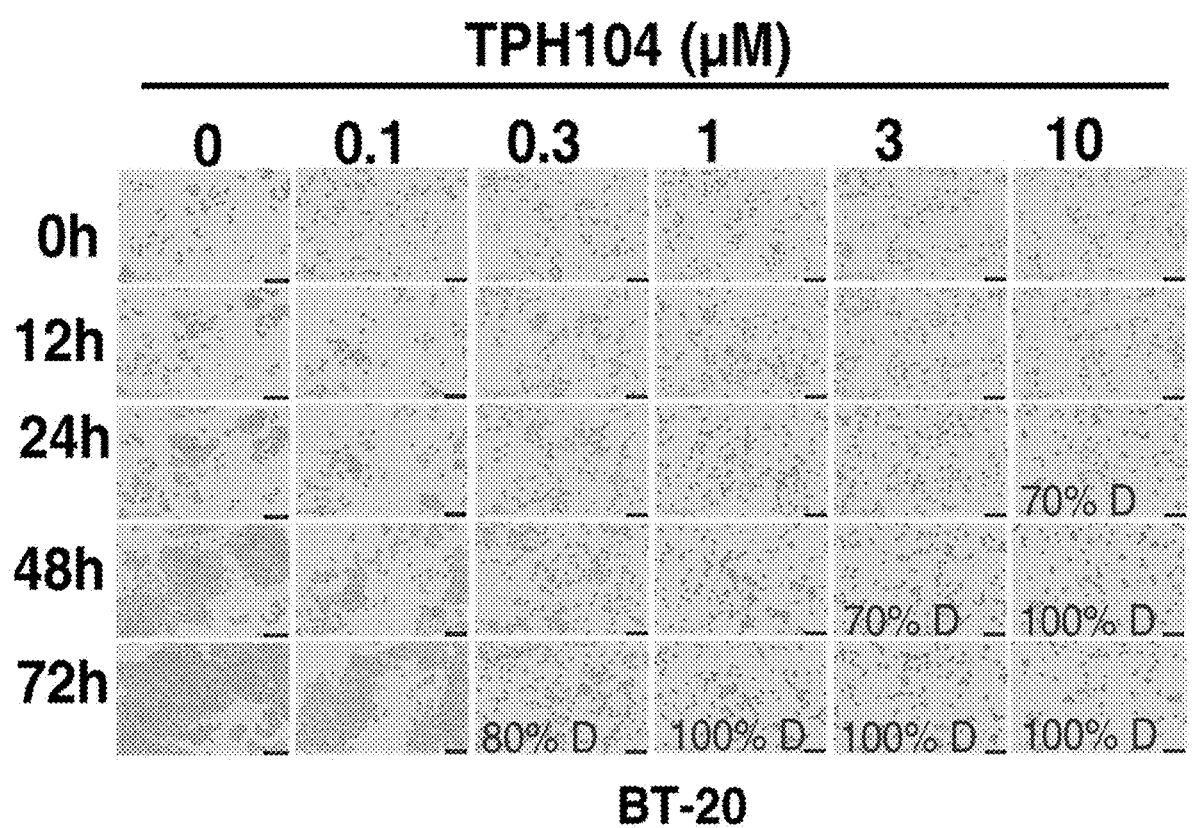
FIG. 4: Representative images of the anti-proliferative effect of TPH104 at different concentrations and different time points in BT-20 cells. The time lapse images were taken using an incuCyte live cell imaging instrument (10×). p<0.01, *p<0.001, ****p<0.0001 compared to the control.

The results indicated that TPH104 significantly decreased colony formation in TNBC cells (FIG. 3). TPH104 significantly inhibited colony formation rate in MDA-MB231, MDA-MB468, and BT-20 (FIG. 3A) compared to cells incubated with vehicle. Moreover, 1 µM and 10 µM of TPH104 produced a significantly greater reduction ($p<0.001$ and $p<0.0001$, respectively) in the colony formation rate compared to 0.1 µM of TPH104 in MDA-MB231 (FIG. 3B), MDA-MB468 (FIG. 3C), and BT-20 (FIG. 3D). TPH104 (1 µiM and 10 µM) also significantly decreased the number and the size of the colonies formed in all 3 TNBC cell lines (FIG. 3A) compared to cells incubated with vehicle ($p<0.001$). Moreover, in BT-20 cells, TPH104 (0.1, 1, 3, and 10 µM) produced a concentration-dependent and time-dependent decrease in BT-20 cell proliferation (FIG. 4). Overall, the above in vitro results indicate that TPH104 produces a concentration- and time-dependent anti-proliferative effect in the TNBC cell lines MDA-MB231, MDA-MB468, and BT-20

TPH104 Produces Cellular Arrest at the S-Phase of the Cell Cycle in TNBC Cells

Figure 5A:
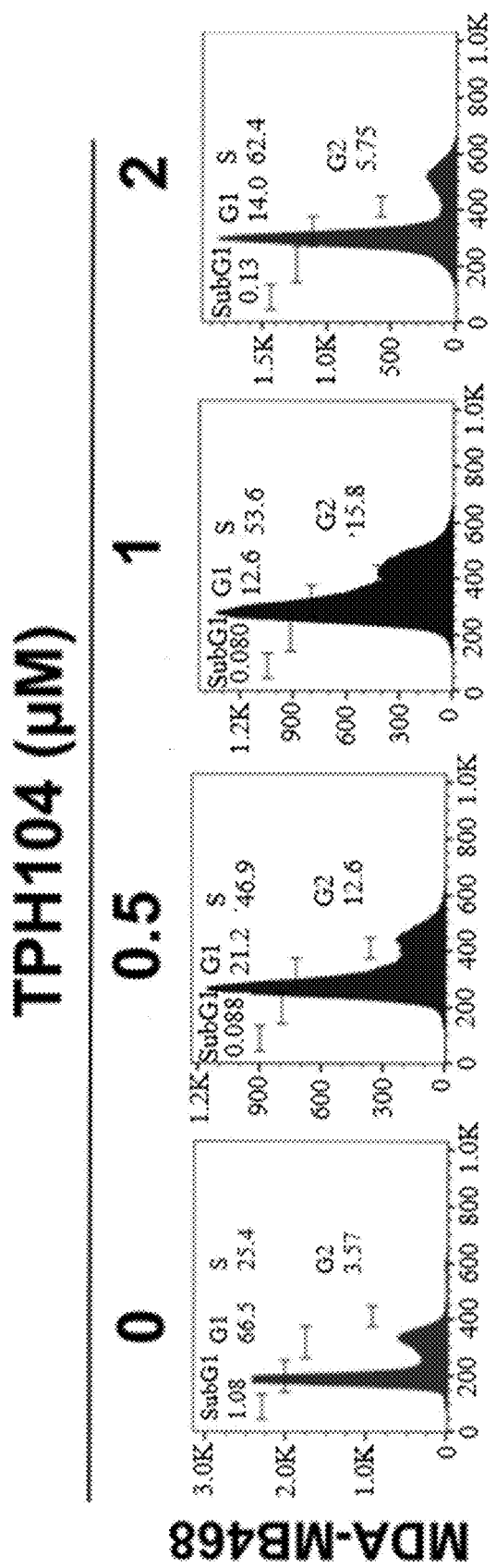
FIGS. 5A-5D: Cell cycle analysis of MDA-MB231 and MDA-MB468 cells incubated for 12 hr with different concentrations of TPH104 (0, 0.5, 1, or 2 μM).
Figure 5B:
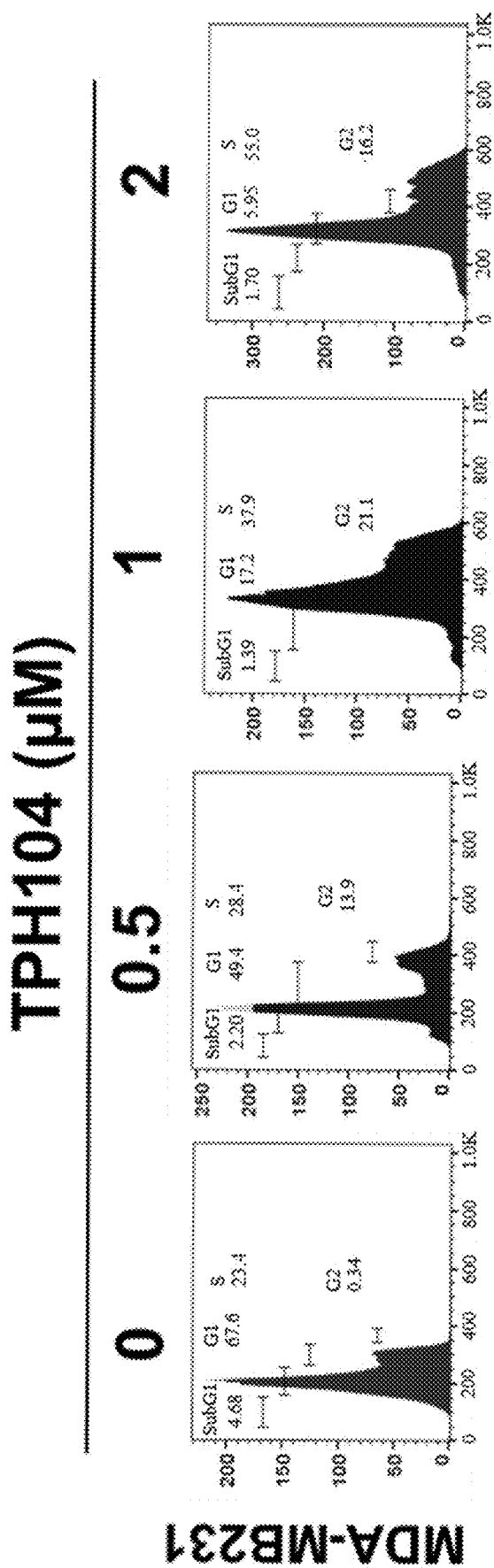
Figure 5C:
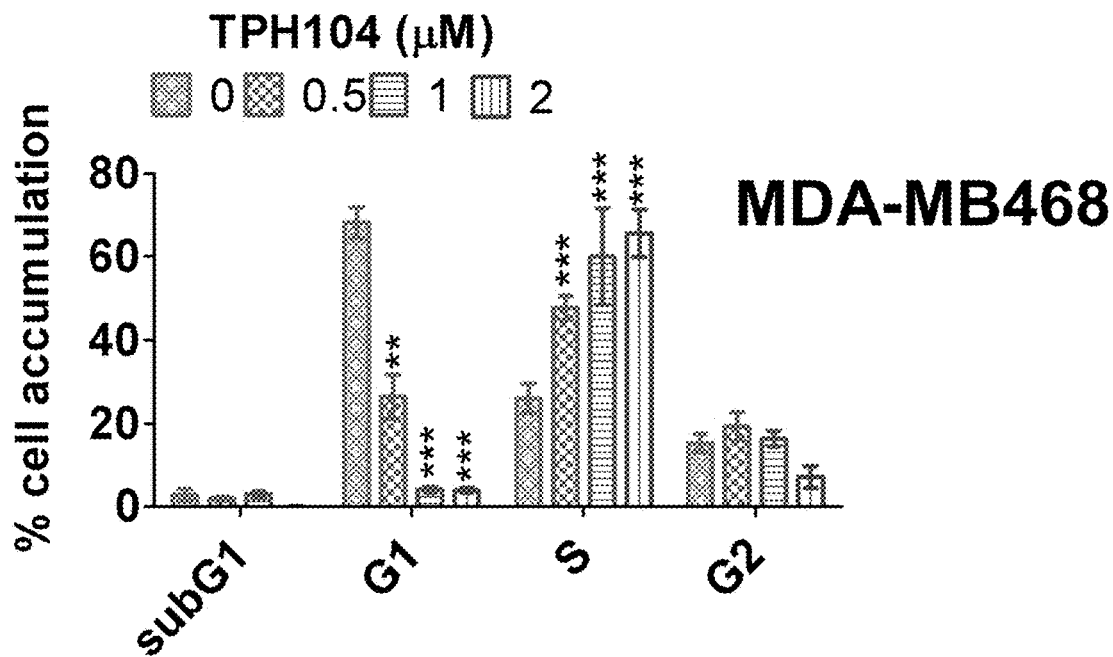
Figure 5D:
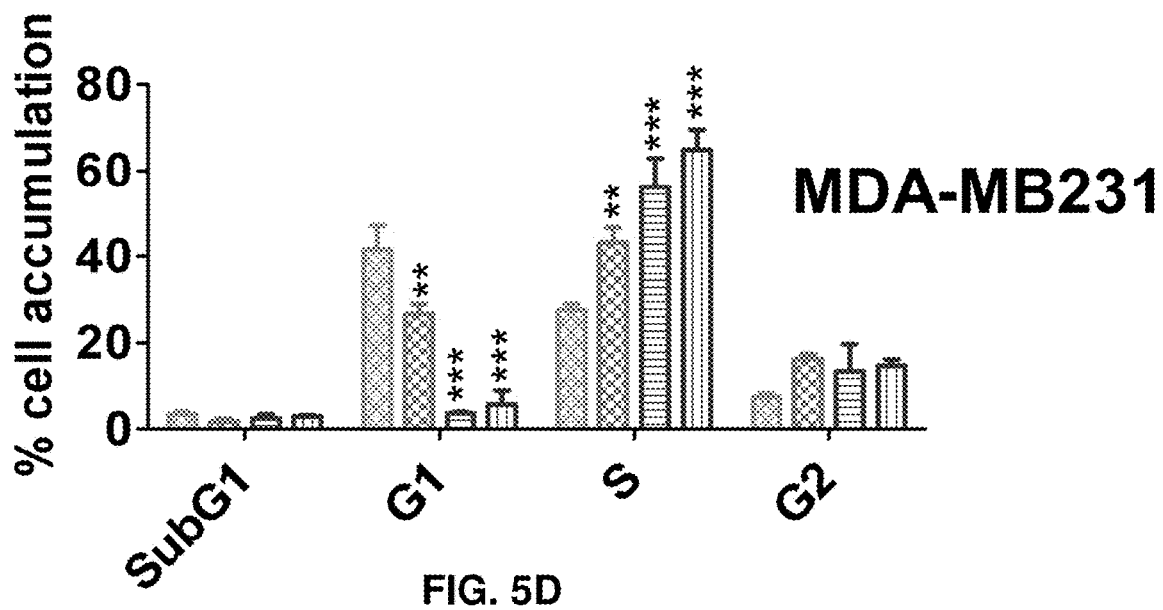

TPH104 significantly disrupted the cell growth process and elicited cellular arrest at the S-phase of the cell cycle. TPH104 significantly increased the level of cells arrested in the S phase in MDA-MB468 (FIG. 5A) and MDA-MB231 (FIG. 5B) in a concentration-dependent manner, 0.5 µM ($p<0.001$), 1 ($p<0.0001$), and 2 µM ($p<0.0001$). In addition, TPH104 induced a significant reduction in the number of cells in the G1 phase (FIGS. 5C-5D, $p<0.001$ for 0.5 µM and $p<0.0001$ for 1 and 2 µM of TPH104). These results indicate that TPH104 inhibits cell proliferation and growth by blocking cell cycle at the S phase and reducing the number of cells in the G1phase in TNBC cells.

Figure 8A:
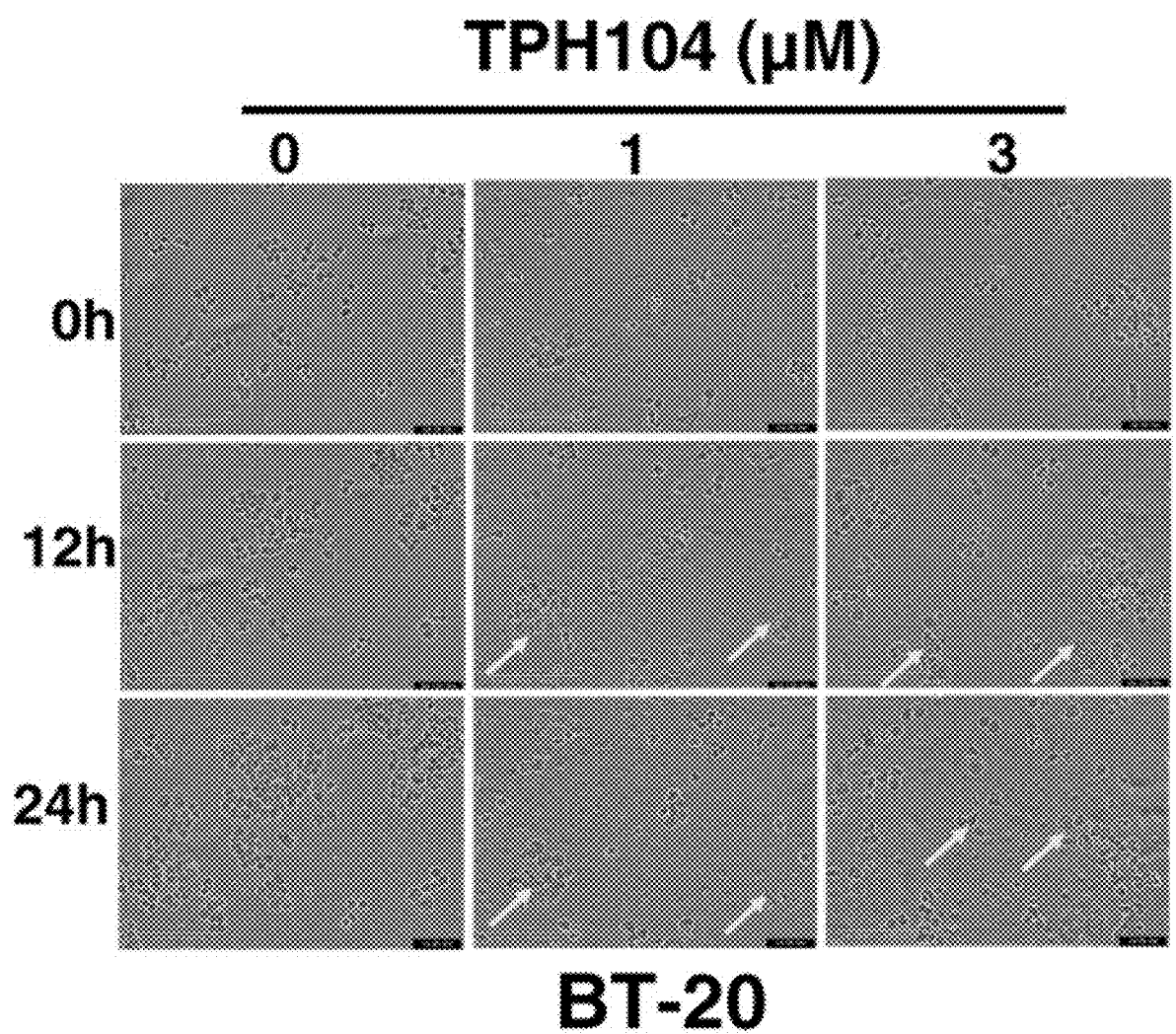
FIGS. 8A-8B: Representative images of morphological changes in BT-20 TNBC cells incubated with 0, 1, or 3 μM of TPH104 (FIG. 8A). The images were taken using an incuCyte live cell imaging instrument.
Figure 8B:
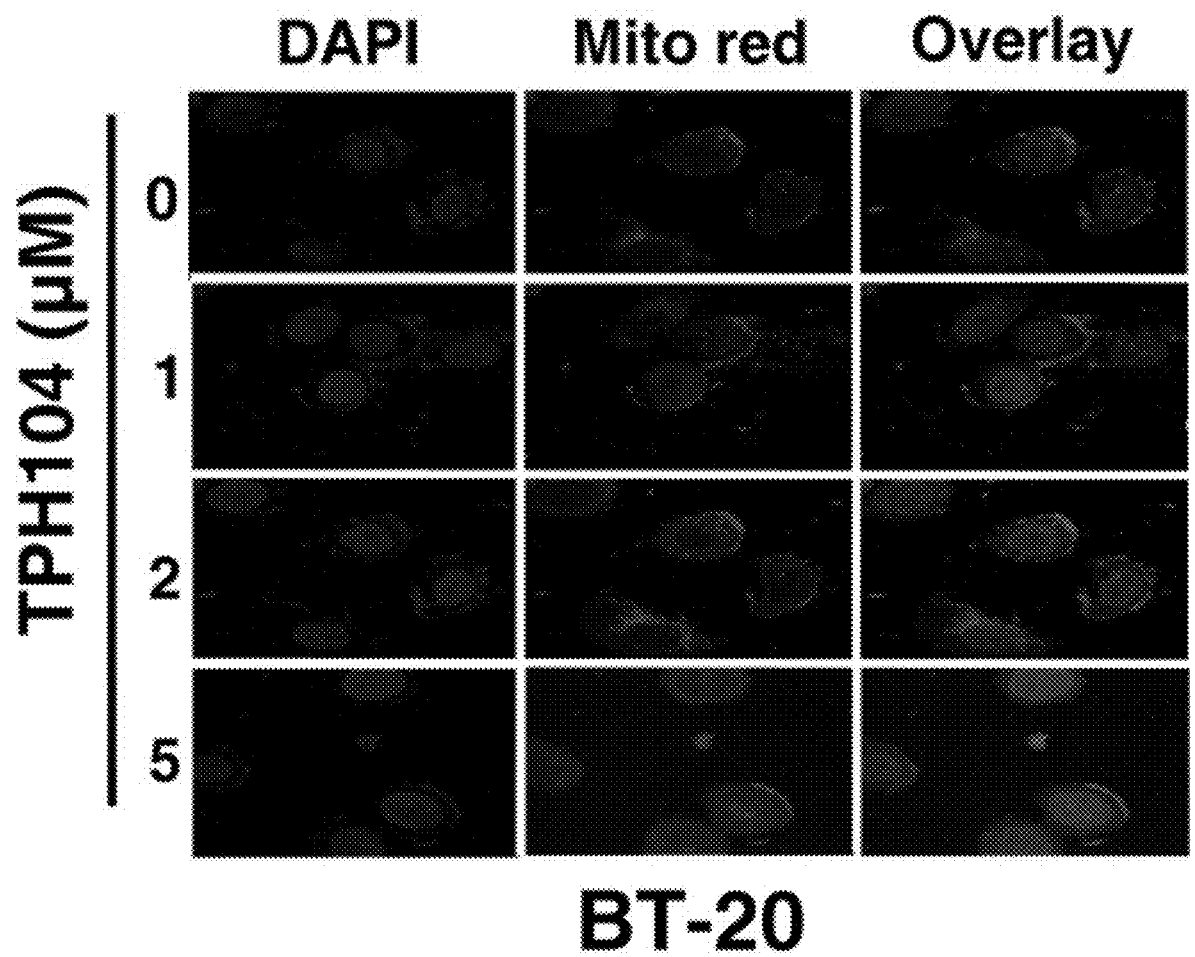

TPH104 Inhibits Apoptosis in a Concentration—Dependent Manner by Inhibiting the Intrinsic Apoptotic Pathway Experiments were conducted to determine if TPH104 was causing TNBC cell death by apoptosis. The incubation of BT20 TNBC cells with TPH104 (1, 2, and 5 µM) did not show nuclear condensation, a hallmark of apoptosis, as shown in FIG. 8B. Furthermore, TPH104 (1 µM and 3 µM) did not induce cellular shrinkage, but it did induce rupture of the cellular membrane in BT-20 cells compared to cells incubated with vehicle (FIG. 8A). Similarly, TPH104 did not produce nuclear condensation or cellular shrinkage in MDA-MB468 cells.

Figure 6A:
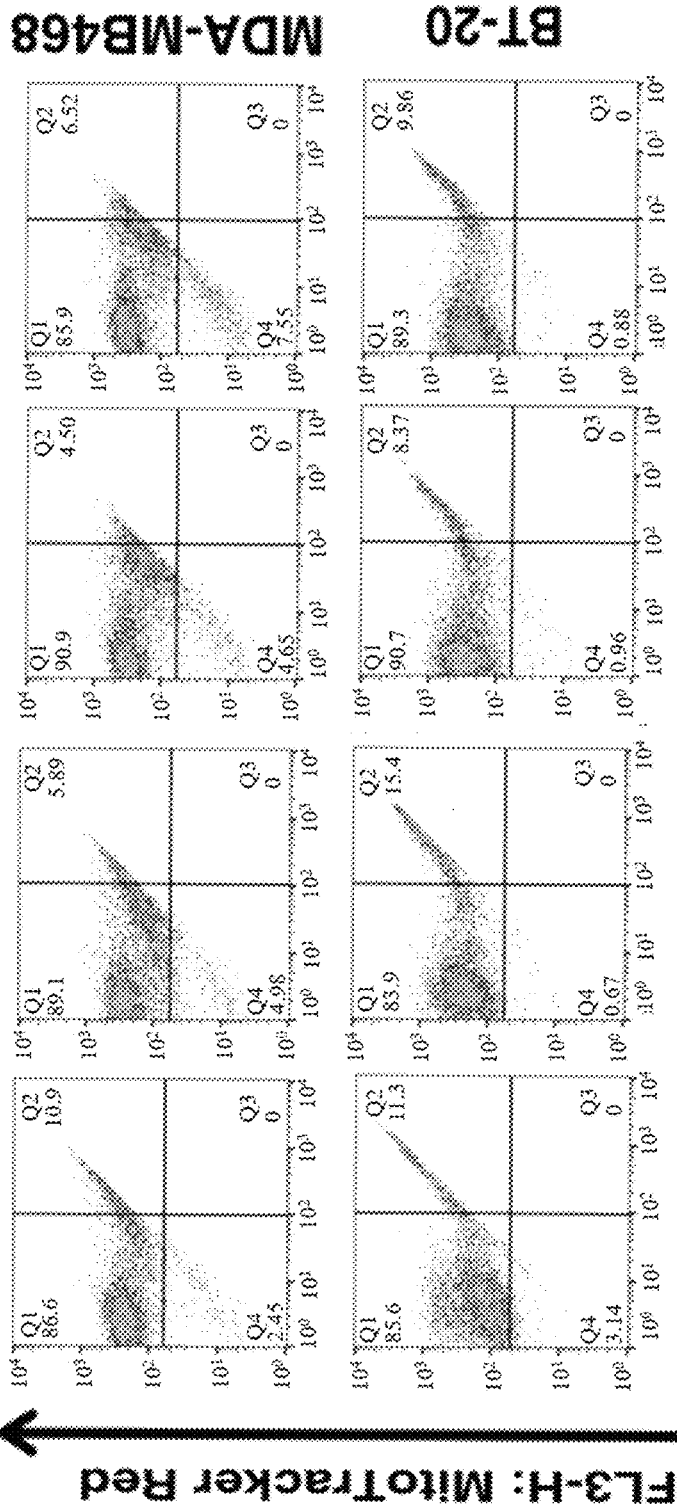
FIGS. 6A-6B: TPH104 does not induce apoptosis in either MDA-MB468 or BT-20 cell lines. MitoTracker Red and Alexa Fluor 488 annexin V kit were used to detect changes in the % of cells in each quadrant (Quad).
Figure 6B:
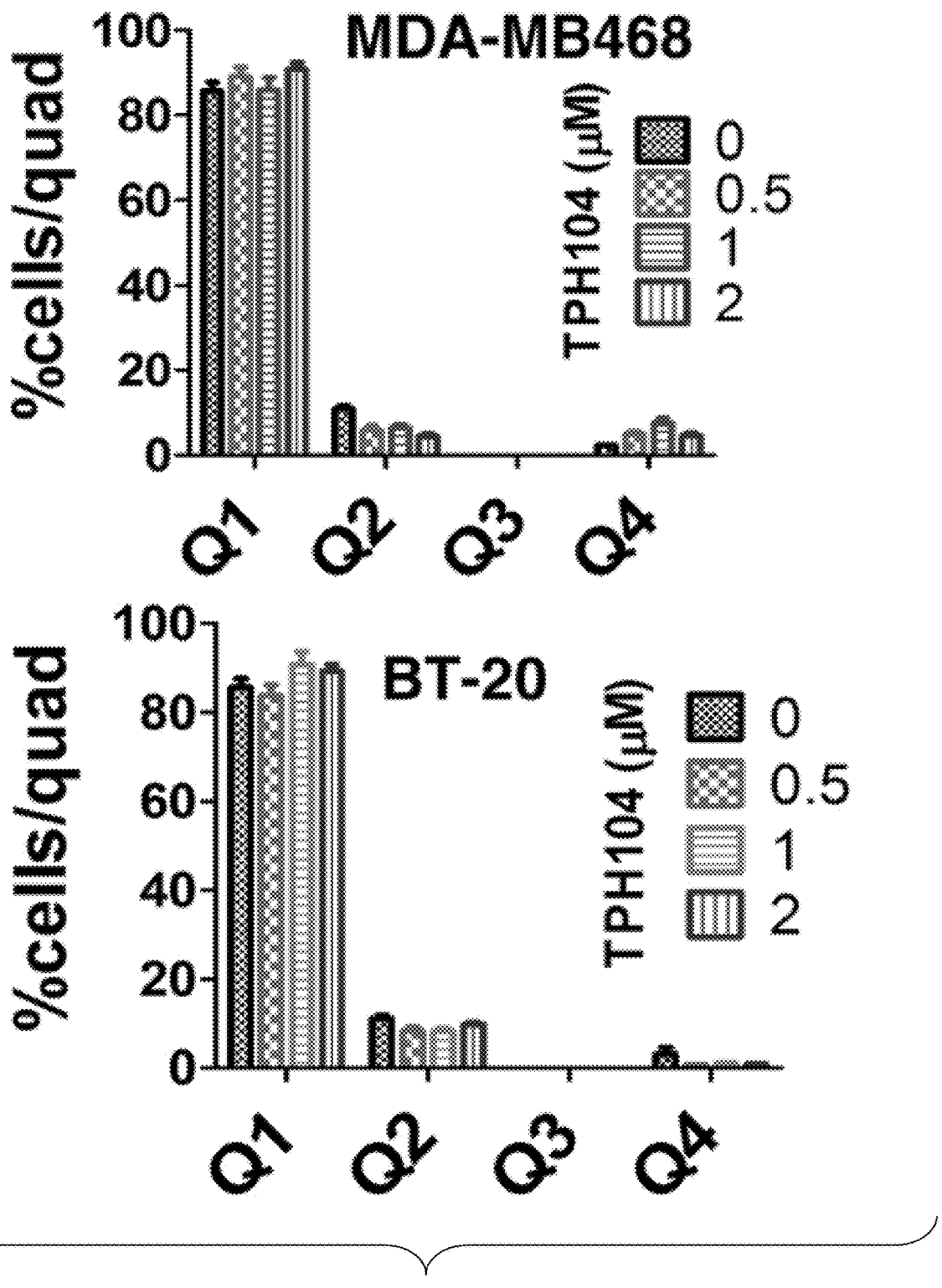
Figure 7A:
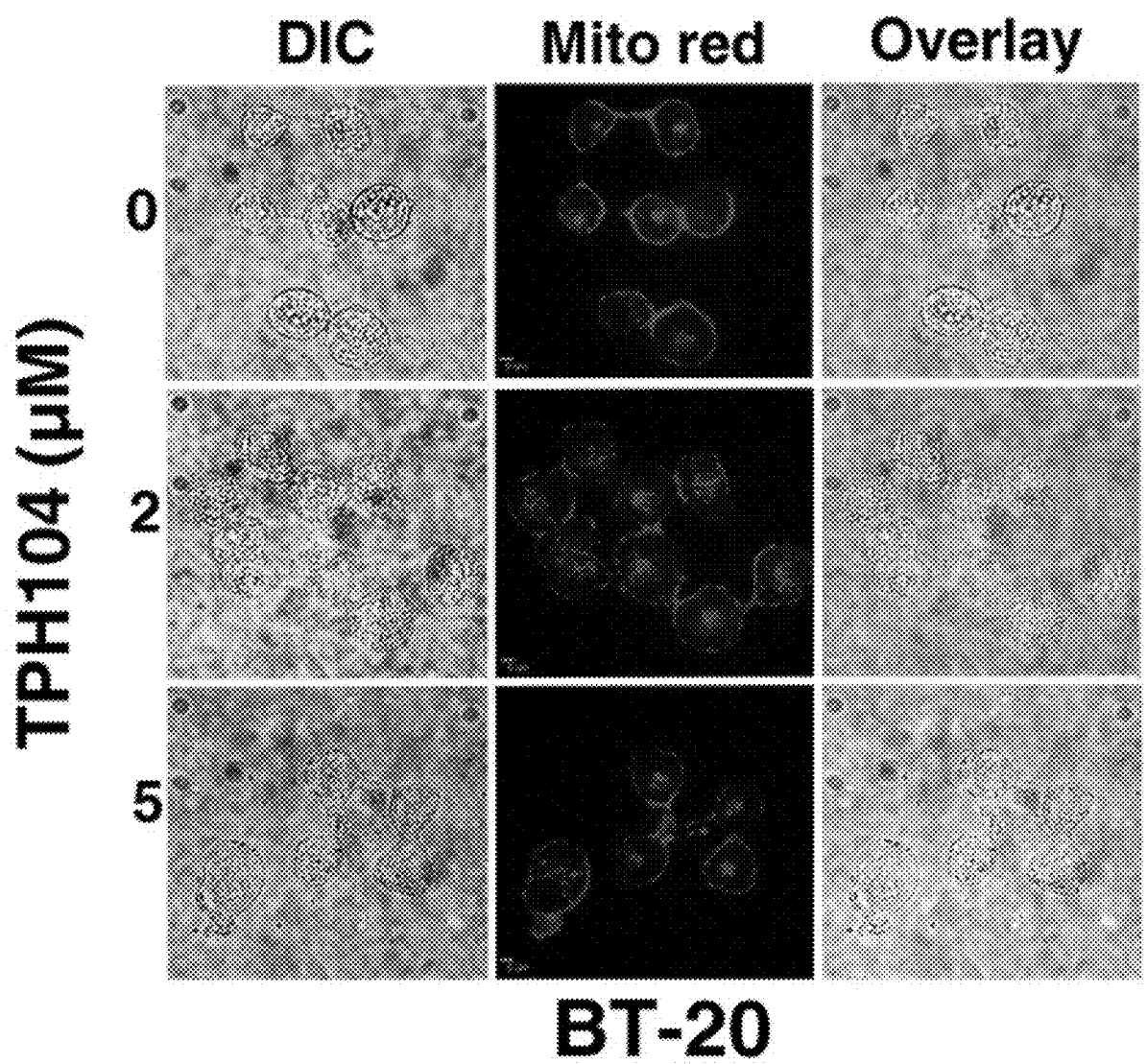
FIGS. 7A-7B: Representative images of BT-20 and MDA-MB468 cell lines incubated with 0, 2, or 5 μM of TPH104 and stained with MitoTracker red (Mito red). The images were taken at 60× using a confocal microscopy.
Figure 7B:
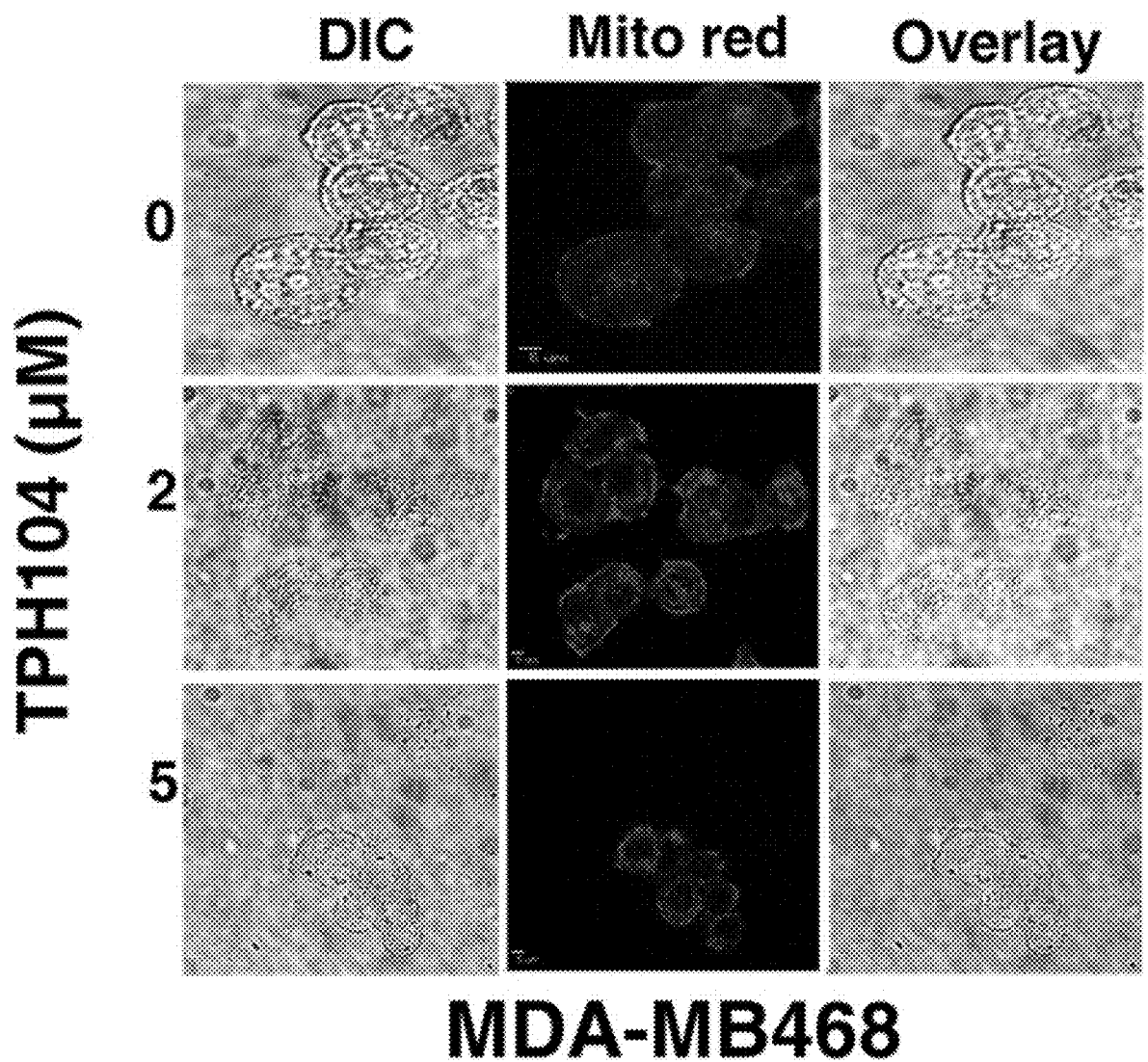

The effect of TPH104 on the mitochondrial membrane potential was also determined using the mitotracker red live cell imaging dye. Mitotracker red accumulates in mitochondria depending upon changes in the mitochondrial membrane potential. As shown in FIGS. 7A-7B, TPH104 (0.5, 1, and 2 µM) did not significantly alter the mitochondrial membrane potential in either BT-20 or MDA-MB468 cells. Mitochondrial depolarization occurs during the early stages of apoptosis. Therefore, the effect of TPH104 on mitochondrial depolarization was determined using flow cytometry to distinguish apoptotic from non-apoptotic cell populations. As shown in FIGS. 6A-6B, TPH104 (0.5, 1, and 2 µM) did not significantly alter the number of cells in the second quadrant (Q2), an area where apoptotic cells would be located. In both BT-20 and MDA-MB468 cells, non-apoptotic cells accumulated in the first quadrant, with little to no shift into Q2 (FIG. 6B).

Figure 9A:
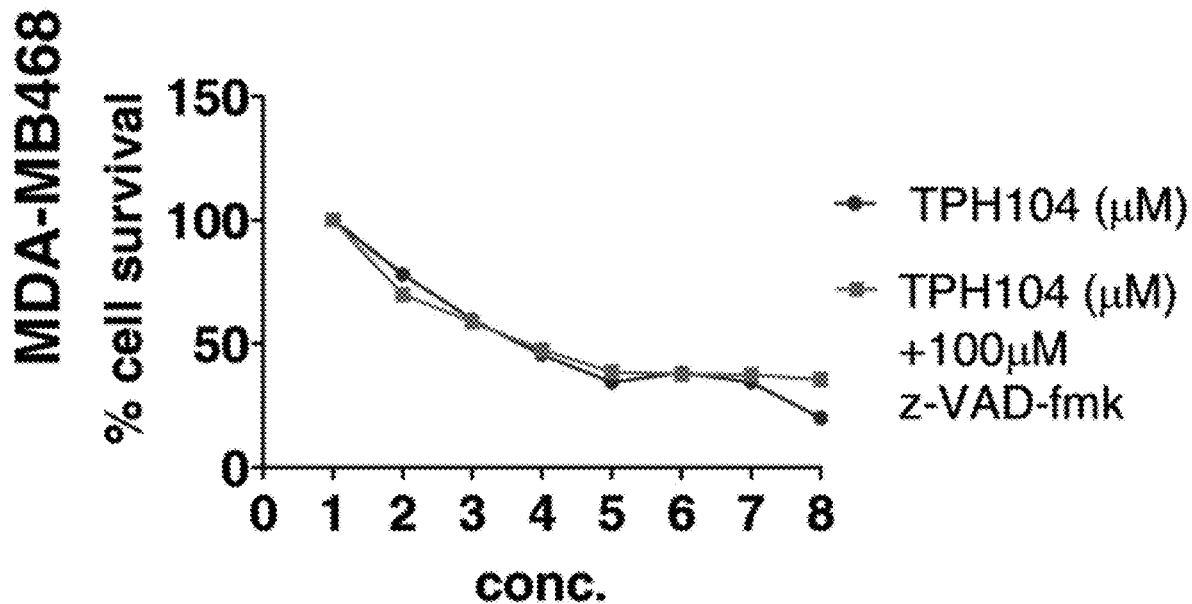
FIGS. 9A-9B: The cell survival curve of MDA-MB468 TNBC cells treated with TPH104 alone or in combination with 100 μM of z-VAD-fmk, a pan-caspase inducer (FIG. 9A).
Figure 9B:
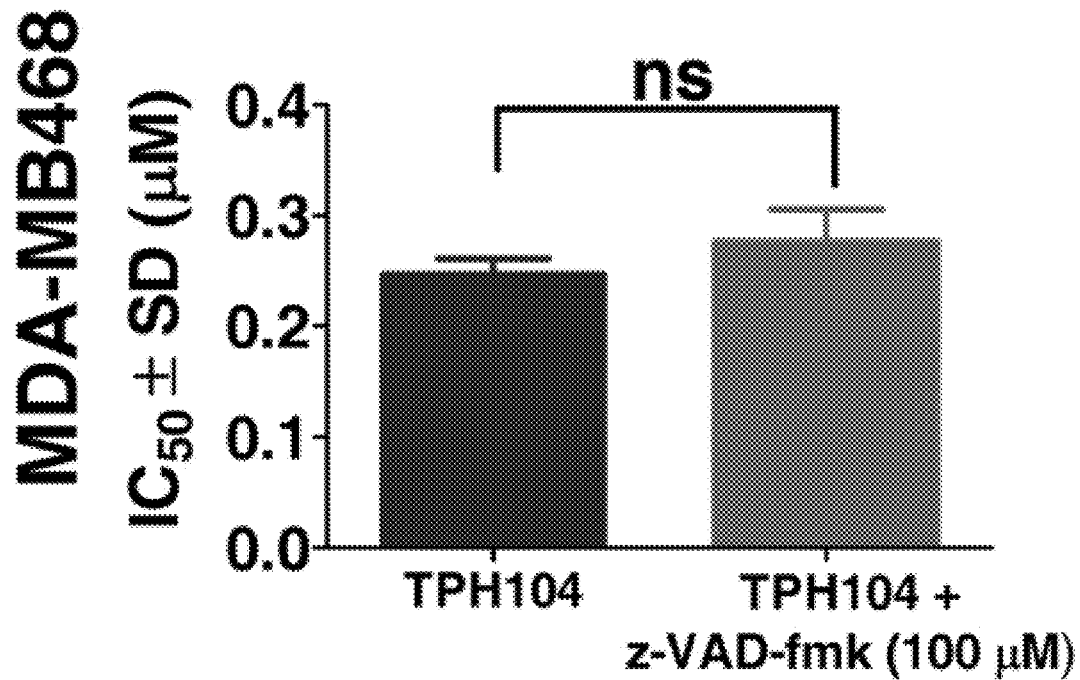

In addition, FIGS. 9A-9B show the cell survival curve and bar graph of the incubation of MDA-Mb468 TNBC cells with different TPH104 concentrations alone on in combination with z-VDA-fmk. Z-VAD-fmk, an apoptotic cell death inducer, did not significantly cause increase or decrease in the $IC_{50}$ of TPH104.

Figure 10A:
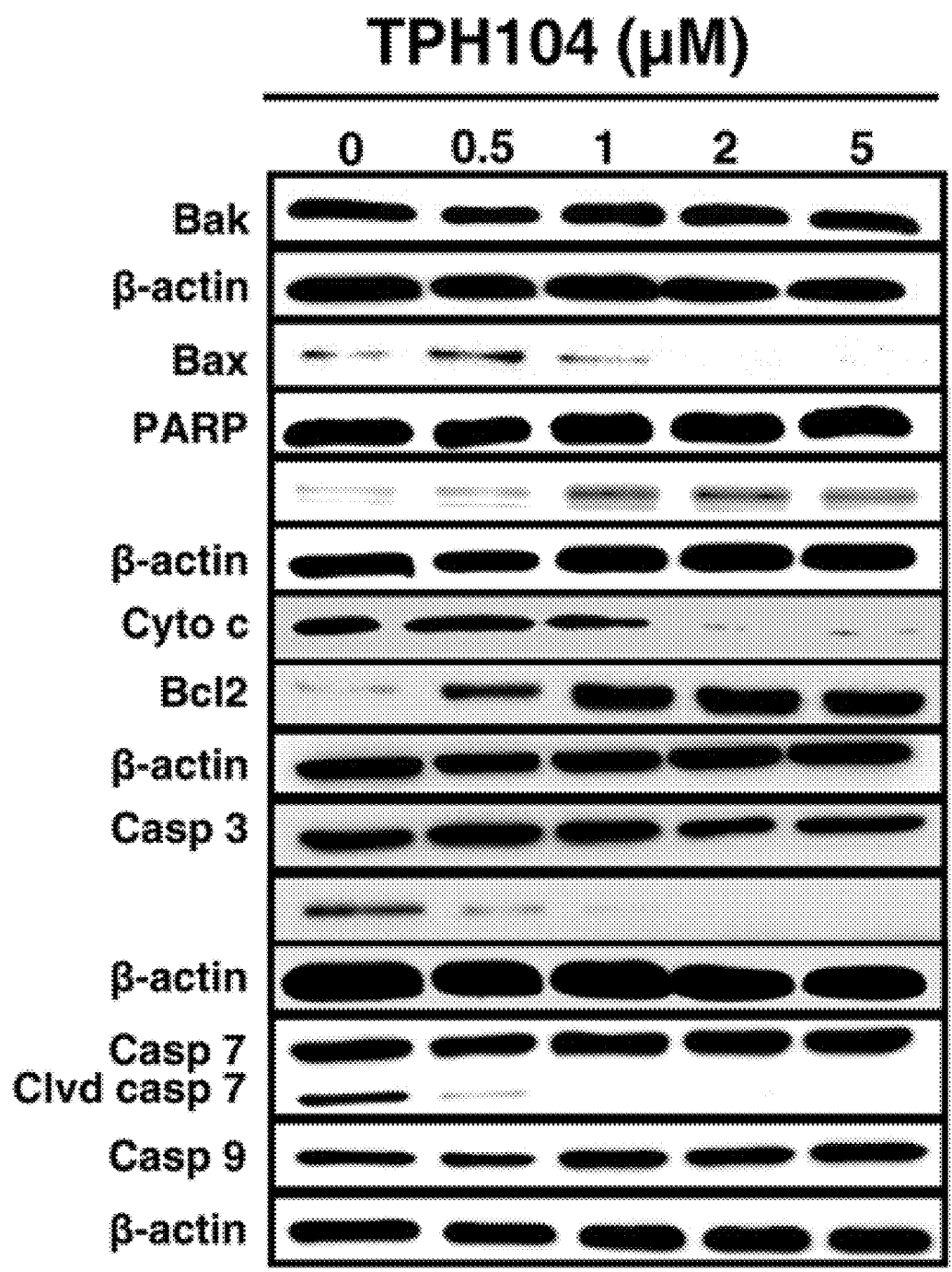
FIGS. 10A-10C: Western blots for the proteins Bak, Bax, PARP, cleaved PARP, Bcl-2, caspase 3, cleaved caspase-3, caspase 7, cleaved caspase 7, and caspase 9 in BT-20 cells following incubation with TPH104 (0, 0.5, 1, 2, or 5 μM) for 12 h (FIG. 10A). β-actin was used as a cytosolic reference protein and histone as a reference for nuclear proteins.

Furthermore, TPH104 (1, 2, and 5 µM), significantly decreased ($p<0.05$ for 1 µM, $p<0.01$ for 2 µM and 5 µM) the expression of Bax, a pro-apoptotic protein, in both BT-20 (FIGS. 10A-10B) and MDA-MB468 compared to cells incubated with vehicle. In contrast, compared to vehicle, the expression of Bak in BT-20 and MDA-MB468 cells was not significantly altered by TPH104 (0.5, 1, 2, and 5 µM), compared to cells incubated with vehicle. (FIG. 10A).

Figure 10B:
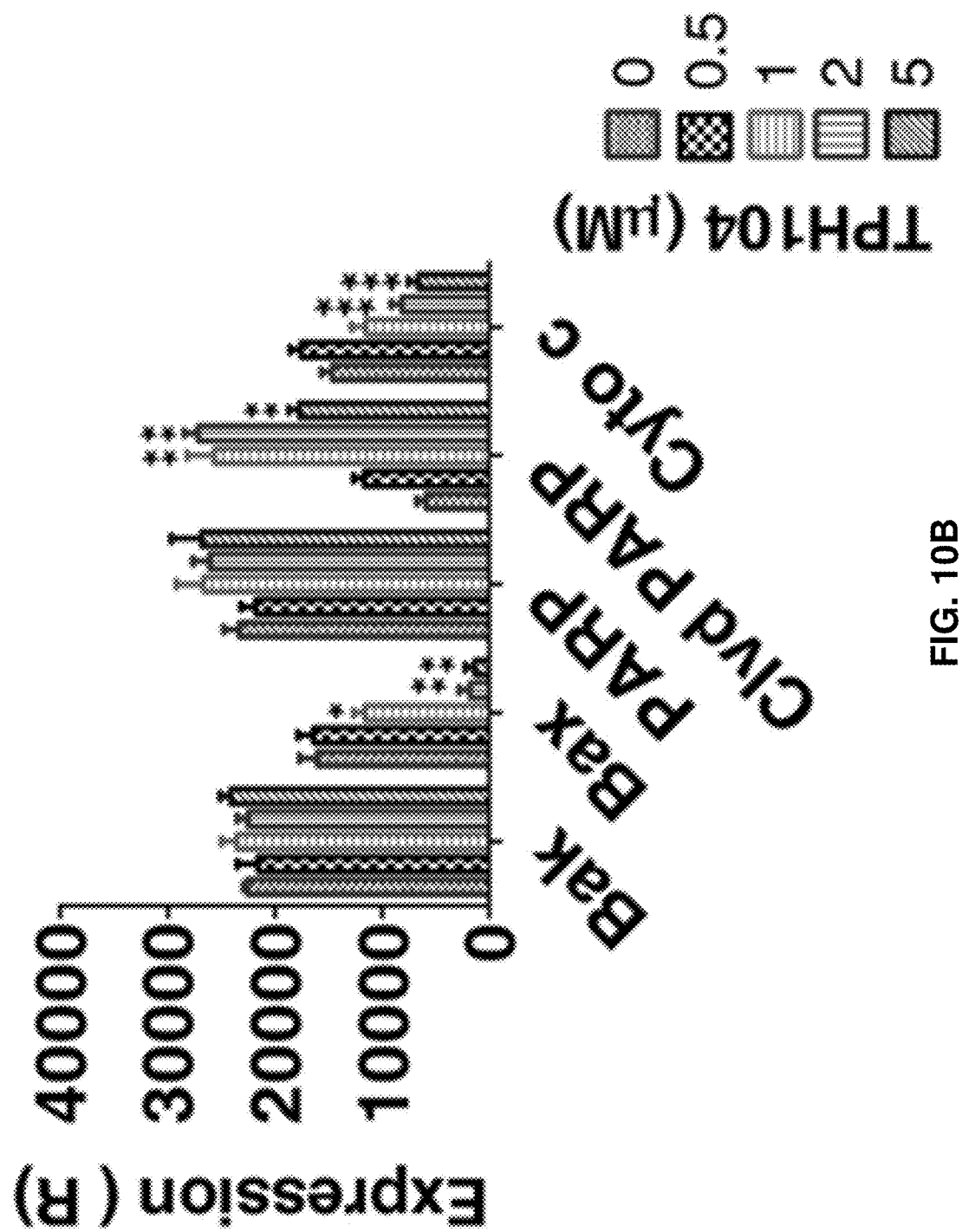
Figure 10C:
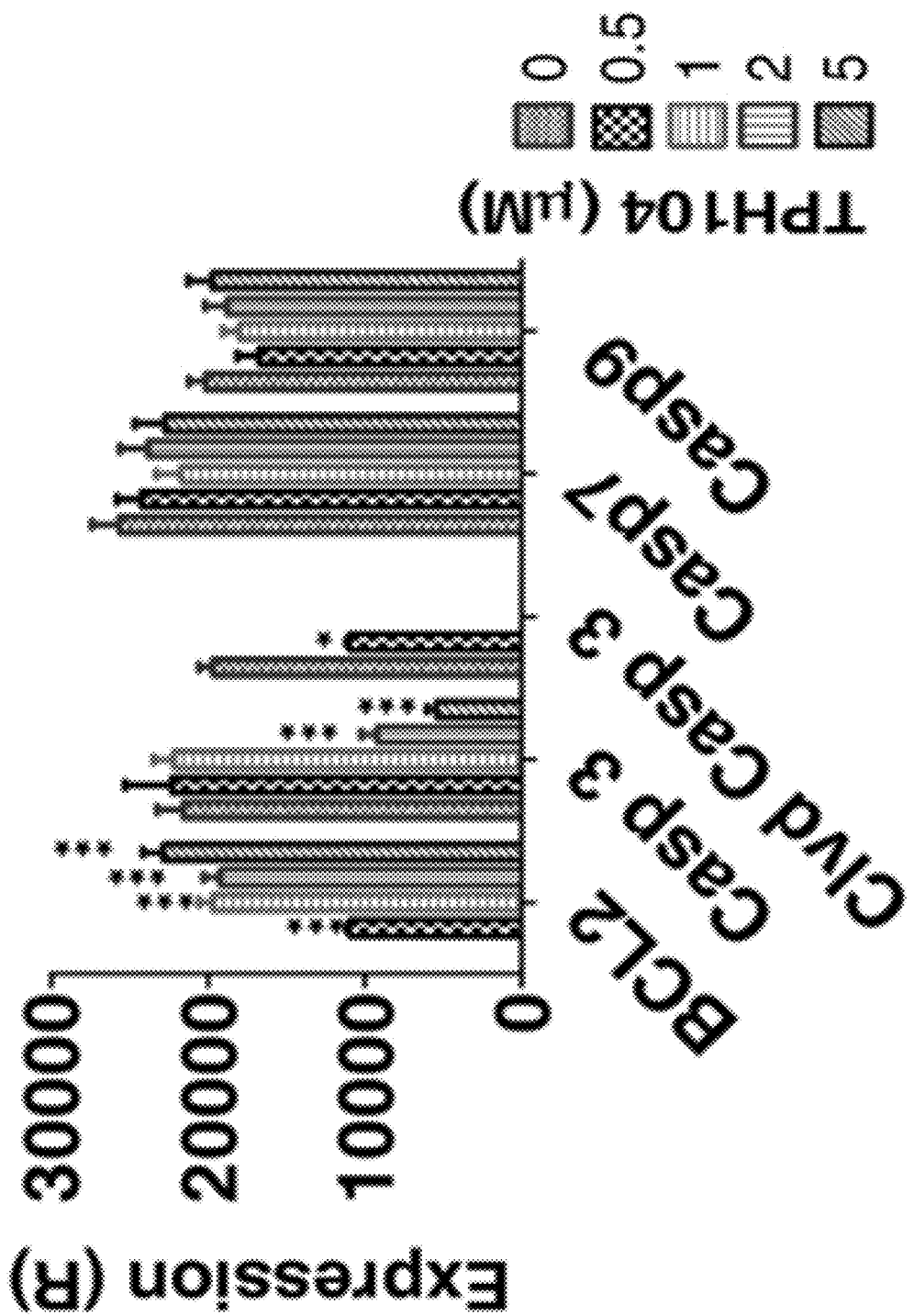

However, in BT-20 cells, TPH104 (0.5, 1, 2, and 5 µM), significantly ($p<0.001$) increased the expression of Bcl2 (FIGS. 10A-B) compared to cells incubated with vehicle. The effect of TPH104 on the expression level of caspase 3 and its substrate, PARP, was also deteremined. The incubation of BT-20 with 2 µM or 5 µM of TPH104 significantly decreased ($p<0.001$) the expression levels of caspase 3 and cleaved caspase 3 (FIG. 10A, 10C) compared to cells incubated with vehicle. The nuclear protein PARP, which is a substrate of caspase 3, was significantly cleaved in BT-20 TNBC cells by 1, 2, and 5 µM, of TPH104 ($p<0.01$) (show p values) (FIGS. 10A-10B) compared to the cells incubated with vehicle. In contrast, in BT-20 cells, TPH104 (0.5, 1, 2, and 5 µM) did not significantly alter the expression levels of caspase 7 and caspase 9 compared to cells incubated with vehicle (FIGS. 10A, 10C). In addition, TPH104 (1, 2, and 5 µM) significantly decreased the expression of cytochrome c in BT-20 ($p<0.001$) (FIGS. 10A-10B).

TPH104 Does Not Induce Oxidative Stress in TNBC Cells

Figure 11A:
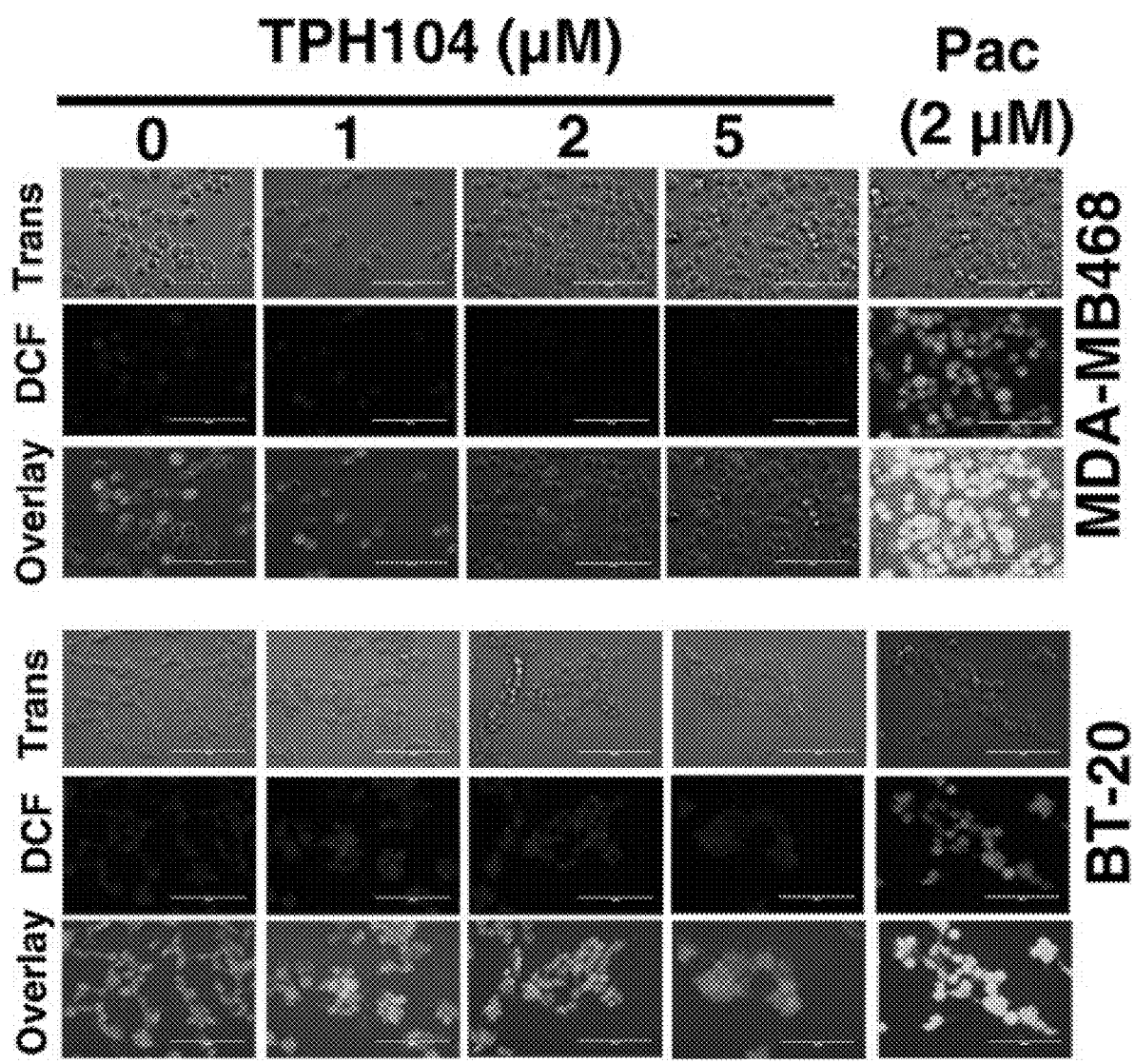
FIGS. 11A-11B: The incubation of MDA-MB468 and BT-20 cells with TPH104 (0, 1, 2 or 5 μM) did not significantly induce cellular oxidative stress.
Figure 11B:
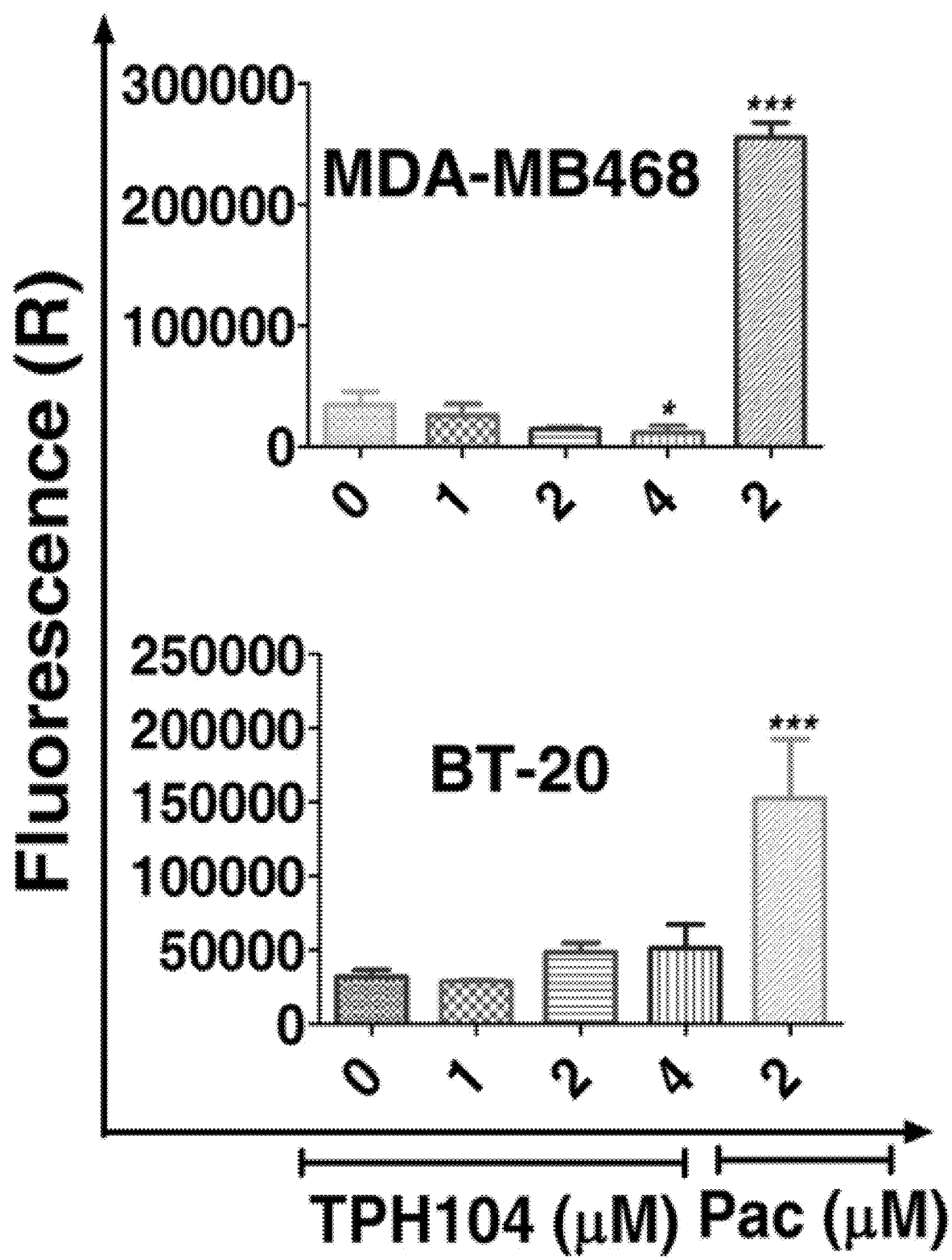

The incubation of BT-20 or MDA-MB468 cells with TPH104 (1, 2, and 5 µM) did not significantly alter DCF fluorescence levels compared to cells incubated with vehicle (FIGS. 11A-11B). In contrast, 2 µM of paclitaxel, which induces ROS generation in cancer cells, significantly increased DCF fluorescence compared to cells incubated with vehicle (FIG. 11B, $p<0.001$).

TPH104 Significantly Inhibits Invasion and Migration in TNBC Cells

Figure 12A:
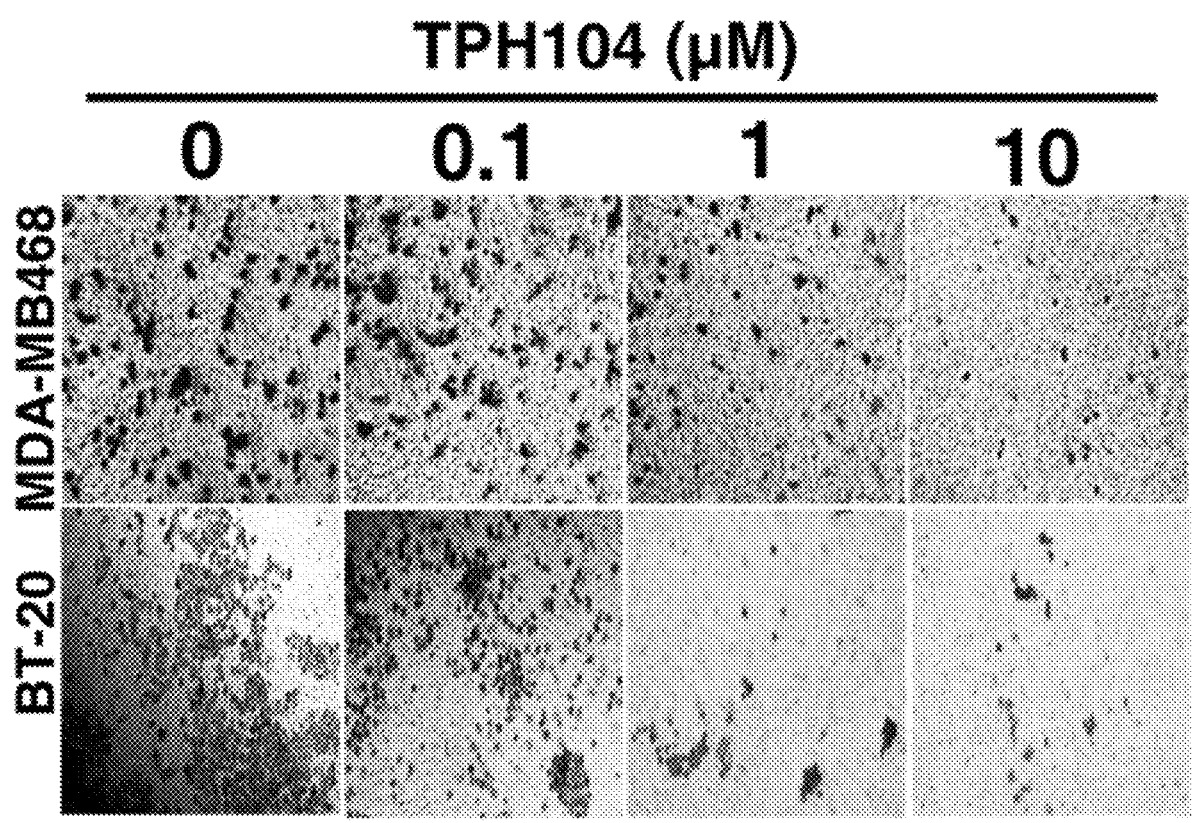
FIGS. 12A-12B: The in vitro effect of TPH104 on migration and invasiveness of BT-20 and MDA-MB468 cell lines and the expression of EMT/Wnt/beta-catenin proteins.
Figure 12B:
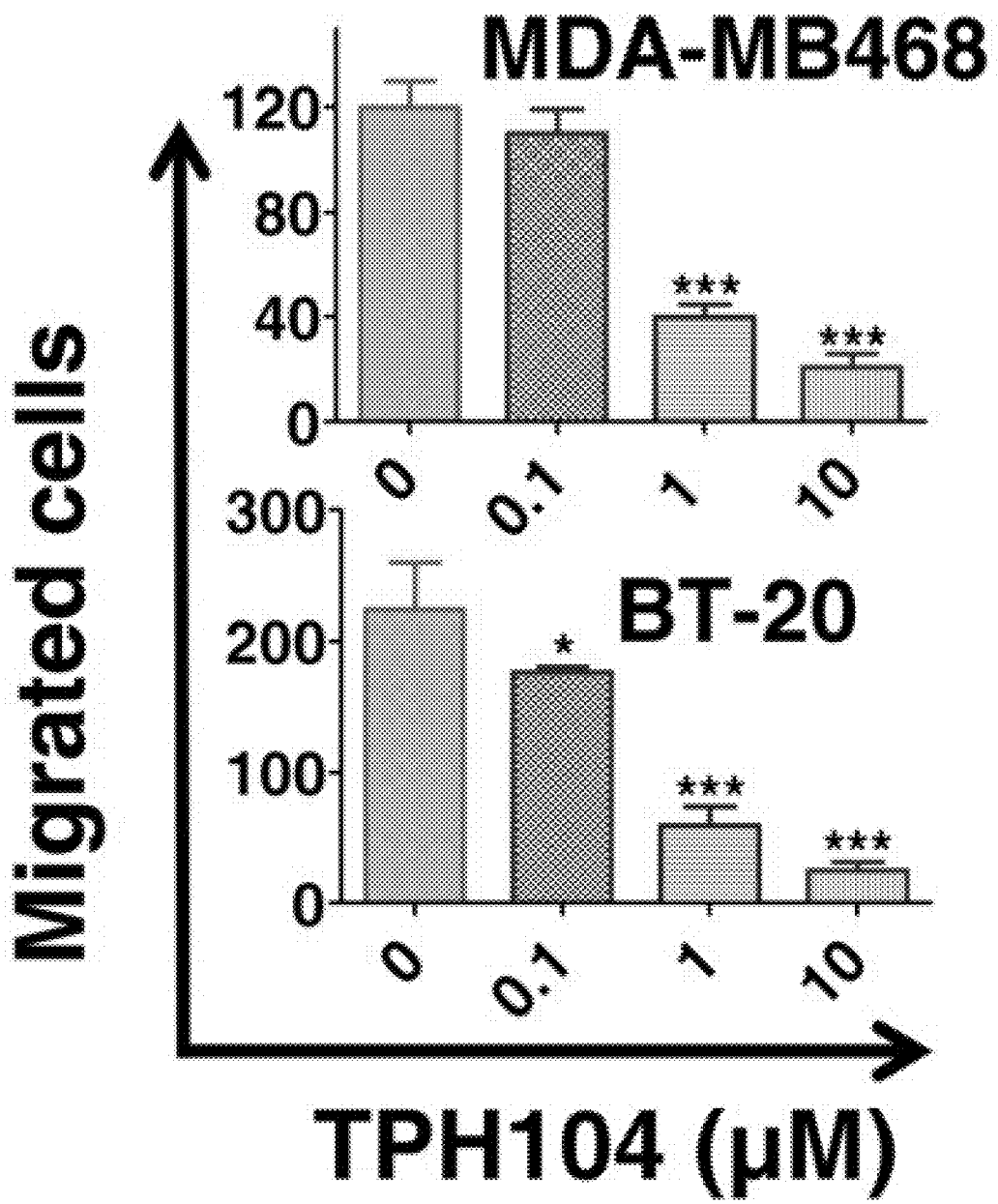

In order to evaluate the anti-metastatic efficacy of TPH104 in MDA-MB231, MDA-MB468, and BT-20 cells, in vitro cell-based assays were used to ascertain invasion and migration. TPH104 (1 µM or 10 µM) significantly decreased the migration of TNBC cells, MDA-MB468 (FIG. 12A). $p<0.001$), BT-20 (FIGS. 12A-12B, $p<0.001$), and MDA-MB231 in a concentration-dependent manner compared to cells incubated with the vehicle (FIG. 12B).

Figure 13A:
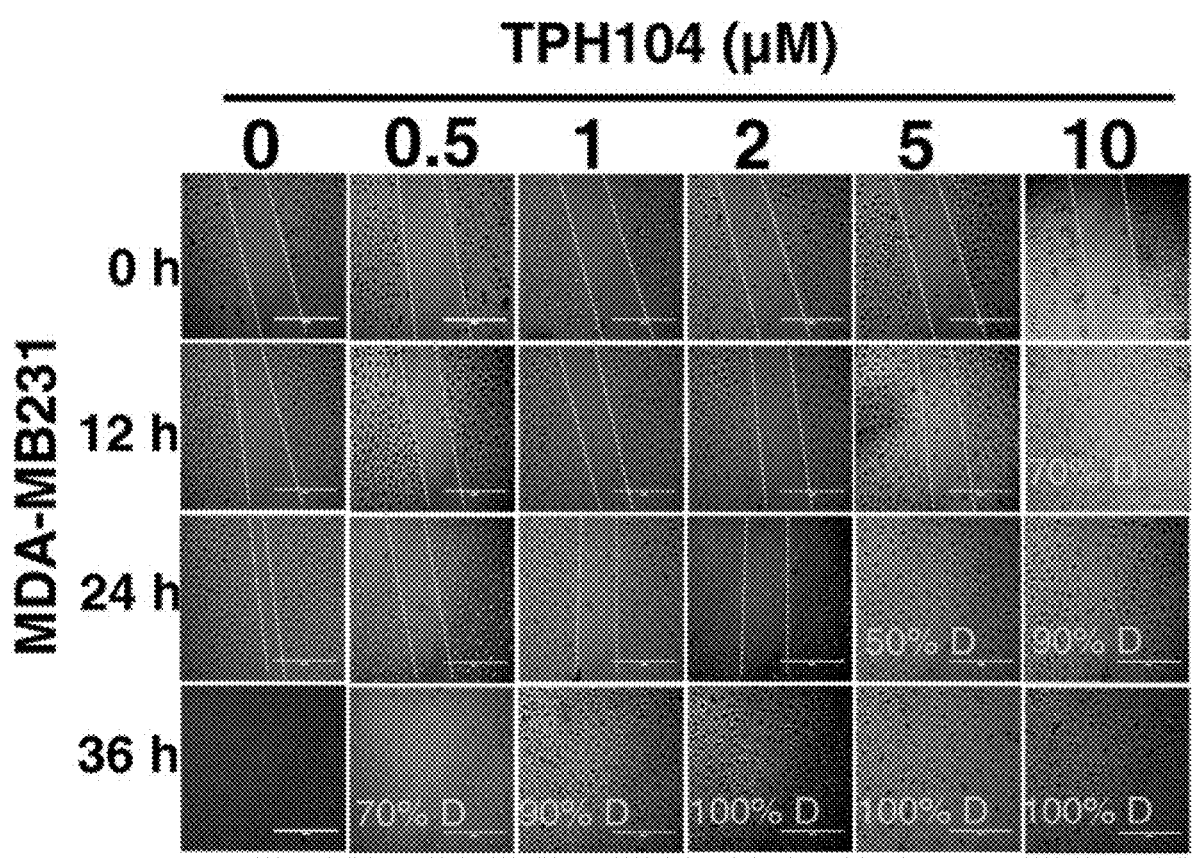
FIGS. 13A-13B: The in vitro effect of TPH104 on the migratory and invasive properties of MDA-MB231 TNBC cells using the wound healing assay.

In the wound healing assay, TPH104 (0.5, 1, 2, 5, and 10 µM) significantly decreased the mobility and migration of MDB-MB231 cells compared to cells incubated with vehicle (FIG. 13A). TPH104, at 10 µM, induced the death of 70% of the MDB-MB231 cells after 12 h of incubation compared to cells incubated with vehicle After 24 h of incubation with 5 µM or 10 µM of TPH104, the cells started to become detached and were floating, and after 36 h of incubation, the majority of the cells were completely detached and floating. In cells incubated with vehicle, complete wound closure occurred 36 h after the initial wound was created. However, wound closure was significantly reduced in MDA-MB231 cells incubated with 1, 2, 5, and 10 µM compared to cells incubated with vehicle and the cells were non-viable (FIG. 13A).

Figure 13B:
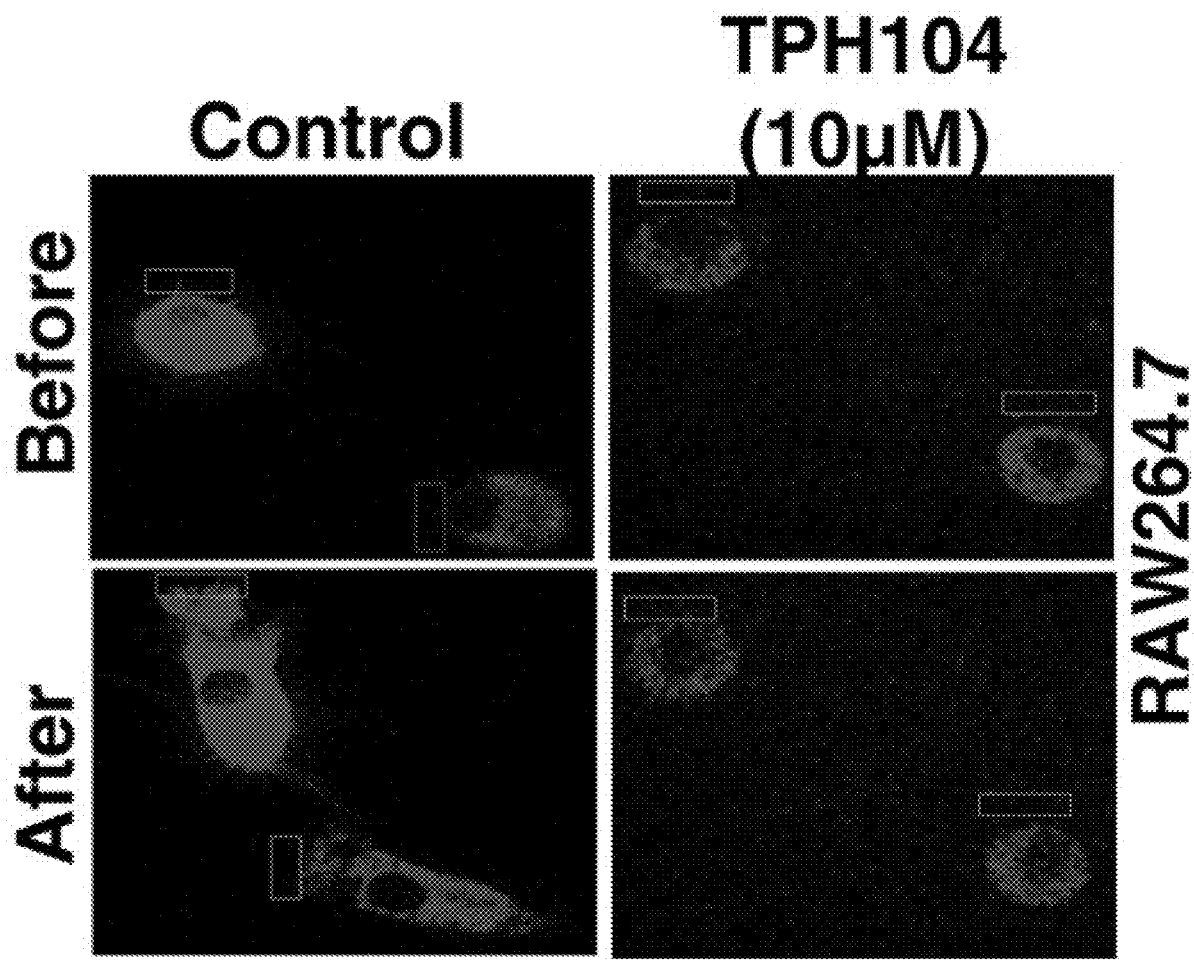

To further confirm the anti-migratory effect of TPH104, RAW264.7 macrophage cells were incubated with 10 µM TPH104 and its effect on Gai-coupled-GPCR activation was determined. As shown in FIG. 13B, incubation of RAW264.7 cells with 10 µM of TPH104 significantly decreased their migration in vitro.

Figure 14A:
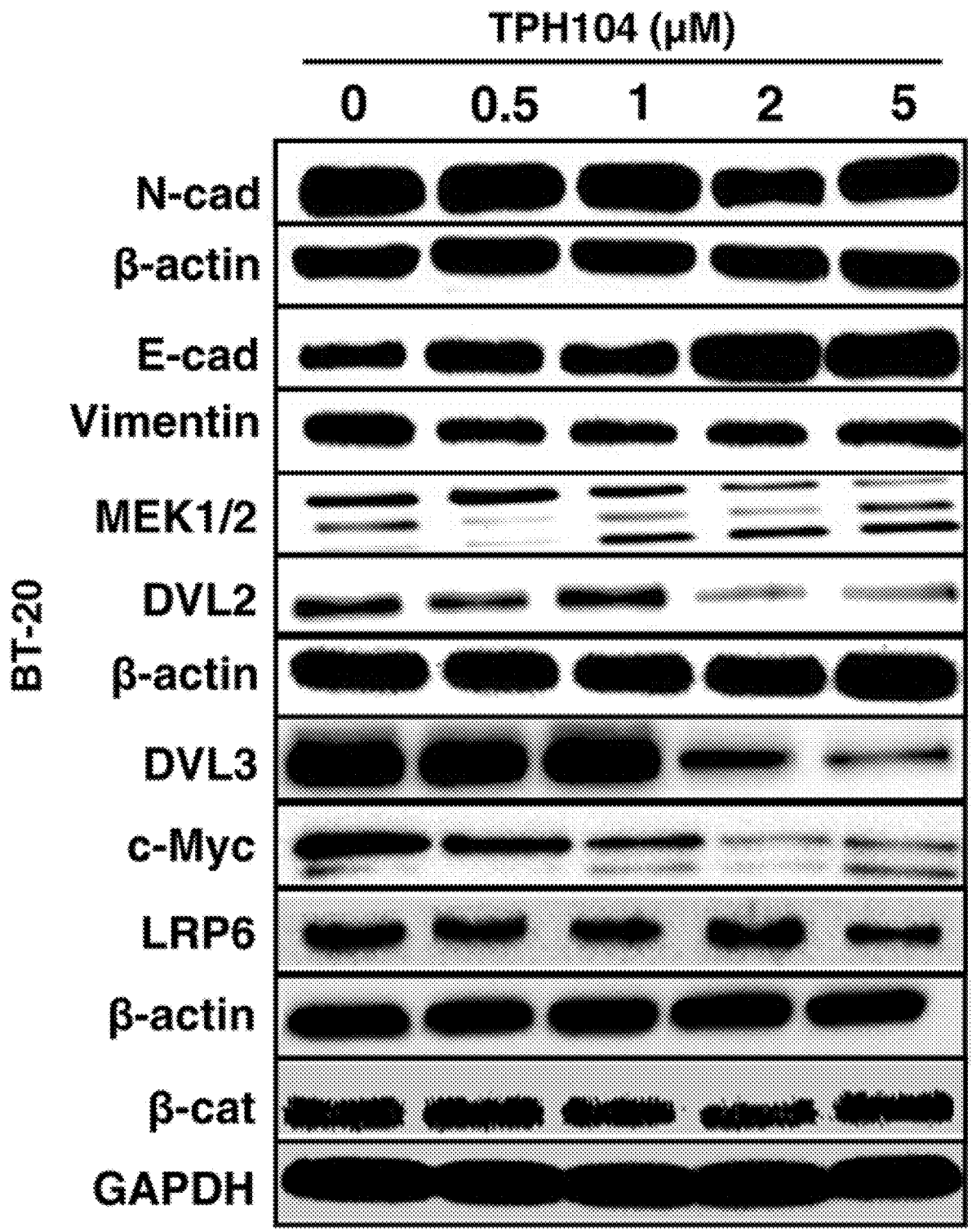
FIGS. 14A-14C: Western blot analysis for the expression of N-cadherin (N-cad), E-cadherin (E-cad), vimentin, MEK1/2, DVL2, DVL3, c-Myc, LRP6, and β-catenin (β-cat) (FIG. 14A). BT-20 cells were incubated with 0, 0.5, 1, 2, or 5 μM of TPH104. β-actin levels were used to normalize cytosolic proteins and histone was used for normalizing nuclear proteins.
Figure 14B:
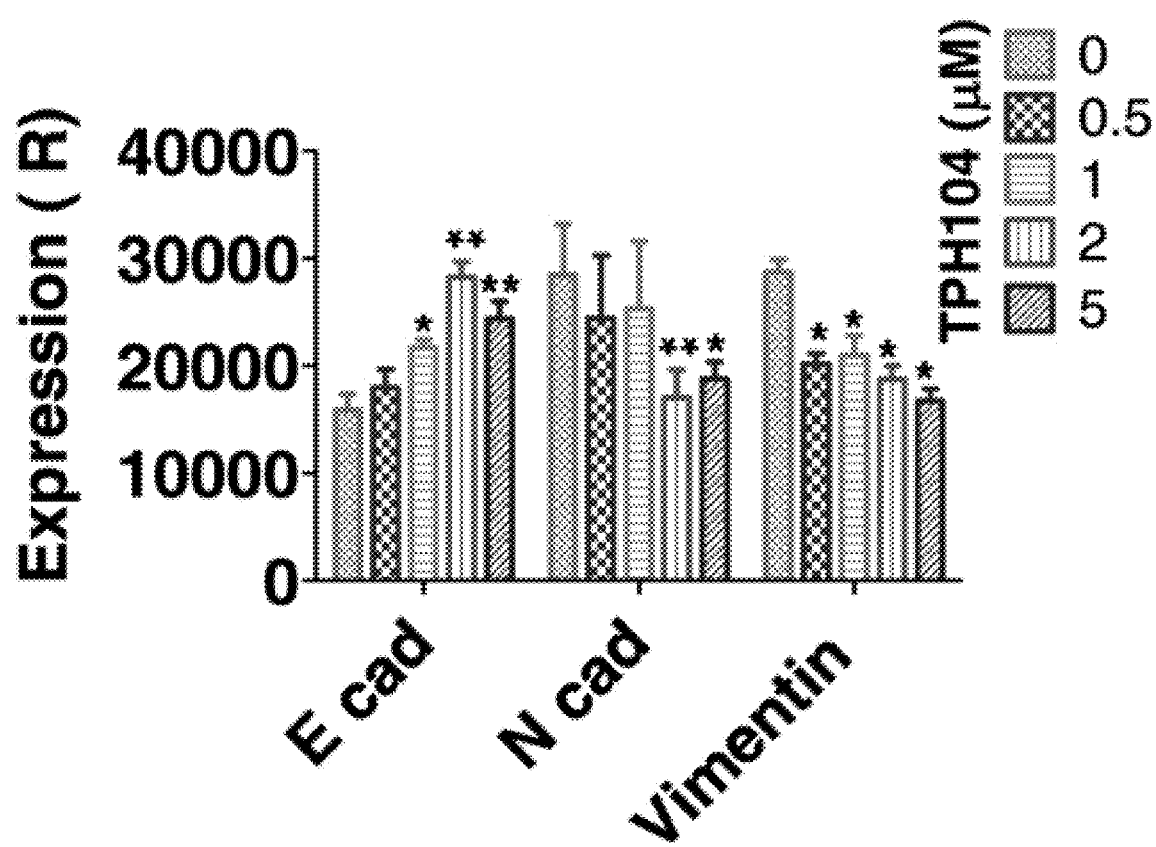
Figure 14C:
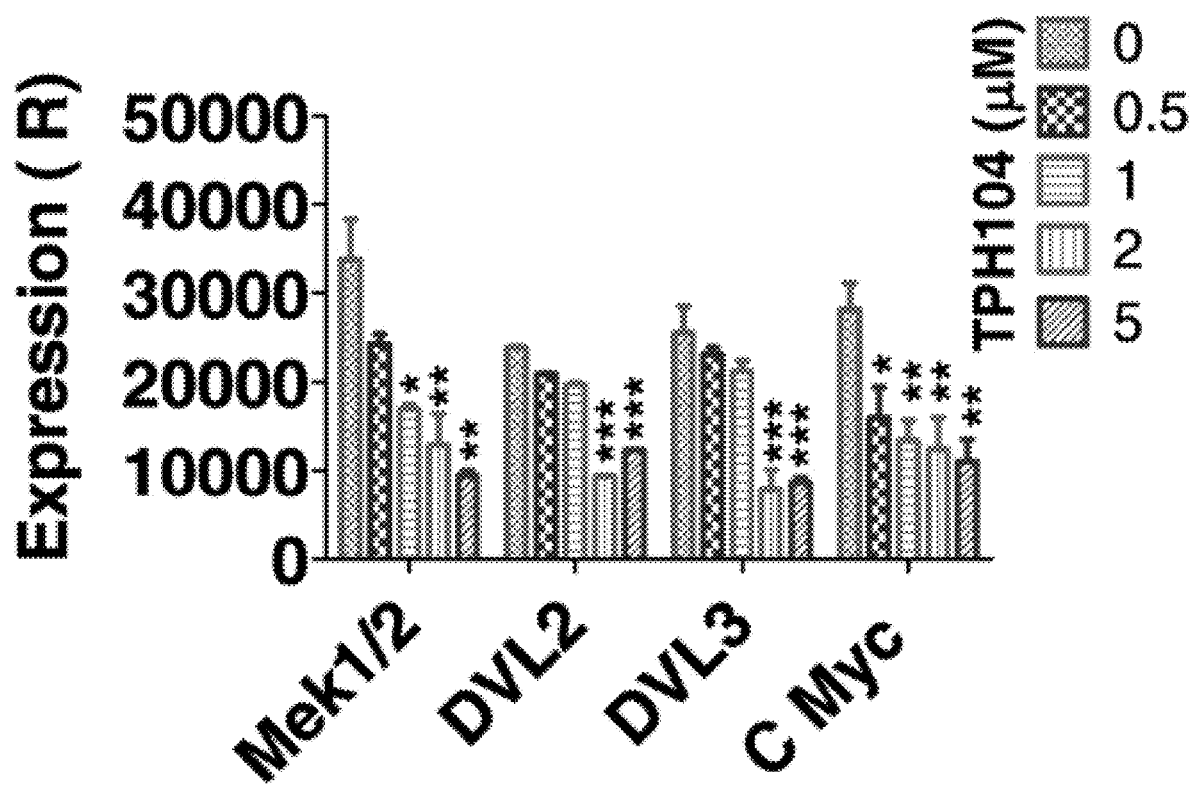

TPH104 Significantly Inhibits Epithelial-to-Mesenchymal Transition (EMT) Signaling in TNBC Cells In these experiments, the effect of TPH104 on EMT and Wnt/β-catenin signaling pathways was determined. This was done by determining the expression levels of some of the key proteins involved in the aforementioned pathways, including N-cadherin, E-cadherin, c-Myc, DVL3, DVL2, Vimentin, MEK1/2, LRP6, and β-catenin. As shown FIG. 14A-14B, TPH104 (1, 2, or 5 µM) significantly increased the expression of E-cadherin (E-cad), an epithelial marker, compared to cells incubated with vehicle ($p-<0.05$ for 1 µM and 2 µM; p-value<0.001 for 5 µM) in BT-20 cells. In contrast, TPH104 (2 µM and 5 µM), significantly decreased the expression of N-cadherin (N-cad), a mesenchymal marker (FIGS. 14A-14B; 2 µM ($p<0.01$) and 5 µM ($p<0.05$) in BT-20 cells, compared to cells incubated with vehicle. In addition, TPH104 (0.5, 1, 2, and 5 µM) significantly decreased the expression of c-Myc compared to cells incubated with vehicle (FIGS. 14A-14C). Moreover, BT-20 cells incubated with TPH104 (2 µM and 5 µM) (significantly decreased the expression levels of DVL3 ($p<0.001$), DVL2 ($p<0.001$), vimentin ($p<0.05$), and MEK1/2 ($p<0.01$) compared to cells incubated with vehicle (FIGS. 14A-14C). Interestingly, TPH104 (0.5, 1, 2, and 5 µM) did not significantly alter the expression of β-catenin or LRP6 in BT-20 cells, compared to the control (FIG. 14A). The results obtained with MDA-MB468 cells were similar to those for BT-20 cell. Overall, these findings indicated that TPH104 significantly increased the expression levels of epithelial markers and decreased the expression levels of both mesenchymal and Wnt/β-catenin signaling proteins.

Figure 15A:
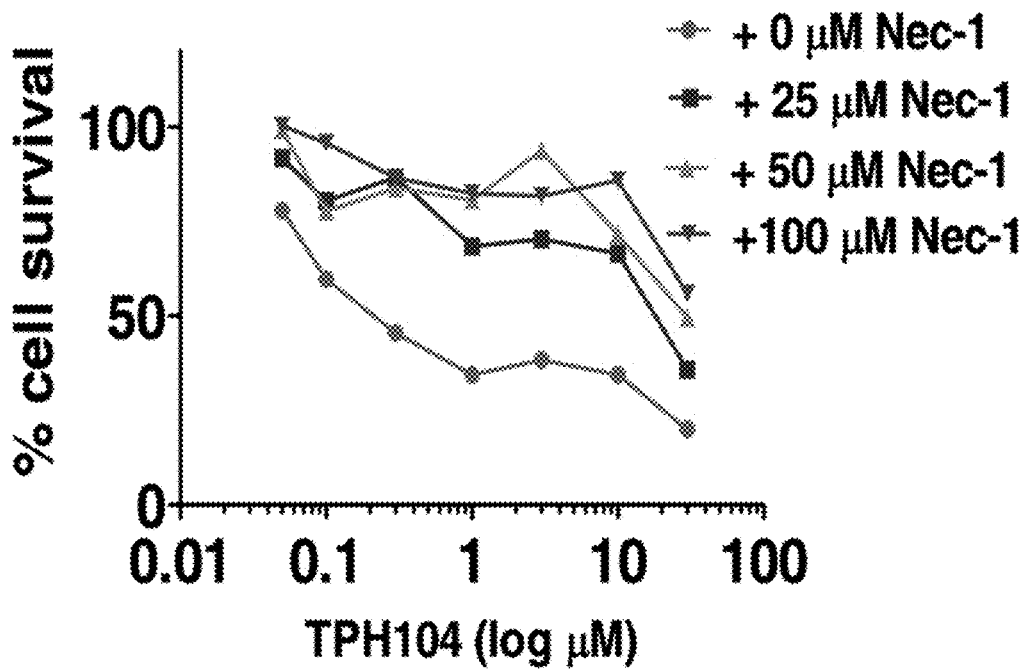
FIGS. 15A-15B: The cell survival curve of MDA-MB468 TNBC cells treated with TPH104 alone or in combination with 25, 50, or 100 μM Nec-1, a necroptotic cell death inhibitor (FIG. 15A).
Figure 15B:
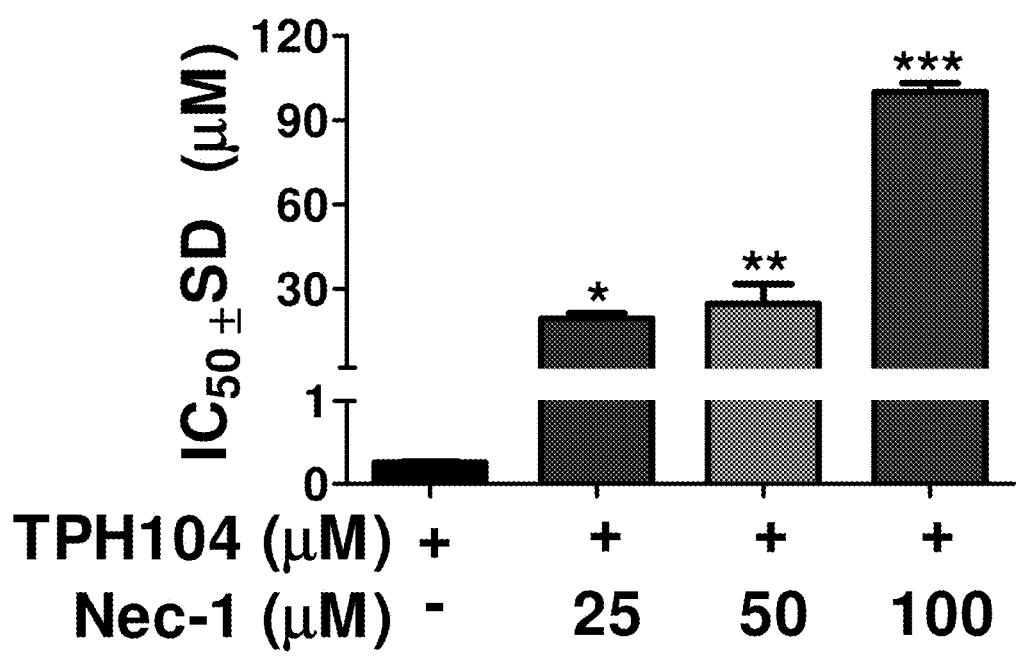

Furthermore, FIGS. 15A-15B show the increase in the $IC_{50}$ value of TPH104 when used in combination with varying concentrations (25, 50, and 100 µM) of necrostatin 1 (Nec-1) in MDA-MB468 TNBC cells. Nec-1 inhibits the necroptotic cell death mechanism and it blocked the necroptotic effect of TPH104.

Figure 16A:
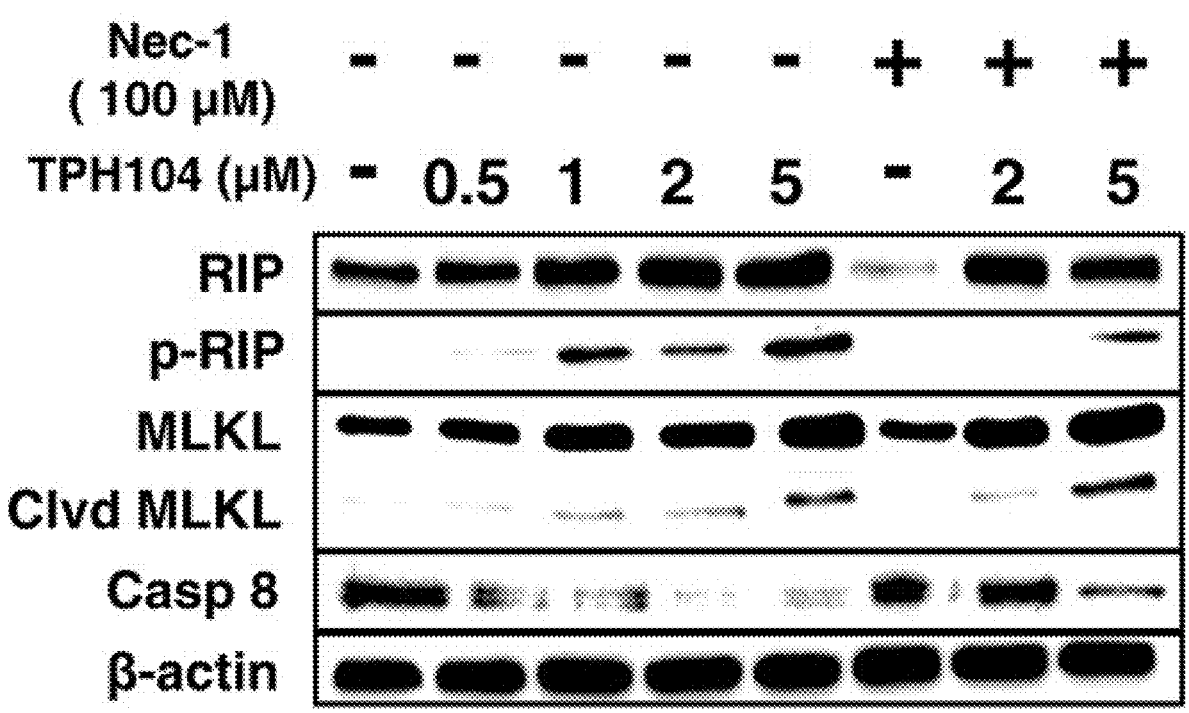
FIGS. 16A-16B: Western blot analysis for the expression of RIP, p-RIP, MLKL, clvd MLKL, and caspase8 (casp 8) (FIG. 16A). MDA-MB468 TNBC cells were incubated with (0, 0.5, 1, 2, and 5 μM) of TPH104 with and without 100 μM of necrostatin-1 (nec-1); β-actin levels were used to normalize cytosolic proteins.
Figure 16B:
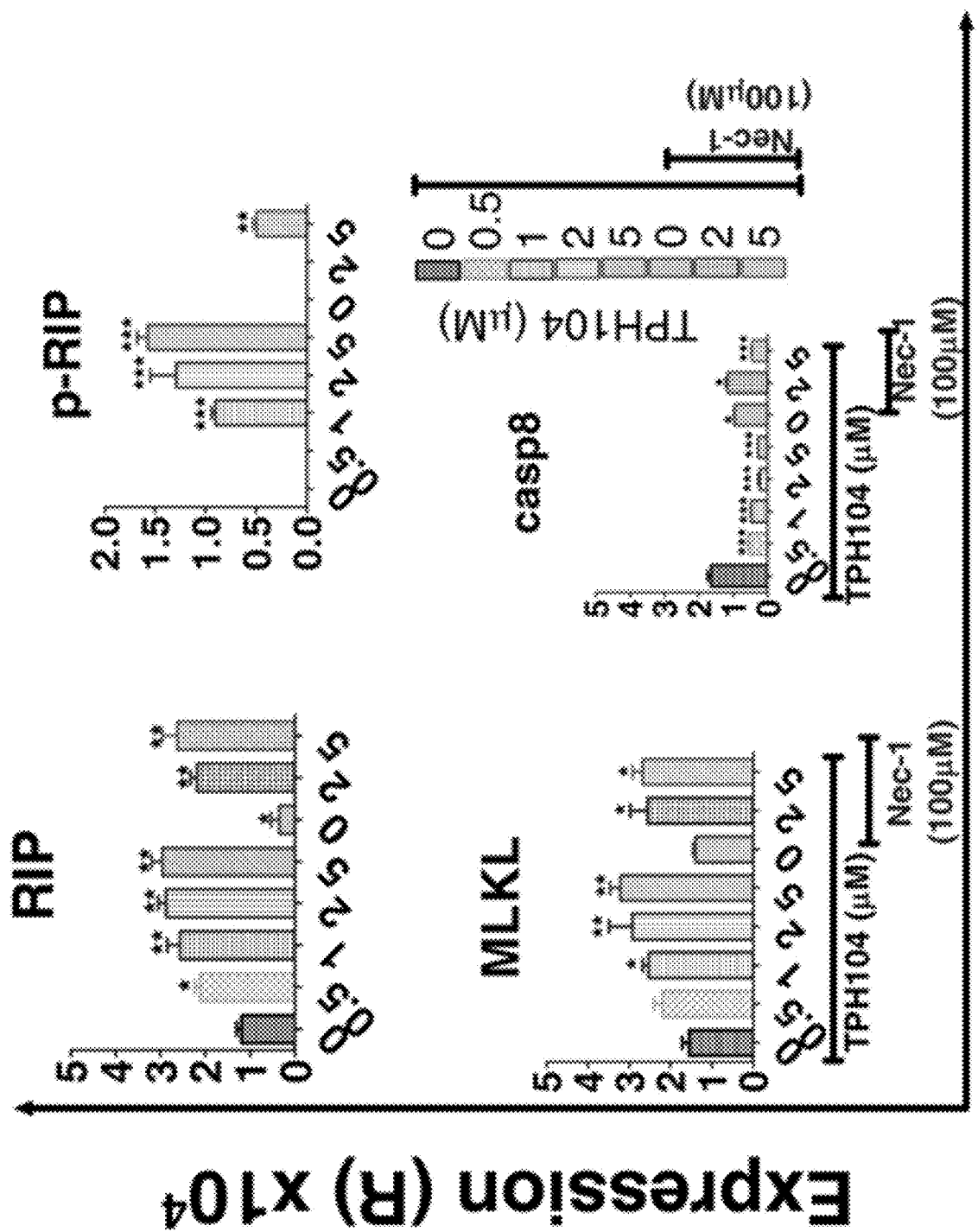

TPH104 Significantly Induces TRAIL-Mediated Necroptosis in TNBC Cells by Activating the Expression of Necroptotic Proteins The incubation of MDA-MB468 cells with TPH104 (1, 2, and 5 µM) significantly increased the expression of p-RIP compared to cells incubated with vehicle, which did not express p-RIP (FIGS. 16A-16B). During necroptosis, RIP phosphorylation is dispensable in the recruitment of the pseudokinase, mixed-lineage kinase domain-like (MLKL) protein, which subsequently activates the RIP-mediated necroptotic downstream. Therefore, the effect of TPH104 on MLKL expression was determined. The incubation of MDA-MB468 cells with TPH104 (1, 2, and 5 µM) significantly increased the expression levels of MLKL compared to cells incubated with vehicle (FIGS. 16A-16B). Furthermore, caspase 8 negatively regulates necroptosis since caspase 8 mediates apoptosis by inhibiting the RIP1-RIP3 necrosome complex. Therefore, the effect of TPH104 on caspase 8 was determined, and the results indicate that in MDA-MB468cells, TPH104 (0.5, 1, 2, and 5 µM) significantly decreased the expression of caspase 8 compared to cells incubated with vehicle (FIGS. 16A-16B). Previously, it has been shown that the endogenous protein necrostatin-1 (Nec-1) significantly inhibits RIP-mediated necroptosis in an ischemic mouse model. These results indicated that 100 µM nec-1 significantly downregulated the expression of RIP, as well as p-RIP, MLKL, and caspase 8 in MDA-MB468 cells (FIG. 16A).

In this example, it was discovered that TPH104 triggered TRAIL-mediated necroptosis (FIG. 20A), not TNF-mediated (FIG. 19A) in TNBC cells. TPH104-treated cells (0.5, 1, 2, or 5 µM) showed a significant increase in TRAIL, its receptor (DR5), RIP3, and TRADD (FIG. 20B). On the other hand, TPH104-treated cells showed no significant change in TNF-α (FIG. 19B). However, TPH104 significantly inhibited the expression of TNFR1, FADD, and Fas (FIG. 19B); and the inhibition of these proteins markers has been reported to favour necroptosis.

TPH104 Does Not Induce Autophagy in TNBC Cells

BT-20 cells were incubated with TPH104 concentrations (0.5, 1, 2, or 5 µM) or vehicle and for 12 hours to evaluate the effect of TPH104 on autophagy markers. As shown in FIG. 17A, BT-20 cells incubated with TPH104 did not show a significant increase in the fluorescence intensity of the acridine orange (AO) dye compared to cells incubated with vehicle. Similarly, BT-20 cells incubated with 20 µM of the negative control, chloroquine CQ, a reported autophagy inhibitor, showed no significant change in AO fluorescence intensity compared to cells incubated with vehicle. FIG. 17A illustrates the survival curve of TPH104 given alone or in combination with 0.5 mM of 3-methlyadenine (autophagy inhibitor) or 100 nM rapamycin (autophagy inducer). A significant increase in the percent cell survival was observed in BT-20 cells incubated with TPH104+100 nM rapamycin compared to BT-20 cells incubated only with TPH104. In contrast, there was no significant change in the percent BT-20 survival in the presence of TPH104+0.5 mM (FIG. 17A).

In addition, the effect of TPH104 on the expression levels of certain molecular protein markers of autophagy, including light chain protein 3 (LC3-I, which gets fragmented into LC3B-II during autophagy), LAMP1, ULK1, Rab7, and Rab7 was determined. The results indicated that TPH104 did not trigger fragmentation of LC3B-I into LC3B-II in BT-20 cells compared to cells incubated with vehicle (FIG. 18A-18B). During autophagy, lysosomal hydrolases degrade the cytosolic protein LC3-I into LC3-II which ultimately decreases the expression levels of LC3-I. In the experiments, LC3B-I levels were significantly increased with no significant increase in LC3B-II in BT-20 cells treated with TPH104 (0.5, 1, 2, or 5), indicating that TPH104 did not produce autophagy in BT-20 cells (FIGS. 18A-18B). To further confirm the inhibition of autophagy by TPH104, its effect on additional key autophagic cell death regulators (Beclin 1 and mTOR) was determined. The expression of Beclin 1, which plays a central role in the induction of autophagy, was significantly decreased in BT-20 cells following incubation with 1, 2, and 5 µM TPH104 for 12 h compared to cells incubated with vehicle. In contrast, the incubation of BT-20 cells with 1, 2, or 5 µM TPH104 for 12 h significantly increased the expression of mTOR, a protein that plays a vital role in the downregulation of autophagy compared to cells incubated with vehicle. Additionally, BT-20 cells incubated with TPH104 showed no significant change in the expression levels of lysosome-associated membrane protein 1 or LAMP1 compared to cells incubated with vehicle (FIGS. 18A-18B). LAMP1 has been shown to contribute to the fusion of lysosomes and autophagosomes to form autolysosomes during autophagy. Moreover, TPH104 (0.5, 1, 2, or 5 µM), significantly reduced the expression levels of unc-51-like kinase 1, ULK1, Rab5, and Rab7 in BT-20 cells incubated with TPH104 compared to cells incubated with vehicle (FIGS. 18A-18B).

Discussion

Figure 2B:
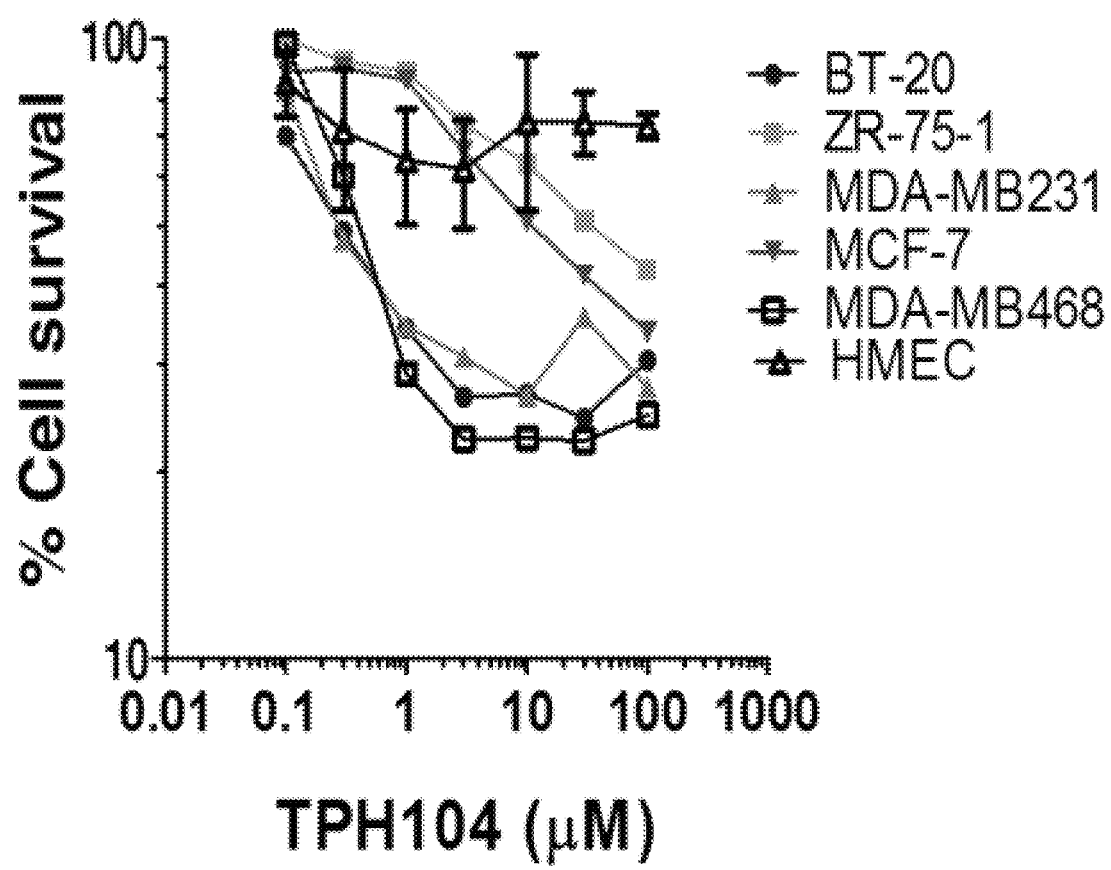
Figure 3A:
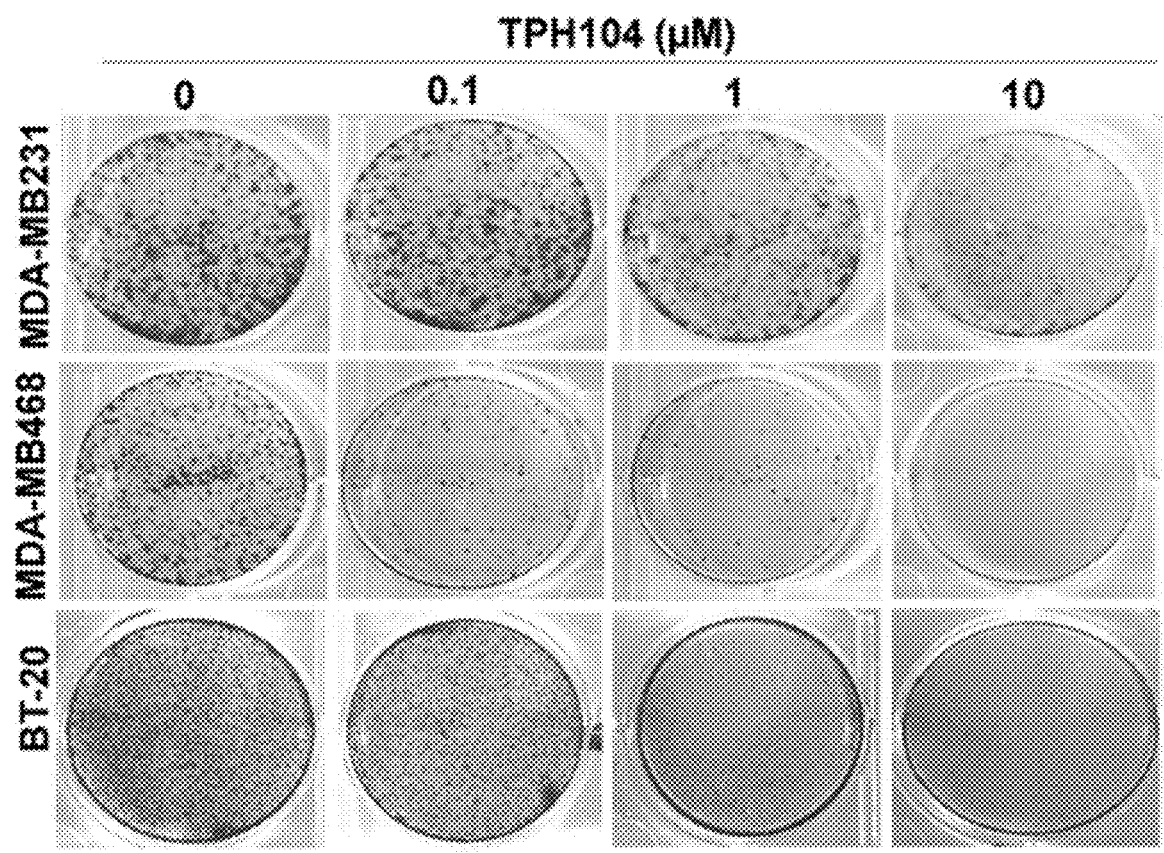
FIGS. 3A-3D: Colony formation assays for MDA-MB231, MDA-MB468, and BT-20 cell lines. Before quantifying the colony formation rate, cells were incubated with 0, 0.1, 1, or 10 μM of TPH104 for 12 h.
Figure 3B:
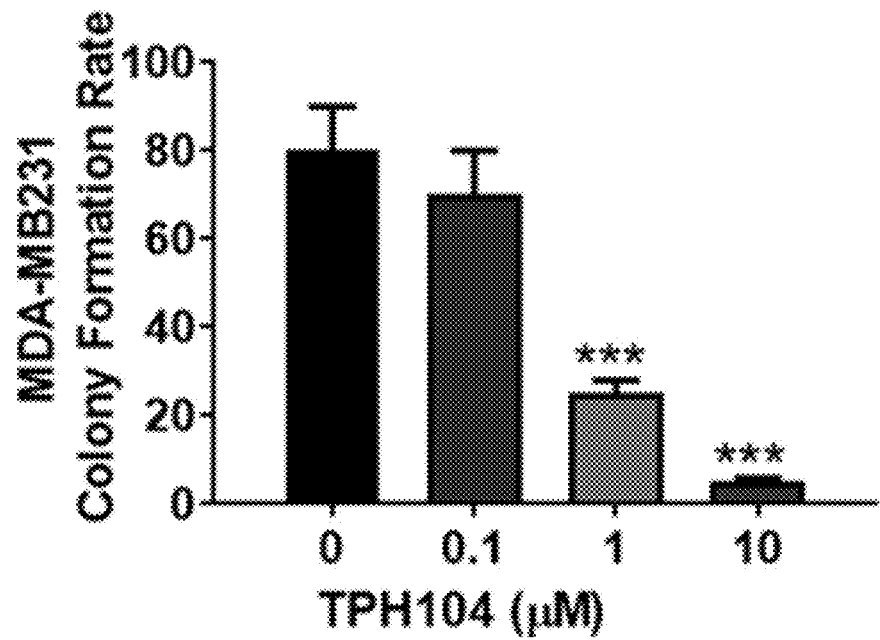
Figure 3C:
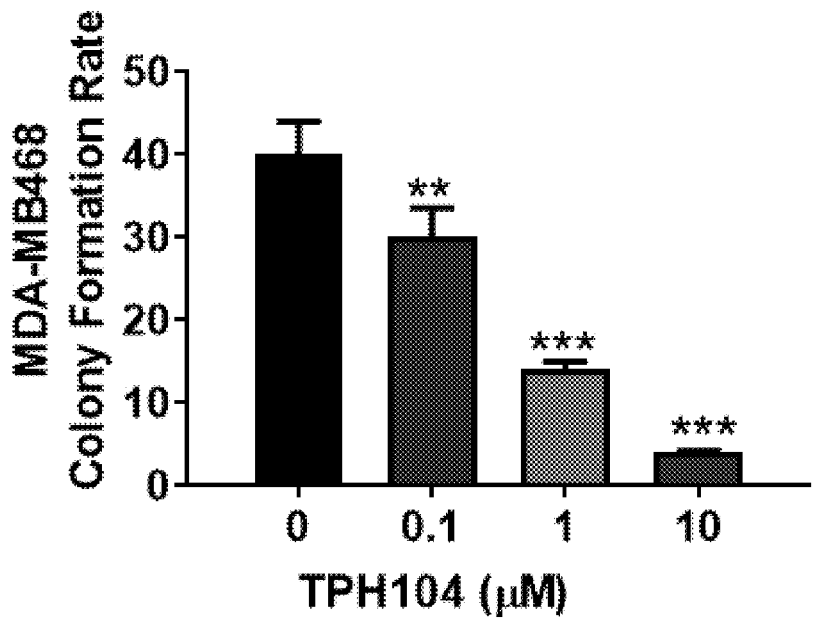
Figure 3D:
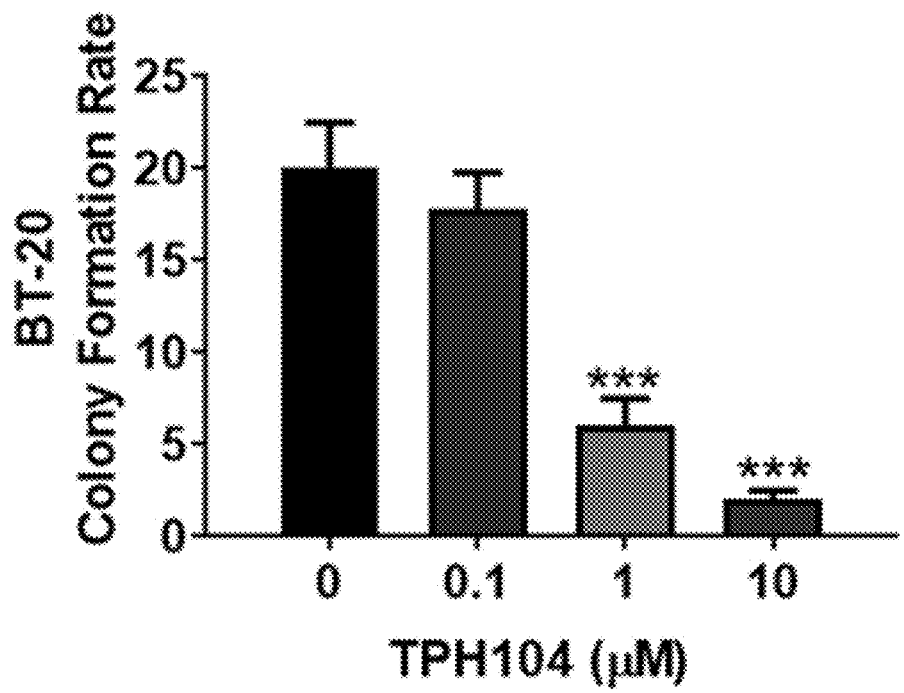

In this example, twelve thieno-pyrimidin-4-yl-hydrazinylidene class of compounds were screened. One compound, TPH104, was potently and selectively cytostatic in TNBC cells compared to other prominent cancer cells (Table 1 and Table 2). In addition, TPH104 had the lowest $IC_{50}$ value in the nanomolar range in TNBC cells, MDA-MB468, MDA-MB231, and BT20 compared to other non-TNBC cells, ZR-75-1 and MCF-7. The potent antiproliferative of TPH104 in TNBC cells correlates with another study whose reported findings showed the selectivity of LingH2-10 in TNBC cells due to its reverse agonistic affinity against estrogen-related receptor a (ERRα). ERRa contributes to a high recurrence rate and is overexpressed in a number of cancer types such as prostate, ovarian, cervical, colorectal, and breast (especially TNBC). Also, the selective antiproliferative activity of TPH104 in TNBC positively compares to another compound, chelerythrine, a protein kinase c inhibitor which had a strong antiproliferative in TNBC vs. non-TNBC cells. In drug discovery, the safety of any potential anticancer drug is one of the most important aspects which need to be evaluated before the drug is approved for clinical use. Therefore, the in vitro results revealed that TPH104 is safe in normal cells as it exhibited a high selectivity fold in its $IC_{50}$ value in human mammary epithelial cells, HMEC (FIG. 2B).

In addition to inhibiting cell proliferation, TPH104 significantly inhibited colony formation in TNBC cells, MDA-MB231, MDA-MB468, and BT-20 (FIG. 3). TNBC cells did not only show decreased in the density of their colonies but also a significant decrease in their size. This inhibitory effect of TPH104 on colony formation in TNBC cells contributes to its tumor suppressing efficacy as it has been previously reported for other compounds that inhibit the ability of cells to form colonies.

Moreover, TPH104 inhibited cell division and proliferation by eliciting cellular arrest in the S phase of the normal cell cycle. An actively dividing cell goes through the cell cycle which consists of four major phases: the M (active cell division), G1 (cell growth, organelles and proteins production), S (DNA synthesis), and G2 (cell growth, microtubules formation) phases. The S phase of the cell cycle denotes the stage at which dividing cells replicate their DNA in preparation to entering the G2 and subsequently mitosis. Consequently, blockage of the cell cycle at the S phase indicates that TPH104 would not only prevent cells from entering mitosis but also inhibit DNA replication in TNBC cells. Drugs that inhibit DNA replication such as pyrimidine analogs are widely used in the treatment of cancer.

Traditionally, most clinically available chemotherapeutic drugs target the apoptotic signaling pathway to induce programmed cell death. However, development of intrinsic and acquired apoptosis resistance has resulted in chemotherapy failure which subsequently resulted in poor prognosis in variety of advanced cancer such as breast, prostate, lung, colorectal and breast cancer among others. Therefore, the development of new pharmacological molecules which can act through a non-apoptotic cell death mechanism would not only be beneficial in treating drug resistance due to apoptosis resistance but also help circumvent apoptosis defects in solid tumor.

Hence, in this example, the effect of TPH104 on the expression levels of certain key apoptotic proteins such as Bak, Bax, Bcl-2, caspase 3, caspase 7, and caspase 9, which are mainly involved in the intrinsic apoptotic pathway, was determined. The results indicated that TPH104 significantly inhibited the expression pro-apoptotic such as Bax, caspase 3, cleaved caspase 3, and cleaved caspase 7, while it induced or showed no significant effect on some of the anti-apoptotic proteins including Bak and Bc12 (FIG. 10). Interestingly, TPH104 increased the fragmentation of PARP, which conventionally denotes activation of apoptosis because it gets cleaved by caspases and this is a hallmark of early onset of apoptosis. However, the cleavage of PARP has been shown in another non-apoptotic cell death mechanism and this shows that TPH104, although inducing PARP cleavage, is acting through a non-apoptotic mechanism. The effect of TPH104 on the expression of cytochrome c, which is released from mitochondria during the early stages of apoptosis, and then activates the caspase cascade, was also determined. The results showed that TPH104 significantly decreased the expression of the cytochrome c protein (FIG. 10). Additionally, TPH104 did not cause significant changes in mitochondrial membrane potential (FIGS. 6-7) and no nuclear condensation or fragmentation was observed in TNBC cells incubated with TPH104 (FIG. 8). Hence, this further confirms the non-apoptotic cell death effect of TPH104 as most apoptosis-inducing anticancer agents trigger nuclear condensation and DNA fragmentation in cancer cells. Lastly, the H2DCFDA stain was used to determine the effect of TPH104 on the generation of ROS in BT-20 cells. As previously reported, in this assay, cellular esterases cleave the non-fluorescent H2DCFDA to H2DCF by removing the lipophilic moiety (a diacetate group). Subsequently, H2DCF is oxidized by ROS to the fluorescent compound, DCF. Thus, an increase in DCF fluorescence levels positively correlates with an increase in ROS generation, an indication of oxidative stress. TPH104 (1, 2, 5 µM), did not significantly induce production of ROS compared to vehicle in vitro. This finding is unlikely due to the concentrations of TPH used as the same concentrations used in this study had significant cytotoxic effects and clearly affected the expression of other molecules. Furthermore, paclitaxel, as previously reported, significantly induced ROS formation in the TNBC cells in this example. Thus, the cytotoxic efficacy of TPH104 is not due to an increase in ROS levels. The anti-apoptotic effect of TPH104 was not significantly affected when cells were incubated with TPH104 along with z-VAD.fmk, a pan-caspase inhibitor (FIG. 9).

TPH104 significantly inhibited the invasive as well as migratory properties of TNBC cells (FIGS. 12-13). As already mentioned, TNBC tumors are highly metastatic in nature; therefore the ability of TPH104 to inhibit migration and invasion positively correlated with its in vitro anti-metastatic effect in TNBC cells as it has been previously reported. The inhibition of the ability of solid tumors to invade, migrate, and metastasize is of great clinical advantage in cancers that can spread to other organs in the body. Hence TPH104 could represent a novel pharmacological small molecule which has the potential to halt cancer cells from metastasizing to other parts of the body. The effect of TPH104 on the EMT and Wnt/β-catenin signaling pathways was also evaluated by determining its effect on the expression levels of some of the vital proteins involved in the aforementioned pathways. Aberrations in the Wnt signaling pathway have been associated with the aggressive characteristic of TNBC tumors. Wnt signaling pathway plays a substantial role in promoting tumor progression, cancer metastasis, cancer cell migration, cancer cell invasion, and ultimately poor clinical outcomes in TNBC patients. Consequently, any drug that inhibits the positive regulators of the Wnt signaling pathways would be of significant clinical relevance in the treatment of metastatic TNBC tumors. Also, studies have highlighted the implication of the Epithelial-mesenchymal transition (EMT), a developmental process in which epithelial cells lose polarity and acquire invasive and migratory properties to become mesenchymal cells, in the highly metastatic and recurrent behaviors associated with TNBC. Through western blotting, it was shown that TPH104 significantly reduced the expression levels of mesenchymal (N-cadherin) and metastatic (Vimentin, MEK1/2, DVL2, DVL3,C-myc, and LRP6) protein markers and significantly increased the expression of the epithelial marker (E-cadherin) compared to cells incubated with the vehicle (FIG. 14). In addition, TNBC cells incubated with TPH104 had a substantial decrease in the expression levels of c-Myc compared to cells incubated with vehicle. The c-Myc protein has been shown to induce EMT and promote cancer metastasis. The inhibition of the overexpression of the c-Myc protein has also been shown to overcome drug resistance in TNBC. Interestingly, TPH104 significantly decreased the expression of β-catenin in one TNBC cell (MDA-MB468) but not the other (BT-20). Altogether, these findings revealed the in vitro anti-metastatic effect of TPH104 in TNBC cells.

Interestingly, in addition to inhibiting apoptosis, TPH104, inhibited autophagy, another well-characterized form of non-apoptotic cell death. Autophagy has been defined as a genetically regulated process which promotes the degradation of long-lived proteins or organelles by lysosomal vacuoles in order to maintain cellular survival. Autophagy helps promote cancer cell survival by enabling tumor cells to maintain macromolecular synthesis and energy homeostasis during low-oxygen conditions, nutrient deficiency, and various other kinds of cellular stress. Autophagic cell death is regulated by a number of molecular markers among which LC3-I and LC3-II proteins are essential in the formation of autolysosomes which then leads to the autophagic response. Autophagy is also defined as adaptive cellular mechanism through which cancer cells evade treatments and thus confers chemoresistance in TNBC. It has been reported that induction of autophagy can be highly beneficial to solid tumors by promoting cancer cell survival, proliferation and aggressiveness. Autophagy can be induced as a survival response to some chemotherapeutic agents leading cancer cells to develop resistance to anticancer drugs. Although moderate autophagy plays a tumor suppressing role in early tumor development stages, autophagy-induced chemoresistance has been shown to be enhanced by metabolic stress, continued exposure to chemotherapy and all these factors will subsequently lead to cancer cell metastasis. The inhibition of autophagy has yielded an increased cytotoxic effect of certain treatments in TNBC including doxorubicin, a clinically available drug used in the treatment of TNBC. TPH104 did not cause any significant change in the expression levels of LC3-II, which mediates the fusion of autophagosomes and lysosomes to produce autolysosomes which subsequently leads to autophagy induction. During autophagy, LC3-I gets conjugated into LC3-II, but this example did not show any increase in LC3-I conjugation as the expressions levels of LC3-I were significantly higher than LC3-II expression levels (FIG. 18). Moreover, inhibition of autophagy, in both in vitro and in vivo TNBC models, has been shown to increase the cytotoxic effect of geftinib, a clinically available anticancer agent used in the treatment of breast cancer. It has been reported that the cytotoxic effect of Doxorubicin, one of the widely used anticancer agents in TNBC patients, is significantly increased when given in combination with 3-Methyladenine (3-MA), an autophagy inhibitor. In this example, BT-20 TNBC cells incubated with TPH104 in combination with 3-MA did not yield significant change in the cell survival rate or $IC_{50}$ of TPH104 (FIG. 17B); this means that TPH104 alone can potently inhibit autophagy. On the other hand, the combination of rapamycin, a well-established mTOR inhibitor and autophagy inducer, with TPH104 significantly increased BT-20 TNBC cell survival and increase in its $IC_{50}$; thus showing no synergistic effect between TPH104 and autophagy-inducing drugs. It has been shown that the inhibition of the mTOR protein, another key positive regulator of autophagy and cell survival, resulted in an increase in autophagy, cell proliferation and cell viability. In contrast, TPH104 significantly increased the expression levels of the mTOR protein, which ultimately confirms its anti-proliferative effect among other advantages of inhibiting autophagy in TNBC. Also, as shown in the results (FIG. 18), TPH104 is a potent autophagy inhibitor as it significantly decreased the expression levels of the beclin 1 protein, which is another well studied and characterized protein that plays a critical role in the formation of autophagosomes and hence initiating autophagy. Lastly, other positive markers of autophagy (ULK1, LAMP-1, Rab5 and Rab7) were also significantly inhibited (FIG. 18). ULK has been shown to maintain autophagy initiation as well as induce phosphorylation of Beclin-1 during autophagy. Rab 7 has been shown play a role in the maturation of autophagosomes as well as the formation of lysosomes whereas Rab5 is reported to be essential in the early stages of macroautophagy in mammalian cells. In cancer therapy, many other autophagy inhibitor compounds have attracted attention and this makes our compound novel especially in the development of TNBC treatments. Moreover, AO dye was used to evaluate autophagy in BT20 and MDA-MB468 TNBC cells, and no significant increase in AO fluorescence was seen. When AO dye gets inside the lysosomes and other acidic cellular compartments, it gets protonated and gives off orange fluorescence which correlates to the formation of lysosomal autophagosomes, one of the hallmarks of autophagy. Chloroquine (CQ), an autophagy inhibitor, was used as a negative control and there was no significant difference in AO fluorescence between BT-20 cells incubated with either TPH104 or CQ (FIGS. 17A-17B).

Taken together, the in vitro results indicate that TPH104 is a potential anticancer drug because it does not only target chemoresistance that arises from apoptotic defects but also can bypass chemoresistance resulting from upregulated autophagy in TNBC treatment.

Lastly, in this example, it is shown that TPH104 selectively induced TRAIL-mediated necroptosis, a cell death mechanism characterized by necrotic morphological features including organelles swelling, cellular membrane rupture, release of cellular contents, etc., in TNBC cells. TPH104 significantly increased the expression of necroptotic effector proteins, RIP, p-RIP, and MLKL inhibited the expression levels of caspase 8 (FIGS. 16A-16B). In addition, TPH104 selectively induced TRAIL-mediated necroptosis in TNBC cells. Moreover, TNF-α mediated necroptosis has been the most commonly studied and it has been reported that TNF-α induced necroptosis in colon cancer cells and in the mouse L929 fibrosarcoma cell line. However, other studies have also highlighted the role of TRAIL and PARP-1 in inducing necropstosis. One study reported that TRAIL induced necroptosis and this pathway requires RIP1, RIP3, and PARP-1 activation. TPH104 significantly increased the expression of TRAIL, its receptor (DR5), RIP3, and TRADD (FIG. 20B). On the other hand, TPH104-treated cells showed no significant change in TNF-α (FIG. 19B). However, TPH104 significantly inhibited the expression of TNFR1, FADD, and Fas (FIG. 19B); and the inhibition of these proteins markers has been reported to favour necroptosis.

Necroptosis differs from apoptosis as it occurs in the absence of the activity of caspases. Necroptosis has been described as pro-inflammatory cellular death mechanism which leads to the release of endogenous molecules termed damage-associated molecular patterns (DAMPs). These DAMPs, released upon cell lysis/plasma membrane rupture, have been extensively characterized and showed to promote immune responses. Therefore, necroptosis inducers could stimulate an immune response that would essentially lead to cancer cell death. Also, accumulating evidence shows that necroptosis is initiated when caspase-8 is deficient by key molecular markers: RIP1, RIP3, and MLKL. In the experiments in this example, the incubation of MDA-MB468 cells with 1, 2, or 5 μM of TPH104 for 12 h significantly increased the expression of RIP1 compared to cells incubated with vehicle (FIGS. 16A-16B). The results also showed that TPH104 inhibited the expression levels of caspase 8. The discovery of RIP inhibitors, necrostatins, sparked interest in RIP-mediated, caspase-independent non apoptotic necroptotic cell death. It has been shown that RIP3 phosphorylates RIP1 and activates the necroptotic cascade by forming a necrosome complex. Therefore, the effect of TPH104 on phosphorylated RIP (p-RIP) levels was tested. The results showed a significant increase in the expression of p-RIP in MDA-MB468 and BT-20 TNBC cells incubated with TPH104 (1, 2, and 5 μM). The activation of RIP leads to the recruitment of its substrate, MLKL, which in turn gets phosphorylated and translocates to the intracellular membrane and subsequently leads to cellular membrane rupture, a hallmark of necroptois. TPH104 significantly increased the expression levels of MLKL. Although some published reports claim that in addition to triggering apoptosis, mitochondrial ROS plays a key role in necroptosis, other studies have shown that this claim is true in some but not all types of cells. These results also support the suggestion that the involvement of ROS in necroptosis is rather cell-type specific since TPH104 induced necroptosis in TNBC cells without triggering ROS release. In addition, the incubation of TPH104 in combination with varying concentrations of nec-1 significantly blocked the necroptotic effect of TPH104 as this resulted in an increase in cell survival and $IC_{50}$ of TPH104 (FIGS. 15A-15B).

As noted earlier, the initial results indicated that TPH104 elicited PARP-1 cleavage and this means that TPH104 is triggering necroptosis through PARP-1 pathway inTNBC cells. The results correlate with another study which reported the role of PARP-1 mediated necroptosis in L929 cells.

In conclusion, neo-pyrimidine compounds were screened against a panel of different cancer cell lines including TNBC, non-TNBC, ovarian, colon, prostate, and lung cell lines. One compound, TPH104, which was selectively cytotoxic against TNBC cell lines, was identified. TPH104 had a significantly lower $IC_{50}$ (<1 μM) in TNBC cell lines compared to other prominent cancer cell lines. Moreover, TPH104 had more than 100 selectivity fold on TNBC cells compared to normal human mammary epithelial cells. TPH104 also had up to 30 selectivity fold in comparison to other normal cell lines (colon and kidney). In addition, TPH104 induced cellular arrest at the S phase of the cell cycle, and significantly inhibited cellular proliferation, migration, invasion, colony formation, and metastasis in TNBC cells. These results revealed that TPH104 induced a non-apoptotic, non-authophagic cell death mechanism in TNBC cells. Increased expression of TRAIL and DR5 drive the necroptotic pathway in a feed forward manner by inhibition of caspase 8 is needed to initiate apoptosis by degrading RIPK1. Modulation of autophagy markers further strengthen necroptotic pathway ensued in BT-20 cells (FIG. 22). TPH104 induced cellular death through TRAIL-mediated necroptosis, a programmed necrosis. These findings indicate that TPH104 compounds represent a group of autophagy inhibiting, necroptotic inducing novel molecules which target TNBC tumors and may have therapeutic significance in cases where either apoptosis is abrogated or autophagy is upregulated.

Additional Data on TPH104 Selectivity, Resistance, Toxicity, and Mechanisms

Acute toxicity data for TPH104 in C57BL/6 male mice showed no obvious toxicity in mice upto 50 mg/kg through histochemistry and blood chemistry analysis (FIGS. 23A-23E).

Interestingly, when TPH104 was combined with mitoxantrone, TPH104 increases its efficacy in colon and non-small cell lung cancer cells, including those that were resistant to Mitoxantrone (FIG. 24). Similar data was obtained with doxorubicin and paclitaxel. This indicates that TPH104 compounds can be used as chemoadjuvants in cancer therapy.

It was observed that TPH104 downregulated the expression of ABCG2 transporter in a concentration dependent fashion in drug resistant small cell lung cancer cells (H460/MX20), colon cancer cells (S1M180), and ABCG2-transfected cells (HEK293/R2) (FIG. 25). Further, TPH104 increased the intracellular accumulation of Rhodamimine 123, a known substrate of ABCG2 transporter (FIG. 26). This indicates that TPH104 can modulate the functions of ABCG2 transporters.

Mechanistically, it was observed that TPH104 reverses ABCG2 transporter mediated multidrug resistance by producing collateral sensitivity, i.e., is more effective in drug resistant cells overexpressing ABCG2 transporters (FIG. 27).

Figure 28A:
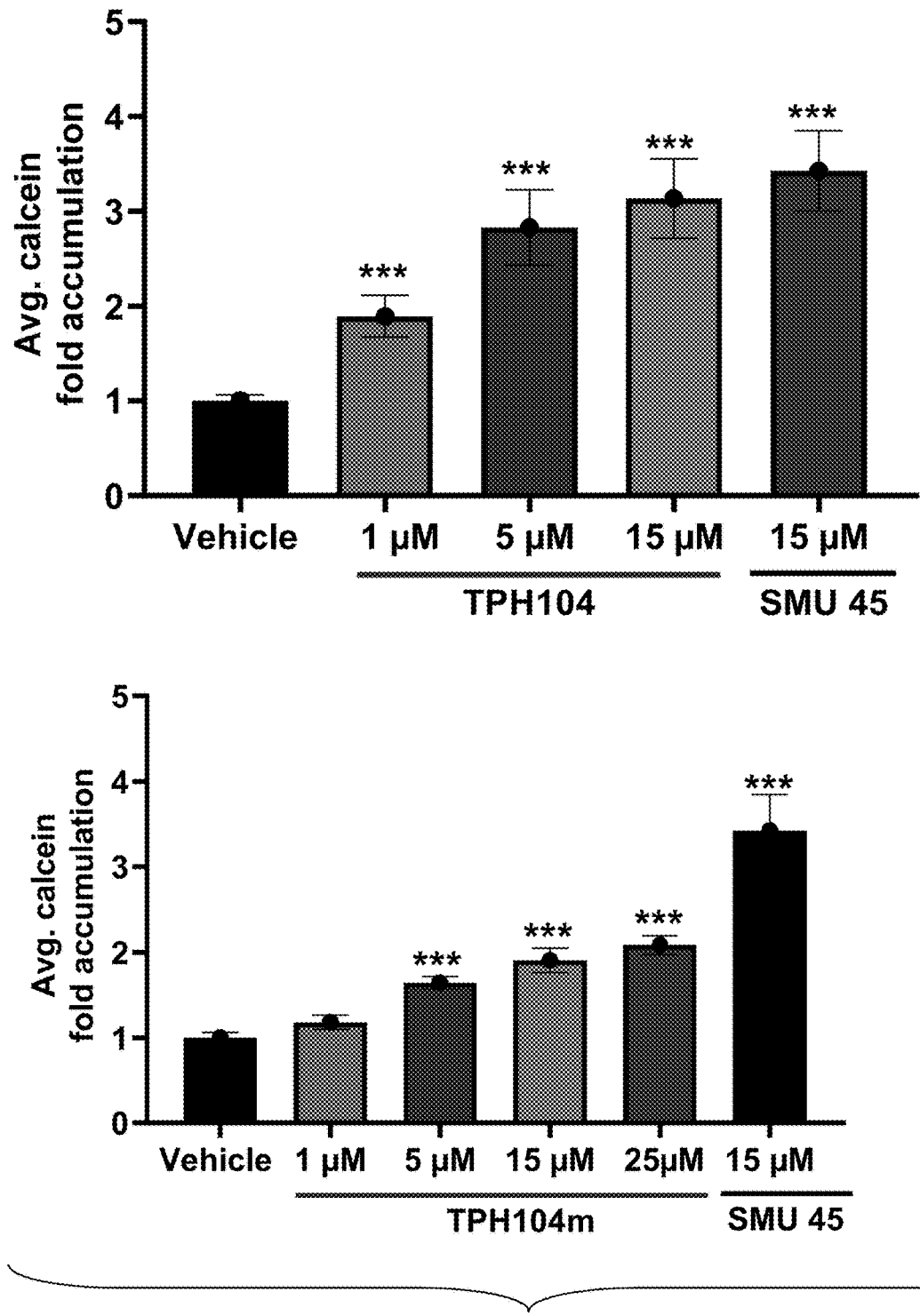
Figure 28B:
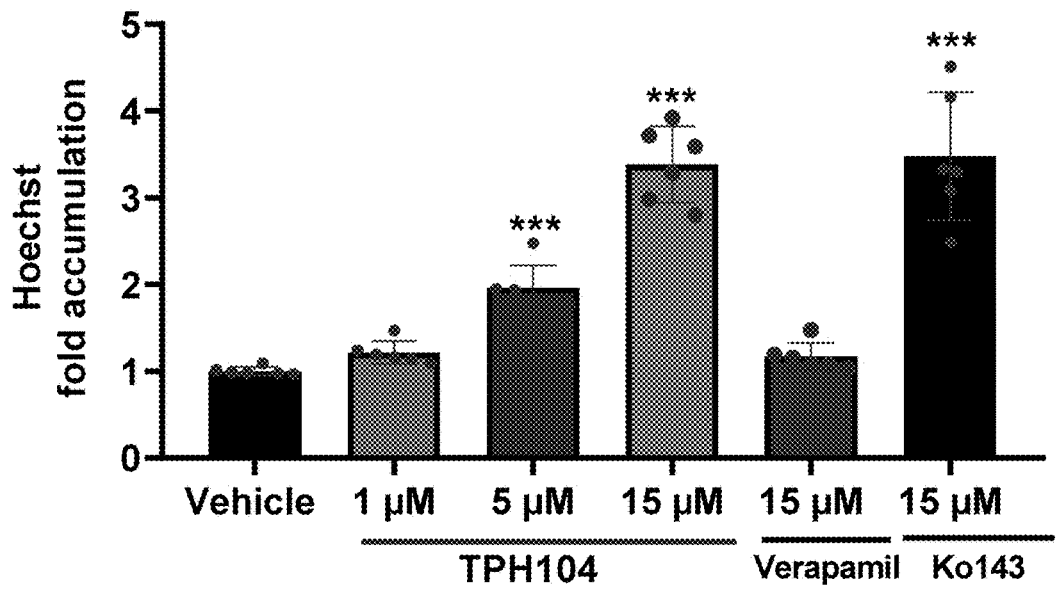
Figure 28B:
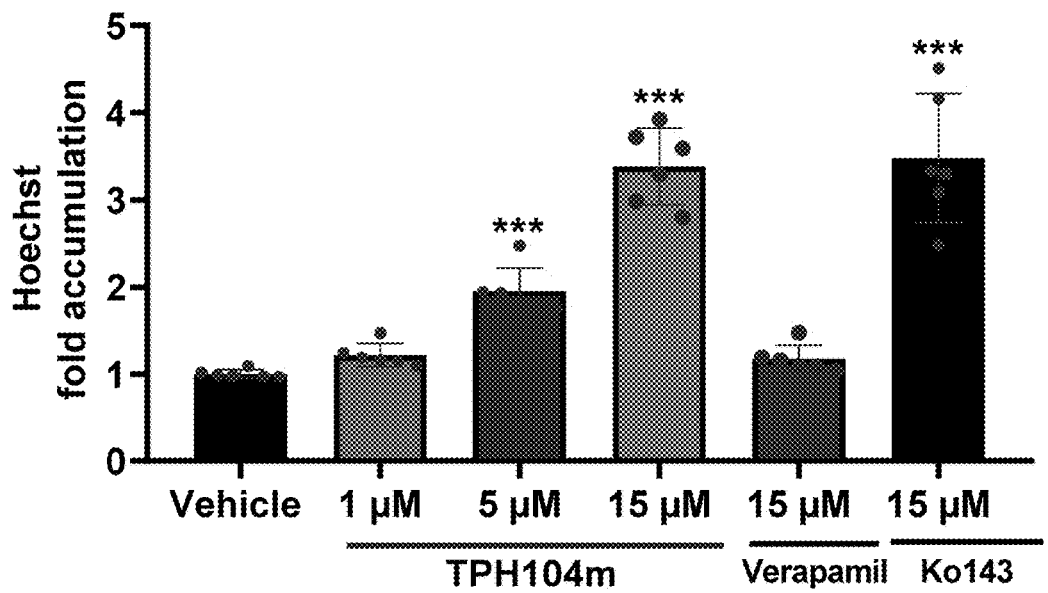

Further, it was observed that TPH104 and TPH104m can reverse ABCB1 and ABCG2 mediated drug resistance by blocking the efflux function of these transporters in concentration dependent fashion (FIG. 28). These data indicate that in addition to being used as a modulator to ABC transporters, TPH104 and its analogues may be used as a chemosensitizers in reversing drug resistance mediated by the efflux transporters.

Certain embodiments of the compositions, compounds, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of inducing cell death, the method comprising administering to a cell an effective amount of a compound to induce death of the cell, wherein the compound comprises TPH104:

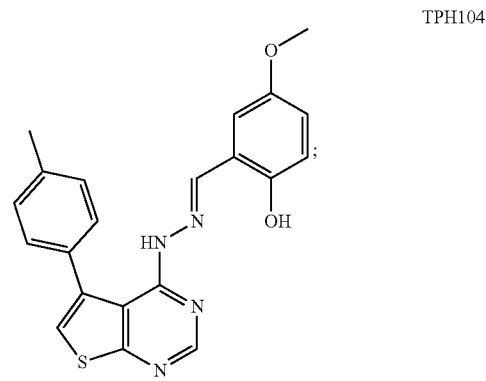 [SMILES: COc1ccc(O)c(/C=N/Nc2ncnc3scc(-c4ccc(C)cc4)c23)c1]

wherein the cell is a cancer cell; and wherein the cancer is triple negative breast cancer, colon cancer, prostate cancer, ovarian cancer, or lung cancer.

2. A method of inducing cell death, the method comprising administering to a cell an effective amount of a compound to induce death of the cell, wherein the compound is selected from a group consisting of:

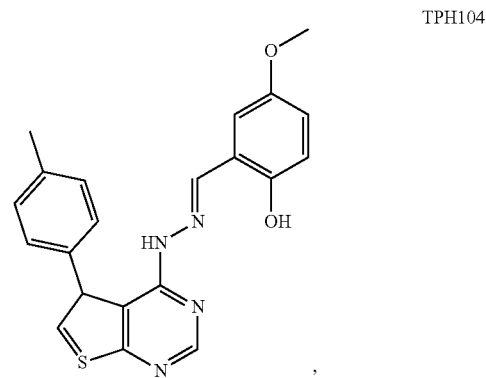 [SMILES: COc1ccc(O)c(/C=N/Nc2ncnc3scc(-c4ccc(C)cc4)c23)c1]

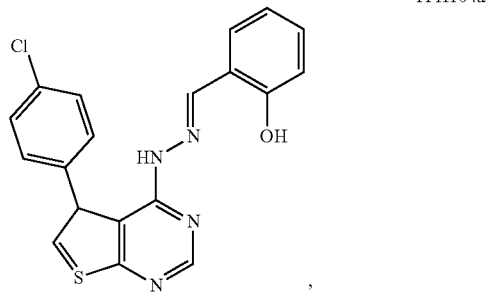

-continued
TPH104b
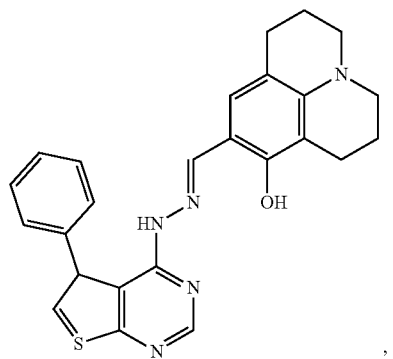
TPH104c
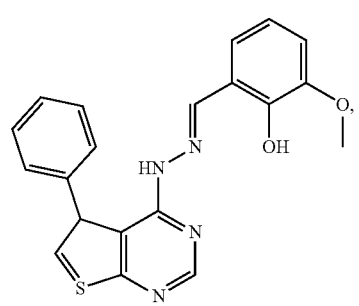
TPH104d
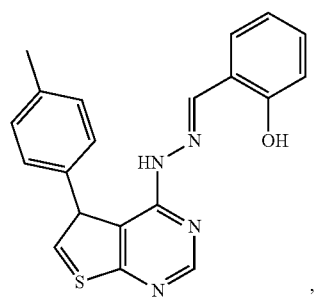
TPH104f
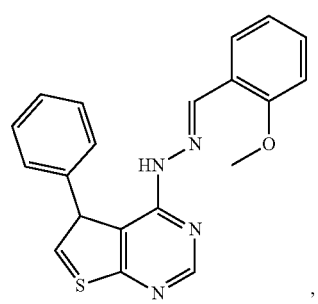
TPH104g
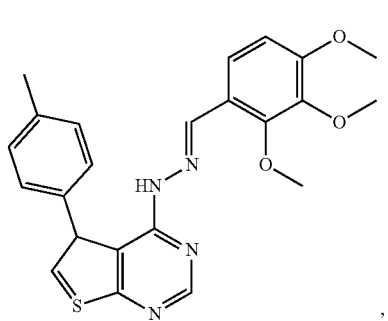
-continued
TPH104h
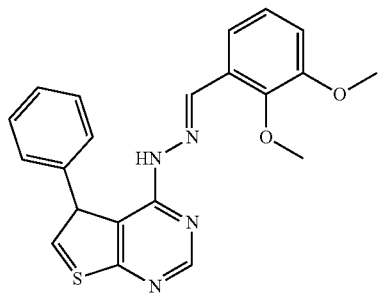
TPH104j
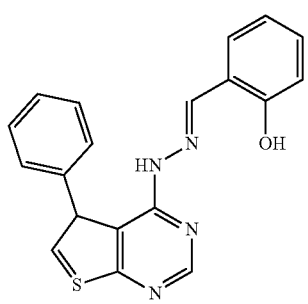
TPH104k
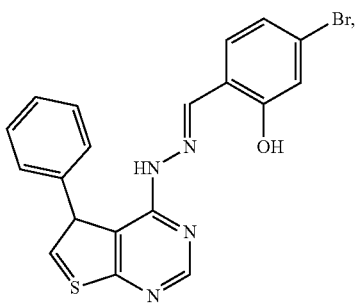
TPH104l
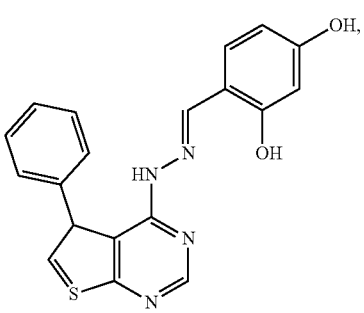
TPH104m
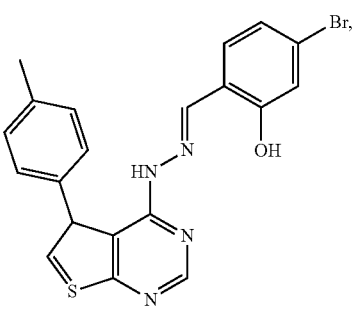

TPH104n
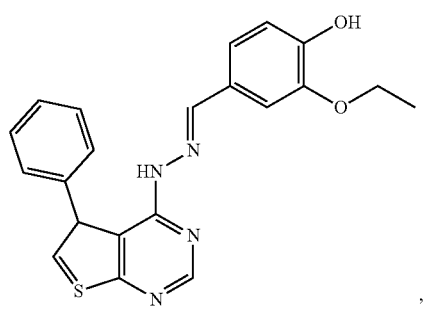
TPH104o
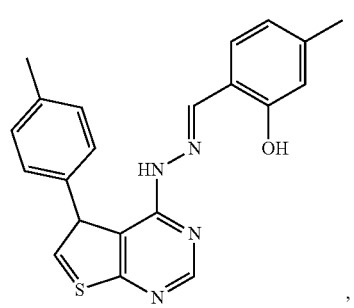
TPH104p
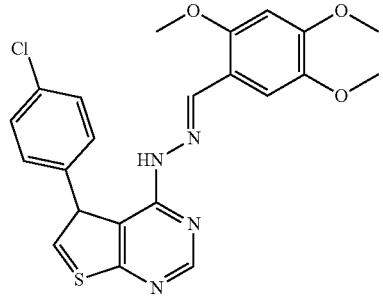
, and
TPH104q
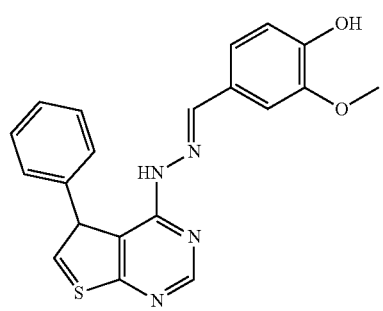
;
wherein the cell is a triple negative breast cancer cell.
* * * * *